(12) United States Patent
Ulm, III et al.

(10) Patent No.: US 10,888,346 B2
(45) Date of Patent: Jan. 12, 2021

(54) CLOT RETRIEVAL SYSTEM

(71) Applicant: Legacy Ventures LLC, Nashville, TN (US)

(72) Inventors: Arthur John Ulm, III, Nashville, TN (US); Maurice de la Rosa, Santa Rosa, CA (US)

(73) Assignee: Legacy Ventures LLC, Nashville, TN (US)

( * ) Notice: Subject to any disclaimer, the term of this patent is extended or adjusted under 35 U.S.C. 154(b) by 213 days.

(21) Appl. No.: 16/241,616

(22) Filed: Jan. 7, 2019

(65) Prior Publication Data

US 2019/0133619 A1    May 9, 2019

Related U.S. Application Data

(63) Continuation-in-part of application No. 15/311,849, filed as application No. PCT/US2015/031447 on May 18, 2015, now Pat. No. 10,357,266, which is a continuation-in-part of application No. PCT/US2015/010178, filed on Jan. 5, 2015, and a continuation-in-part of application No. 14/558,712, filed on Dec. 2, 2014, now Pat. No. 9,155,552, and a
(Continued)

(51) Int. Cl.
| | |
|---|---|
| *A61B 17/221* | (2006.01) |
| *A61B 17/22* | (2006.01) |
| *A61B 17/00* | (2006.01) |
| *A61B 90/00* | (2016.01) |

(52) U.S. Cl.
CPC .. *A61B 17/221* (2013.01); *A61B 2017/00469* (2013.01); *A61B 2017/00477* (2013.01); *A61B 2017/00526* (2013.01); *A61B 2017/00867* (2013.01); *A61B 2017/2212* (2013.01); *A61B 2017/22038* (2013.01); *A61B 2017/22094* (2013.01); *A61B 2090/064* (2016.02); *A61B 2090/3966* (2016.02)

(58) Field of Classification Search
CPC ... A61B 2090/064; A61B 17/221; A61F 2/01; A61F 2/0103; A61F 2/0105; A61F 2/0108; A61F 2/011; A61F 2/012; A61F 2/013; A61F 2/014; A61F 2002/015; A61F 2002/016; A61F 2002/018
See application file for complete search history.

(56) References Cited

U.S. PATENT DOCUMENTS

| | | | |
|---|---|---|---|
| 4,721,507 A | * | 1/1988 | Chin .................. A61B 17/3207 600/587 |
| 4,890,611 A | | 1/1990 | Monfort et al. |
| | | | (Continued) |

OTHER PUBLICATIONS

PCT International Search Report in corresponding International Application No. PCT/US2020/012554, dated Mar. 25, 2020.

*Primary Examiner* — Thomas McEvoy
(74) *Attorney, Agent, or Firm* — Shane Cortesi

(57) ABSTRACT

A platform of devices for removing obstructions and other objects within a blood vessel or other interior lumen of an animal is provided. The system may be deployed in the lumen from a catheter(s) and may include a strain gauge for measuring tension on the pull wire. A number of different baskets designs are disclosed. Methods of manufacturing such baskets out of a single tube of a memory metal without the need for any welding, and methods of use are also disclosed.

19 Claims, 38 Drawing Sheets

Related U.S. Application Data continuation-in-part of application No. 14/558,705, filed on Dec. 2, 2014, now Pat. No. 9,173,668.

(60) Provisional application No. 61/994,919, filed on May 18, 2014, provisional application No. 61/994,934, filed on May 18, 2014.

(56) References Cited

U.S. PATENT DOCUMENTS

| | | |
|---|---|---|
| 6,059,759 A | 5/2000 | Mottola et al. |
| 6,357,296 B1 | 3/2002 | Baker et al. |
| 6,817,973 B2 | 11/2004 | Merril et al. |
| 7,072,703 B2 | 7/2006 | Zhang et al. |
| 8,052,621 B2 | 11/2011 | Wallace et al. |
| 8,388,556 B2 | 3/2013 | Wallace et al. |
| 8,512,389 B2 | 8/2013 | Ayala et al. |
| 8,834,390 B2 | 9/2014 | Couvillon, Jr. |
| 9,078,682 B2 | 7/2015 | Lenker et al. |
| 9,204,841 B2 | 12/2015 | Clark et al. |
| 9,375,553 B2 | 6/2016 | Chrisman |
| 9,404,734 B2 | 8/2016 | Ramamurthy et al. |
| 9,414,783 B2 | 8/2016 | Verma |
| 2005/0216031 A1 | 9/2005 | Curtis et al. |
| 2013/0345739 A1 | 12/2013 | Brady et al. |
| 2015/0297864 A1 | 10/2015 | Kokish et al. |
| 2016/0235946 A1 | 8/2016 | Lewis et al. |
| 2016/0374702 A1* | 12/2016 | St. George ............ A61B 90/03 606/127 |
| 2017/0020541 A1* | 1/2017 | Mahajan ............... A61B 17/221 |
| 2017/0105743 A1 | 4/2017 | Vale et al. |
| 2018/0116685 A1 | 5/2018 | Ulm |
| 2018/0125513 A1 | 5/2018 | Dhindsa |
| 2018/0221035 A1 | 8/2018 | Chu |

* cited by examiner

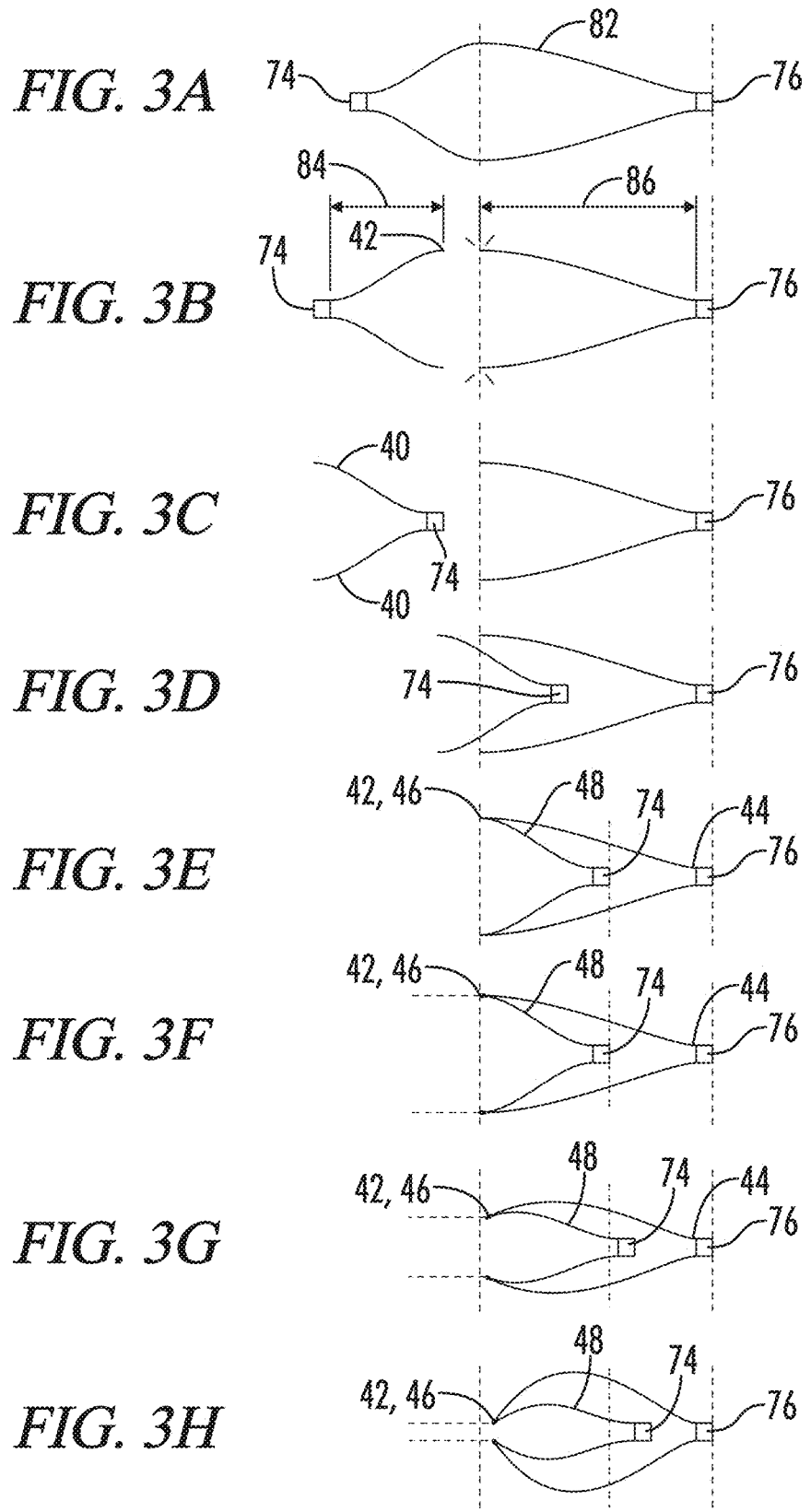

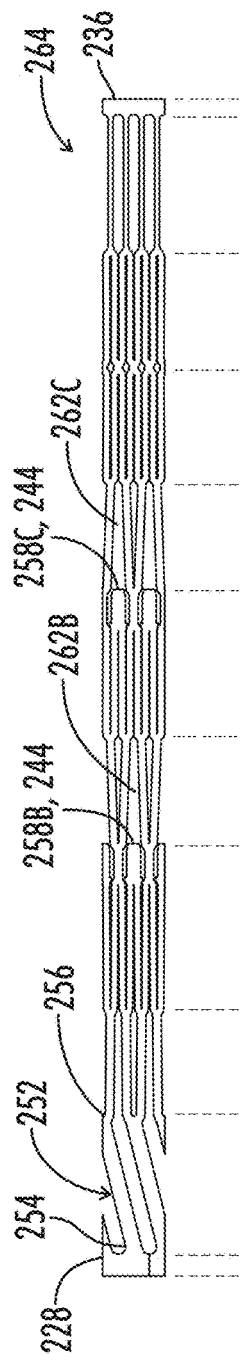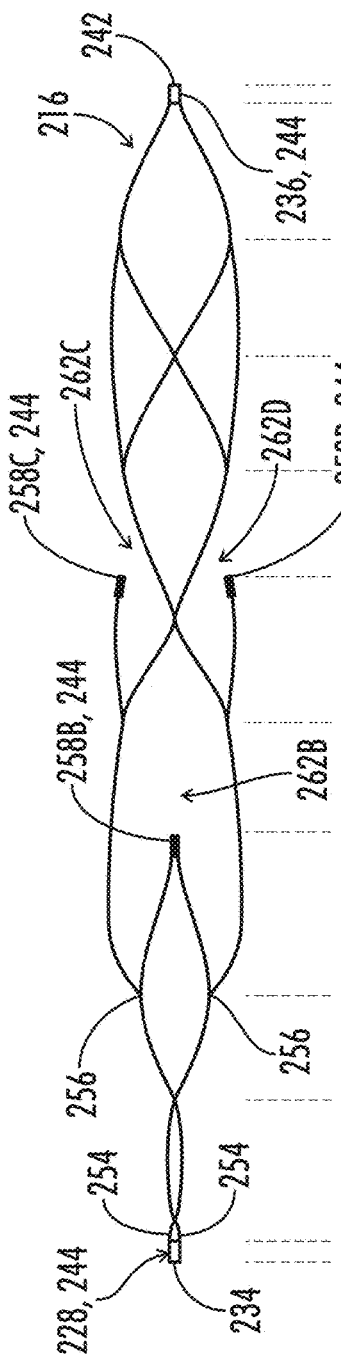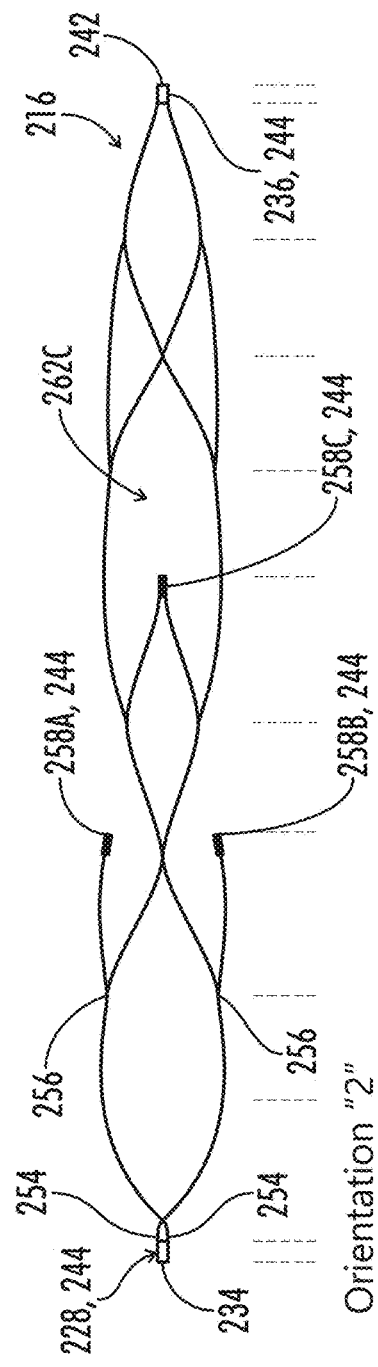

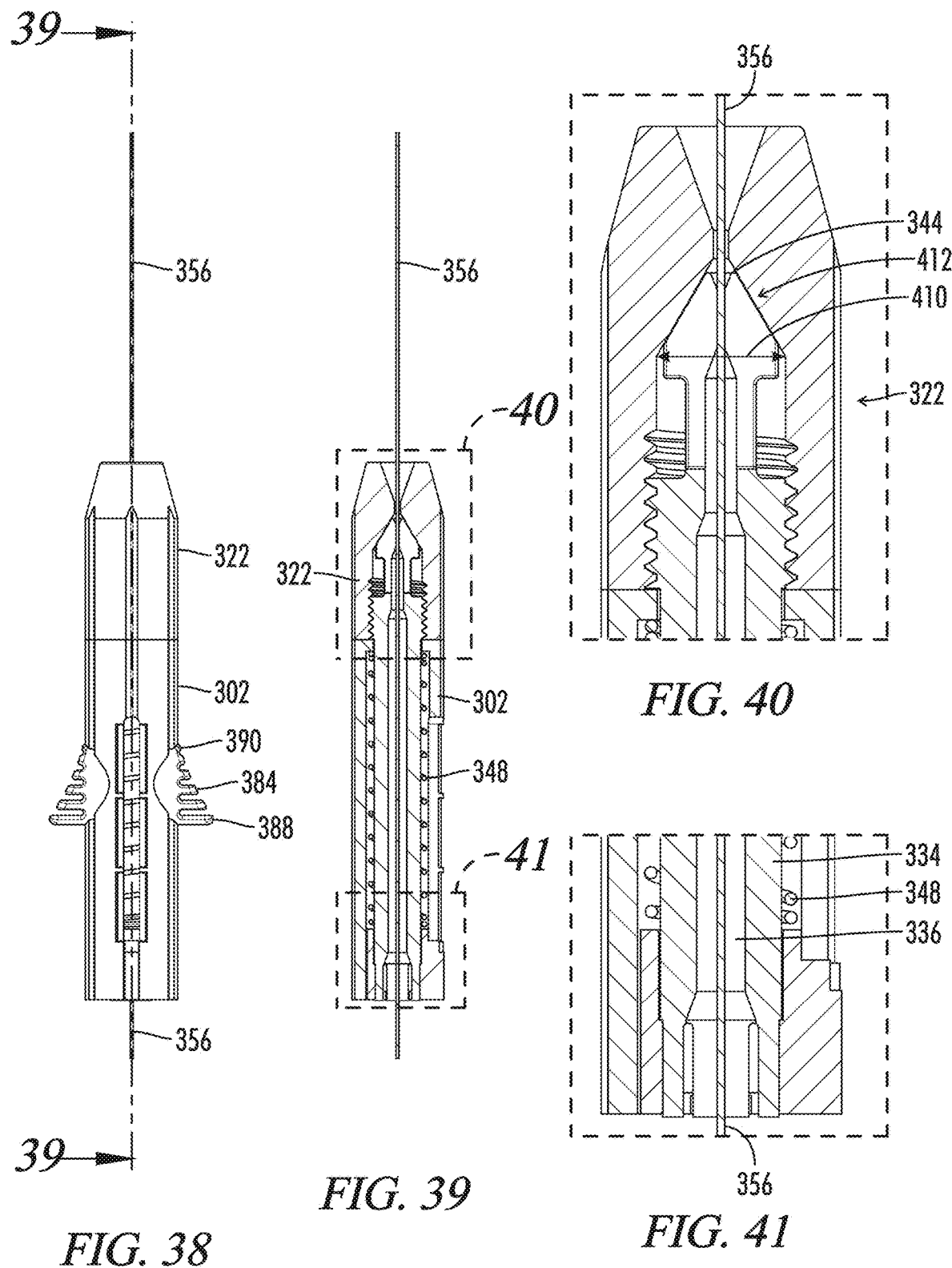

CLOT RETRIEVAL SYSTEM

RELATED APPLICATIONS

This application is a continuation-in-part of U.S. patent application Ser. No. 15/311,849, filed Nov. 16, 2016, which is a 371 application of international patent application PCT/US15/31447, filed May 18, 2015. International patent application PCT/US15/31447 claims the benefit of U.S. Provisional Application 61/994,919, filed May 18, 2014, U.S. Provisional Application 61/994,934, filed May 18, 2014. International patent application PCT/US15/31447 is a continuation-in-part of U.S. patent application Ser. No. 14/558,712 (now U.S. Pat. No. 9,155,552), filed Dec. 2, 2014, and U.S. patent application Ser. No. 14/558,705 (now U.S. Pat. No. 9,173,668). International patent application PCT/US15/31447 is also a continuation-in-part of International Patent Application PCT/US/2015010178, filed Jan. 5, 2015. The entire contents of the foregoing are incorporated herein by reference.

BACKGROUND

Technical Field

The present invention relates to a deployable system for removing a blood clot or other object from a lumen of an animal.

Background of the Invention

Acute ischemic strokes develop when a blood clot (thrombus) blocks an artery supplying blood to the brain. Needless to say, when a blood clot creates such a blockage, time in removing the clot is critical.

The removal of intracranial obstructions is limited by several factors, such as the distance of the intracranial obstruction from the femoral access site, the tortuosity (twists and turns in the artery as it enters the base of the skull) of the cervical and proximal intracranial vasculature, the small size of the vessels and the extremely thin walls of intracranial vessels, which lack a significant muscular layer. These limitations require a device to be small and flexible enough to navigate through tortuous vessels within a guide catheter and microcatheter, expand after delivery at the site of occlusion and be retrievable into the microcatheter and yet be strong enough to dislodge strongly adherent thrombus from the vessel wall. In addition, the device should distally entrap or encase the thrombus to prevent embolization to other vessels and to completely remove the occlusion. The device should be retrievable without the need for proximal occlusion of the vessel, which carries risk of further ischemia and risk of vessel injury. The device should be simple to use and be capable of multi-use within the same patient treatment. The device should not be abrasive and should not have sharp corners exposed to the endothelial layer of the vessel wall.

Currently available intravascular thrombus and foreign body removal devices lack several of these features. Currently available devices include the MERCI™ RETRIEVER clot retriever device marketed by Concentric Medical, Inc. (Mountainview, Calif.), the PENUMBRA™ system marketed by Penumbra Inc. (Alameda, Calif.) to retrieve clots, and the newer stent retrieval devices TREVO™ (Stryker, Kalamazoo, Mich.) and SOLITAIRE™ (eV3 Endovascular Inc., Plymouth, Mass., which is a subsidiary of Covidien). All the devices are ineffectual at removing organized hard thrombus that embolize to the brain from the heart and from atherosclerotic proximal vessels. These "hard" thrombi constitute the majority of strokes which are refractory to medical treatment and are therefore referred for removal by mechanical means through an endovascular approach. The MERCI retrieval system is comprised of coiled spring-like metal and associated suture material. The method of use is deployment distal to the thrombus and by withdrawing the device through the thrombus, the thrombus becomes entangled in the coil and mesh and then is retrieved. The MERCI system requires occlusion of the proximal vessel with a balloon catheter and simultaneous aspiration of blood while the thrombus is being removed. Most of the time, the device fails to dislodge the thrombus from the wall of the vessel and often, even when successfully dislodging the thrombus, the thrombus embolizes into another or the same vessel due to the open ended nature of the device.

The next attempt at a thrombus removal system was the PENUMBRA. The PENUMBRA is a suction catheter with a separator that macerates the thrombus which is then removed by suction. The device is ineffective at removing hard, organized thrombus which has embolized from the heart, cholesterol plaque from proximal feeding arteries and other foreign bodies.

The SOLITAIRE and TREVO systems are self-expanding non-detachable stents. The devices are delivered across the thrombus which is then supposed to become entwined in the mesh of the stent and which is then removed in a manner similar to the MERCI system. Again, these devices are ineffectual at treating hard thrombus. In fact, the thrombus is often compressed against the vessel wall by the stent which temporarily opens the vessel by outwardly pressing the clot against the vessel wall. Upon retrieval of the devices, the clot remains or is broken up into several pieces which embolize to vessels further along the vessel.

U.S. Pat. No. 4,890,611 teaches a device for shearing arteriosclerotic deposits. However, the device does not include a clamp for releasably engaging the pull wire.

Thus, there is a need for new, easy-to-use, easy-to-manufacture, safe surgical devices for removing obstructions, such as blood clots, from internal lumens of humans and other animals in a timely manner.

BRIEF SUMMARY

The present disclosure provides several systems for removing obstructions and other objects within a blood vessel or other lumen of an animal. The system may be deployed in the lumen from a distal end of a catheter and, in some embodiments, includes a pull wire having a proximal end and a distal end; a distal body attached to the pull wire, the distal body comprising an interior, an exterior, a proximal end, a distal end, a plurality of proximal memory metal strips located at the proximal end, a proximal hub located in the distal body interior, and a distal hub located distal relative to the proximal hub. The distal body has a relaxed state wherein the distal body has a first height and width and a collapsed state wherein the distal body has a second height and width, the second height less than said first height, the second width less than the first width. The system further includes a catheter having an interior, a proximal end leading to the interior and a distal end leading to the interior, the catheter comprised of a biocompatible material and configured to envelope the distal body when the distal body is in the collapsed state. Each of the proximal memory metal strips has a proximal end and a distal end and preferably, in the relaxed state, each of the proximal ends of the proximal memory metal strips is located proximal relative to the proximal hub. Preferably, in the relaxed state, the proximal ends of the proximal memory metal strips are configured to move towards each other and towards the pull wire when an operator moves the proximal hub distally and closer to the stationary distal hub (i.e., when the operator decreases the distance between the hubs). Preferably, in the relaxed state, the proximal ends of the proximal memory metal strips are configured to move away from each other and away from the pull wire by moving the proximal hub proximally away from the stationary distal hub (i.e., when the operator increases the distance between the hubs).

Optionally, the system further includes a plurality of memory metal connector strips, the plurality of memory metal connector strips each having a proximal end attached to a proximal memory metal strip and a distal end attached to the proximal hub. Optionally, the connector strips are integral with the proximal hub (i.e., optionally, the connector strips and the proximal hub are formed from the same piece of memory metal). Optionally, the proximal hub is a tube having an aperture and the pull wire passes through the aperture. Optionally, in the relaxed state, the proximal hub is slideable along the pull wire (i.e., at least a segment of the pull wire). Optionally, in the relaxed state, the proximal memory metal strips are distributed substantially evenly about a perimeter of the distal body. Optionally, the distal hub is a tube having an aperture. Optionally, the distal hub is attached to the pull wire such that the distal hub is not slideable along the pull wire. Optionally, the distal body further comprises a lead wire extending distally from the distal hub. Optionally, the distal body comprises a basket comprised of a plurality of memory metal strips distal relative to the proximal memory metal strips. Optionally, the distal hub, the proximal hub, and the distal basket are comprised of a nitinol having the same material composition. Optionally, the distal body further comprises an x-ray marker. Optionally, the proximal memory metal strips form a claw, the claw having a closeable proximal end formed by the proximal ends of the proximal memory metal strips. Optionally, between 2 and 4 proximal memory metal strips form the claw. Optionally, the distal body, in the relaxed state, has a tapered shape in which the distal body height and width decrease from the proximal end to the distal end. Optionally, the distal body, in the relaxed state, has a bullet shape. Optionally, the proximal hub and the distal hub are generally cylindrical in shape and each has an outer diameter and an inner diameter that forms the apertures of the proximal and distal hubs, the outer diameters of the proximal and distal hubs are substantially the same size, and the inner diameters of the proximal and distal hubs are substantially the same size. Optionally, the outer diameters of the proximal and distal hubs are from about 0.011 inches to about 0.054 inches, and the inner diameters of the proximal and distal hubs are from about 0.008 inches to about 0.051 inches. Optionally, the pull wire is generally cylindrical and the diameter of the pull wire is between about 0.008 inches and about 0.051 inches. Optionally, the proximal memory metal strips have a length of between about 10 and about 60 millimeters. Optionally, the first height and first width of the distal body are between about 2 millimeters (mm) and about 6 millimeters. Optionally, the proximal memory metal strips are configured to a separate clot from a blood vessel wall.

The present invention also provides a method of removing an object from an interior lumen of an animal, the lumen having an interior wall forming the lumen. In some embodiments, the method includes:

a) providing a system comprising: i) a pull wire having a proximal end and a distal end; ii) a distal body attached to the pull wire, the distal body comprising a proximal end, a distal end, and a claw, the claw comprised of a plurality of memory metal strips, the distal body having a relaxed state wherein the distal body has a first height and width and a collapsed state wherein the distal body has a second height and width, the second height less than said first height, the second width less than said first width; and iii) a catheter having an interior, a proximal end leading to the interior and a distal end leading to the interior, the catheter comprised of a biocompatible material and configured to envelope the distal body when said distal body is in said collapsed state;

b) positioning the system in the lumen;

c) deploying the distal body from the distal end of the catheter;

d) allowing the height and width of said distal body to increase; and e) moving the memory metal strips towards each other and the pull wire so as to capture the obstruction. Optionally, the claw and the memory metal strips are located at the proximal end of said distal body and the distal body is deployed distal to said object. Optionally, the proximal memory metal strips have a proximal end forming the proximal end of the claw and a distal end, and the method includes moving the proximal ends of the memory metal strips towards each other and the pull wire so as to capture the obstruction. Optionally, the distal body further comprises a proximal hub located in the distal body interior, and a distal hub located distal relative to the proximal hub, each of the memory metal strips has a proximal end and a distal end, each of the proximal ends of the memory metal strips is located proximal relative to the proximal hub, and the proximal ends of the memory metal strips are configured to move towards each other and towards the pull wire by moving the proximal hub distally and closer to the distal hub, and the proximal ends of the memory metal strips are configured to move away from each other and away from the pull wire by moving the proximal hub proximally and away from the distal hub, and the method further comprises moving the proximal hub distally and closer to the distal hub so as to capture the obstruction in the claw. Optionally, the interior lumen is an intracranial artery and the obstruction is a blood clot. Optionally, the method further comprises using the clot to move the proximal hub toward the distal hub and exert tension on the proximal memory metal strips. Optionally, the method further comprises using a tube to move the proximal hub toward the distal hub and exert tension on the proximal memory metal strips.

The present invention also provides a method of manufacturing a system for removing objects within an interior lumen of an animal. In some embodiments, the method includes: a)

providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;

b) cutting the wall of the middle portion with a laser;

c) removing the pieces of the middle portion cut by the laser to form a proximal tube, a middle portion comprising a plurality of memory metal strips attached to the proximal tube and a distal tube;

d) altering the shape of the middle portion;

e) allowing the middle portion to expand relative to the distal tube and the proximal tube;

f) cutting the memory metal strips to form a first segment comprising the proximal tube and a proximal segment of the memory metal strips, and a second segment comprising the distal tube and a distal segment of the memory metal strips; and g) joining the proximal segments to the distal segments such that the distal segments form the proximal end of a distal body, such that the proximal tube is located inside an interior of said distal body, and such that the proximal tube is located distal relative to the proximal end.

Optionally, the method further includes placing a pull wire through the proximal tube such that the proximal tube is slideable along at least a segment of the pull wire. Optionally, the method further includes attaching the pull wire to the distal tube. Optionally, the step of joining the proximal segments to the distal segments comprises welding the proximal segments to the distal segments. Optionally, after the step of joining the proximal segments to the distal segments, the proximal end forms a claw comprised of between 2 and 4 memory metal strips, the claw memory metal strips configured to move towards each by moving said proximal tube distally and closer to the distal tube, and the claw memory metal strips configured to move away from each other by moving the proximal tube proximally and away from said distal tube. Optionally, the method further includes not altering the shape of the proximal and distal portions while altering the shape of the middle portion. Optionally, the method further includes cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches.

In an alternate embodiment, the present disclosure provides a system for removing objects from an interior lumen of an animal that includes:

a pull wire having a proximal end and a distal end;

a distal body attached to the pull wire, the distal body comprising an interior, a proximal end, a distal end, a distal body length extending from the proximal end to the distal end, a proximal hub (preferably in the form of a tube) forming the proximal end of the distal body, a basket comprised of a plurality of cells formed by a plurality of basket strips, a plurality of proximal strips, and, optionally a distal hub (preferably in the form of a tube) forming a distal end of the basket, the basket comprising a basket interior, each proximal strip having a proximal end attached to the proximal hub, and a distal end attached to a cell, the distal body having a relaxed state wherein the distal body has a first height and a first width, and a collapsed state wherein the distal body has a second height and a second width, the second height less than the first height, the second width less than the first width; and a catheter having an interior, a proximal end leading to the interior and a distal end leading to the interior, the catheter comprised of a biocompatible material and configured to envelope the distal body when the distal body is in the collapsed state, wherein, in the relaxed state, the basket comprises a first pair of distal crowns not attached to another cell of the basket and pointing generally in the distal direction, the first pair of distal crowns located approximately the same distance from the proximal hub and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub and further wherein each of the distal crowns in the first and second pair of distal crowns comprises an x-ray marker, the x-ray maker more visible under x-ray as compared to the basket strips when the distal body is located in a cranial blood vessel inside the body of a human and the x-ray is taken from outside the human's body. When it is said that the first pair of distal crowns are located approximately the same distance from the proximal hub, it will be understood that if one of the first pair of distal crowns is located X distance from the proximal hub, the other of the first pair of distal crowns is located X distance plus or minus (+/−) 3 mm from the proximal hub, more preferably X distance plus or minus (+/−) 0.5 mm from the proximal hub. Similarly, when it is said that the second pair of distal crowns are located approximately the same distance from the proximal hub, it will be understood that if one of the second pair of distal crowns is located Y distance from the proximal hub, the other of the first pair of distal crowns is located Y distance plus or minus (+/−) 3 mm from the proximal hub, more preferably Y distance plus or minus (+/−) 0.5 mm from the proximal hub. Optionally, instead of a distal hub, the basket includes an open distal end.

Optionally, the x-ray markers are comprised of a material different than the material forming the basket strips. Optionally, in the relaxed state, the basket interior is substantially hollow. Optionally, in the relaxed state, the distal body does not have another x-ray marker that is located approximately the same distance from the proximal hub as the first pair of x-ray markers and the distal body does not have another x-ray marker that is located approximately the same distance from the proximal hub as the second pair of x-ray markers. In other words, the first and second pair of x-ray markers are the only markers their respective distances from the proximal hub. Optionally, each distal crown in the first and second pair of distal crowns forms part of an enlarged cell and further wherein the surface area of each enlarged cell in the relaxed state is greater than the surface area of each of the other individual cells of the basket and further wherein the enlarged cells are configured to allow a thrombus to pass therethrough and into the basket interior. Optionally, in the relaxed state, the distal body does not have another free distal-pointing crown that is located approximately the same distance from the proximal hub as the first pair of distal crowns and the distal body does not have another free distal-pointing crown that is located approximately the same distance from the proximal hub as the second pair of distal crowns. Optionally, the basket strips are comprised of a memory metal. Optionally, each of the distal crowns in the first pair and second pair of distal crowns curve radially inward toward the basket interior in the relaxed state, wherein the distal crowns of the first pair of distal crowns are configured to contact each other when an exterior, external compressive force (such as a thrombus) is exerted on a distal crown of the first pair of distal crowns when the distal body is in the relaxed state, and further wherein the distal crowns of the second pair of distal crowns are configured to contact each other when an exterior, external compressive force (such as a thrombus) is exerted on a distal crown of the second pair of distal crowns when the distal body is in the relaxed state. Optionally, the proximal hub is located approximately in the center of the first height and first width in the relaxed state. For example, preferably the proximal hub is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub (e.g., within about 0 and about 4 mm of the proximal hub). Optionally, each distal crown forms part of a cell that further comprises a proximal crown pointing generally in the proximal direction and connected to a memory metal strip (e.g., a proximal strip comprised of a memory metal or a basket strip comprised of a memory metal). In other words, the proximal crowns are not free. Optionally, the basket, the proximal hub and the proximal strips are comprised of a memory metal, wherein the proximal hub comprises a proximal end and a distal end, and further wherein the proximal strips are integral with the distal end of the proximal hub. Optionally, the length of the distal body from the proximal hub to the distal hub (not including any lead wire) is from about 20 mm to about 65 mm. Optionally, the system is used in a method of removing a blood clot from a blood vessel of an animal the method comprising the steps of:

a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles. Optionally, at least one x-ray marker attached to the distal crowns is distal to the clot when the distal body is deployed from the distal end of the catheter. Optionally, the method further comprises applying contrast dye proximally and distally to the clot. Optionally, the method further comprises providing a suction catheter having a proximal end and a distal end, and attaching the distal end of the suction catheter to the clot by applying suction to the suction catheter. Optionally, the method further comprises aspirating by hand a pre-determined volume of fluid from the suction catheter using a syringe and then locking the syringe at the pre-determined volume. Optionally, the method further comprises delivering the suction catheter adjacent to the clot by advancing the catheter over the pull wire.

In yet another embodiment, the system includes:
a pull wire having a proximal end and a distal end;
a distal body attached to the pull wire, the distal body comprising an interior, a proximal end, a distal end, a distal body length extending from the proximal end to the distal end, a proximal hub (preferably in the form of a tube) forming the proximal end of the distal body, a basket comprised of a plurality of cells formed by a plurality of basket strips, a plurality of proximal strips, and optionally a distal hub (preferably in the form of a tube) forming a distal end of the basket, the basket comprising a basket interior, each proximal strip having a proximal end attached to the proximal hub, and a distal end attached to a cell, the distal body having a relaxed state wherein the distal body has a first height and a first width, and a collapsed state wherein the distal body has a second height and a second width, the second height less than the first height, the second width less than the first width; and
a catheter having an interior, a proximal end leading to the interior and a distal end leading to the interior, the catheter comprised of a biocompatible material and configured to envelope the distal body when the distal body is in the collapsed state,
wherein, in the relaxed state, the basket comprises a first pair of distal crowns not attached to another cell of the basket and pointing generally in the distal direction, the first pair of distal crowns located approximately the same distance from the proximal hub and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub, wherein each distal crown of the first and second pair of distal crowns form a cell, each cell further comprising a proximal crown pointing generally in the proximal direction and connected to a memory metal strip, wherein each of the distal crowns in the first pair and second pair of distal crowns curve radially inward toward the basket interior in the relaxed state, wherein the distal crowns of the first pair of distal crowns are configured to contact each other when an exterior, external compressive force (e.g., a thrombus) is exerted on a distal crown of the first pair of distal crowns when the distal body is in the relaxed state, and further wherein the distal crowns of the second pair of distal crowns are configured to contact each other when an exterior, external compressive force (e.g., a thrombus) is exerted on a distal crown of the second pair of distal crowns when the distal body is in the relaxed state. When it is said that a proximal crown pointing generally in the proximal direction and is connected to a memory metal strip, it is meant that the proximal crown is either connected to a basket strip or a proximal strip comprised of a memory metal (e.g., nitinol). When it is said that the first pair of distal crowns are located approximately the same distance from the proximal hub, it will be understood that if one of the first pair of distal crowns is located X distance from the proximal hub, the other of the first pair of distal crowns is located X distance plus or minus (+/−) 0.5 mm from the proximal hub. Similarly, when it is said that the second pair of distal crowns are located approximately the same distance from the proximal hub, it will be understood that if one of the second pair of distal crowns is located Y distance from the proximal hub, the other of the first pair of distal crowns is located Y distance plus or minus (+/−) 0.5 mm from the proximal hub. Optionally, instead of a distal hub, the basket includes an open distal end.

Optionally, the proximal hub is located approximately in the center of the first height and first width in the relaxed state. For example, preferably the proximal hub is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, in the relaxed state, the basket interior is substantially hollow. Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub (e.g., within about 0 mm and about 4 mm of the proximal hub). Optionally, each distal crown in the first and second pair of distal crowns forms part of an enlarged cell and further wherein the surface area of each enlarged cell in the relaxed state is at least twice as large as the surface area of each other individual cell of the basket and further wherein the enlarged cells are configured to allow a thrombus to pass therethrough and into the basket interior. Optionally, the pull wire is attached to the proximal hub. Optionally, the basket, the proximal hub and the proximal strips are comprised of a memory metal, wherein the proximal hub comprises a proximal end and a distal end, and further wherein the proximal strips are integral with the distal end of the proximal hub. Optionally, the distal body further comprises a lead wire extending distally from the distal hub, the lead wire having a length of from about 3 mm to about 10 mm. Optionally, the distal hub, the proximal hub, and the basket are comprised of a nitinol having the same material composition and further wherein the proximal and the distal hubs are tubular and generally cylindrical in shape and each has an outer diameter and an inner diameter, the inner diameter forming apertures of the proximal and distal hubs and further wherein the outer diameters of the proximal and distal hubs are substantially the same size and further wherein the inner diameters of the proximal and distal hubs are substantially the same size. Optionally, the length of the distal body from the proximal hub to the distal hub (not including any lead wire) is from about 20 mm to about 65 mm.

Optionally, the system is used in a method of removing a blood clot from a blood vessel of an animal the method comprising the steps of:
a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles.

In still further embodiments, the present disclosure provides a system for removing a blood clot from a human blood vessel. The system may include a proximal outer tube comprising a proximal outer tube exterior comprising a slot, a proximal outer tube interior that may be hollow, a proximal outer tube proximal end that may be open, a proximal outer tube distal end that may be open, and a proximal outer tube length extending from the proximal outer tube proximal end to the proximal outer tube distal end. Optionally, the slot comprises a slot proximal end, a slot distal end, and a slot length extending from the slot proximal end to the slot distal end and parallel to the proximal outer tube length. Optionally, the system further includes a distal outer tube comprising a distal outer tube exterior, a distal outer tube interior that may be hollow, a distal outer tube proximal end that may be open and located distal to the proximal outer tube distal end, a distal outer tube distal end that may be open, a distal outer tube length extending from the distal outer tube proximal end to the distal outer tube distal end. Optionally, the distal outer tube is not attached to the proximal outer tube. Optionally, the system further includes an inner tube extending from the proximal outer tube interior to the distal outer tube interior. Optionally, the inner tube comprises an inner tube interior that may be hollow, an inner tube exterior comprising a fin (which is positioned in the proximal outer tube slot), an inner tube proximal end that may be open, an inner tube distal end that may be open and an inner tube length extending from the inner tube proximal end to the inner tube distal end. Optionally, the system further includes a compressible spring having a spring proximal end, a spring distal end, and a spring length extending from the spring proximal end to the spring distal end. Optionally, the system further includes a pull wire extending through at least the distal outer tube distal end (and optionally, the distal outer tube proximal end, the inner tube distal end, the inner tube interior, the inner tube distal end, the proximal outer tube proximal end, the proximal outer tube interior and/or the proximal outer tube distal end), the pull wire having a pull wire proximal end (optionally located proximal to the proximal outer tube proximal end) and a pull wire distal end located distal to the distal outer tube distal end. Optionally, the system further includes a distal body located distal to the distal outer tube and comprising a distal body interior, a distal body perimeter, a distal body proximal end connected to the pull wire, a distal body distal end, a distal body length extending from the distal body proximal end to the distal body distal end, and a distal body height and width perpendicular to the distal body length. Optionally, the distal body comprises a framework formed by a plurality of memory metal strips. Optionally, the distal body has a relaxed state wherein the distal body has a first height and a first width, and a collapsed state wherein the distal body has a second height and a second width, the second height of the distal body less than the first height of the distal body, the second width of the distal body less than the first width of the distal body. Optionally, at least one of the distal outer tube and the inner tube (preferably, the inner tube distal end) comprises a clamp having a closed position in which the clamp closes around the pull wire and an open position in which the clamp is open with respect to the pull wire. Optionally, when the clamp is in the open and closed position, the inner tube is attached to the distal outer tube and moves along with the distal outer tube in the lengthwise direction. Optionally, at least when the clamp is in the closed position, the proximal outer tube is configured to move proximally for a pre-determined distance relative to the inner tube, distal outer tube, the pull wire and the distal body in the lengthwise direction. Optionally, at least when the clamp is in the closed position, moving the proximal outer tube proximally relative to the distal outer tube, the inner tube, the pull wire and the distal body causes the proximal outer tube slot to move proximally relative to the fin and causes the spring to move from a relaxed length to a compressed length. Optionally, when the clamp is in the closed position, rotating the proximal outer tube about the proximal outer tube length in a clockwise and counterclockwise direction is configured to rotate the distal outer tube, the pull wire and the distal body. Optionally, when the clamp is in the open position, rotating the proximal outer tube about the proximal outer tube length in a clockwise and counterclockwise direction is configured to rotate the distal outer tube but neither the pull wire nor the distal body. Optionally, when the clamp is in the open position, the proximal outer tube is configured to move proximally for a pre-determined distance relative to at least the inner tube and the distal outer tube in the lengthwise direction. Optionally, the system comprises a relaxed position in which the proximal outer tube distal end abuts against the distal outer tube proximal end and in which the spring is the relaxed length and a second position in which the distal end of the proximal outer tube does not abut the proximal end of the distal outer tube and in which the spring is the compressed length. Optionally, the proximal outer tube exterior comprises indicia adjacent to the slot. Optionally, the proximal outer tube exterior comprises two handle flanges comprising grooves located on opposite sides of the proximal outer tube exterior. Optionally, the handle flanges have a proximal end and a distal end and further wherein the handle flanges extend laterally from the proximal outer tube to a greater extent at the proximal end of the handle flanges as compared to the distal end of the handle flanges. Optionally, the inner tube comprises an inner tube height and an inner tube width, and further wherein the inner tube distal end comprises a tapered portion in which the inner tube height and width decrease at the inner tube distal end. Optionally, the distal outer tube interior and the inner tube comprise mating threads, wherein moving the inner tube threads along the distal outer tube interior threads in a first direction moves the clamp to the closed position and further wherein moving the inner tube threads along the distal outer tube interior threads in a second direction moves the clamp to the open position. Optionally, the slot proximal end is at the proximal end of the proximal outer tube. Optionally, the inner tube is comprised of a rod and a collar enveloping the rod and the collar comprises the fin. Optionally, the slot length is less than the proximal outer tube length.

In still further embodiments, the present disclosure provides a method of removing a blood clot from a blood vessel of a human the method comprising the steps of: a) providing the system; b) positioning a catheter comprising the distal body in the blood vessel; c) deploying the distal body from the catheter and allowing the height and width of the distal body to increase; d) capturing the blood clot with the distal body; and e) moving the distal body proximally out of the blood vessel by grasping and pulling proximally on the proximal outer tube. Optionally, the system further comprises the steps of moving the clamp from the open position to the closed position rotating the distal body in the blood vessel by rotating the proximal outer tube at least before step d).

In still further embodiments, the present disclosure provides a method of removing a blood clot from a blood vessel of a human the method comprising the steps of a) providing a gauge system that may include i) a pull wire having a proximal end and a distal end; ii) a distal body that may comprises a distal body interior, a distal body perimeter, a distal body proximal end connected to the pull wire, a distal body distal end, a distal body length extending from the distal body proximal end to the distal body distal end, and a distal body height and width perpendicular to the distal body length, the distal body may comprise a framework formed by a plurality of memory metal strips, the distal body may have a relaxed state wherein the distal body has a first height and a first width, and a collapsed state wherein the distal body has a second height and a second width, the second height of the distal body less than the first height of the distal body, the second width of the distal body less than the first width of the distal body; and iii) a strain gauge that may be configured to measure tension placed on the pull wire, the strain gauge may be comprised of a tube, indicia and a clamp configured to releasably engage the pull wire; b) positioning a catheter comprising the distal body in the blood vessel; c) deploying the distal body from the catheter and allowing the height and width of the distal body to increase; d) capturing the blood clot with the distal body; and e) moving the distal body proximally out of the blood vessel by pulling proximally on the strain gauge.

The two above aforementioned methods may utilize any feature mentioned above with respect to the systems that include a distal outer tube, a proximal outer tube and an inner tube, including movement and rotation of the respective parts.

BRIEF DESCRIPTION OF THE DRAWINGS

in FIG. 2A, the tube is shown as though it were flat for purposes of illustrating the cut pattern only.

in FIG. 2C, the tube is rotated as compared to FIG. 2B.

FIGS. 3A-3H illustrate a method of manufacturing a distal body of one embodiment of the present invention using the laser cut memory metal tube of FIGS. 1 and 2; in FIGS. 3A-3H, the basket portion of the distal body is not shown for simplicity of illustration.

in FIGS. 4A-4D, the basket portion of the distal body is not shown for simplicity of illustration.

in FIG. 8, the basket portion of the distal body is not shown for simplicity of illustration.

in FIG. 9, the basket portion of the distal body is not shown for simplicity of illustration.

in FIG. 10, the basket portion of the distal body is not shown for simplicity of illustration.

FIG. 20A illustrates a view of a native memory metal tube used to manufacture a distal body of yet another embodiment of the present invention; the native tube has been rolled out flat, the lines in the tube indicate where the tube has been cut by a laser, and the distal body of FIGS. 20A-20C is slightly shorter than the distal body of FIGS. 11-19 and is meant for use in tortuous blood vessels.

FIG. 20B illustrates a first, perspective view of the distal body manufactured from the native tube of FIG. 20A; the distal body is in Orientation 1.

FIG. 20C illustrates a second, perspective view of the distal body manufactured from the native tube of FIG. 20A; the distal body is in Orientation 2.

in FIG. 26, the user has locked the syringe lever at the desired volume.

in FIG. 27, the suction catheter has partially sucked the distal body and clot into the suction catheter.

in FIG. 28, the suction catheter has completely sucked the distal body and clot into the suction catheter.

in FIG. 32A, the proximal outer tube distal end abuts the distal outer tube proximal end.

in FIG. 33A, the proximal outer tube distal end does not abut the distal outer tube proximal end.

in FIG. 34A, the proximal outer tube distal end does not abut the distal outer tube proximal end, and as compared to FIG. 33A, the fin in FIG. 34A is located more distally relative to the proximal outer tube proximal end, indicating more tension is on the pull wire.

in FIG. 35A, the proximal outer tube distal end does not abut the distal outer tube proximal end, and as compared to FIGS. 33A and 34A, the fin in FIG. 35A is located more distally relative to the proximal outer tube proximal end, indicating more tension is on the pull wire.

in FIG. 36, the inner tube is exploded from the distal outer tube.

FIG. 38 illustrates a top plan view of the strain gauge and pull wire of FIG. 32A; in FIG. 38, the proximal outer tube distal end abuts the distal outer tube proximal end.

FIG. 39 illustrates a top sectional view of the strain gauge and pull wire of FIG. 38 taken along line 39-39 of FIG. 38.

FIG. 40 illustrates a top sectional view of the boxed area labelled 40 in FIG. 39.

FIG. 41 illustrates a top sectional view of the boxed area labelled 41 in FIG. 39.

in FIG. 42, the proximal outer tube distal end does not abut the distal outer tube proximal end.

in FIG. 43, the proximal outer tube distal end does not abut the distal outer tube proximal end.

DETAILED DESCRIPTION

Figure 1A:
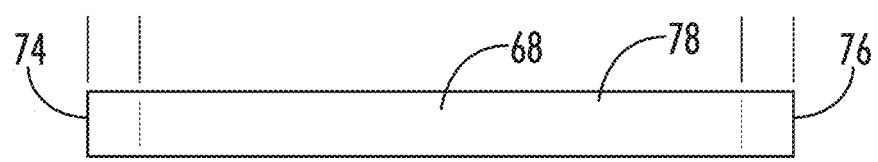
FIG. 1A illustrates a side, elevation view of a memory metal tube prior to being cut by a laser.
Figure 1B:
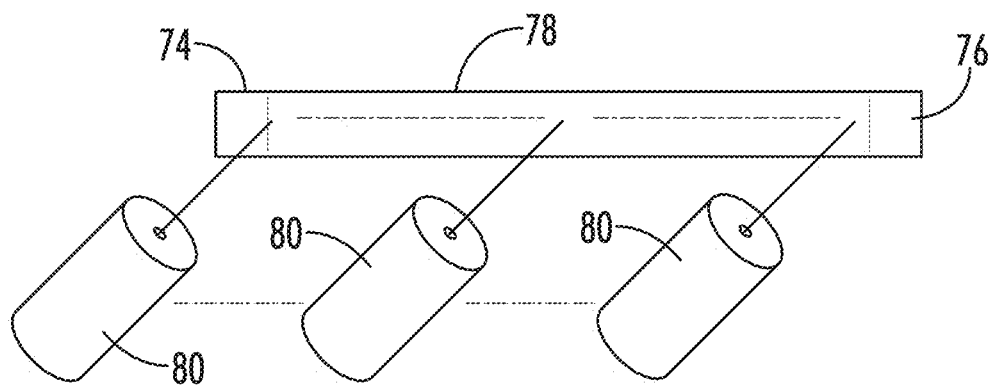
FIG. 1B illustrates a side, elevation view of the memory metal tube of FIG. 1A being cut by a laser.

With reference to FIGS. 1-10, the present disclosure provides a deployable system, generally designated by the numeral 10, for removing an obstruction such as a blood clot 12 or other object from a blood vessel 14 or other interior lumen of an animal. In addition to a blood clot 12, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

Referring further to FIGS. 1-10, the deployable system 10 includes a pull wire 16 that has a proximal end (not shown) and a distal end 0. Optionally, the diameter of the pull wire is between about 0.008 inches and about 0.051 inches. Preferably, the pull wire 16 is comprised of a biocompatible metallic material.

The system 10 further includes a distal body 22, which is attached to the pull wire 16. The distal body 22 has a proximal end 24, a distal end 26, an interior 28, and an exterior 30. The distal body 22 has a collapsed state, wherein the distal body 22 has a first height and width and is configured to fit into a catheter 50 (see FIG. 10A), and a relaxed state wherein the distal body 22 has a different height 32 and width and is configured to expand to about the height and width of a human blood vessel 14 when the distal body 22 is deployed from the catheter 50 (see FIGS. 10B-G). The distal body 22 further includes a proximal hub 74 and a distal hub 76 that is located distal relative to the proximal hub 74. In some embodiments, the distal body 22 includes a plurality of strips 40 comprised of a memory metal (e.g., a memory metal alloy such as nitinol) that form the proximal end 24 of the distal body 22. Optionally, the proximal memory metal strips 40 each have a distal end 44 and a proximal end 42 that forms an openable and closeable claw 46. Optionally, the proximal memory metal strips 40 are attached to the proximal hub 74 through connector memory metal strips 48. In such embodiments, the proximal hub 74 may be slideable along at least a segment of the pull wire 16, in contrast to the distal hub 76, which is optionally fixed to the pull wire 16 and not slideable along the pull wire 16. Moving the proximal hub 74 distally and closer to the distal hub 76 (i.e., shortening the distance 88 between the proximal hub 74 and distal hub 76 by moving the proximal hub 74 distally while keeping the distal hub 76 stationary) exerts tension on the connector memory metal strips 48 and, in turn, the proximal memory metal strips 40. This tension, in turn, causes the proximal ends 42 of the proximal memory metal strips 40 to move radially toward each other and the pull wire 16. As the proximal ends 42 of the proximal memory metal strips 40 move radially toward each other and the pull wire 16, the claw 46 (formed by the proximal memory metal strips 40) is brought from the open position to at least a partially closed position, which in turn, separates the obstruction 12 from the wall of the human lumen 14 and captures the obstruction 12. See FIG. 3H, FIG. 8, FIG. 9F, and FIGS. 10F and 10G. Conversely, preferably, movement of the proximal hub 74 proximally and away from the distal hub 76 (i.e., increasing the distance 88 between the hubs 74 and 76) releases the tension in the proximal memory metal strips 40, which in turn, causes the proximal ends 42 of the proximal memory metal strips 40 to move away from each other and the pull wire 16, opening the claw 46. The claw 46 and proximal hub 74 form several functions. First, as described, closing of the claw 46 captures the obstruction 12. Second, closing the claw 46 retracts the claw 46 from the wall of the lumen 14 so that the claw 46 does not scrape against (and damage) the lumen wall while capturing the obstruction 12. Third, closing the claw 46 reduces the height and width of the distal body 22, which allows the distal body 22 to be re-sheathed in the catheter 50, which may be desired, for example, if the operator seeks to re-deploy the distal body 22 in another location in the body (which may be the case if the operator originally deploys the distal body 22 in the wrong location in the lumen 14). For purposes of the present invention, "closing the claw" embraces both partially closing the claw 46 (where the proximal ends 42 of the proximal memory metal strips 40 do not contact the pull wire 16) and fully closing the claw 46 (where the proximal ends 42 contact the pull wire 16).

The claw 46 may be comprised of any number of proximal memory metal strips 40. Preferably, however, between 2 and 4 proximal memory metal strips 40 comprise the claw 46 (it being understood that the connector strips 48, if present, merely serve to tether the claw 46 to the proximal hub 74). Preferably, the proximal memory metal strips 40 have a length of between about 10 and about 60 millimeters. The proximal memory metal strips 40 can be thought of as arms of the claw 46.

In some embodiments, the connector strips 48 are integral with the proximal hub 74 (i.e., formed from the same piece of memory metal). In other embodiments, the proximal hub 74 may be welded to the connector strips 48. Optionally, in the relaxed state, the proximal memory metal strips 42 are distributed substantially evenly about a perimeter of the distal body 22.

Optionally, the distal body 22 includes a lead wire 52 extending distally from the distal body 22. Optionally, the lead wire 52 extends distally from the distal hub 76. If present, the lead wire 52 may be used to facilitate movement of the system 10 in the lumen 14.

Figure 2A:
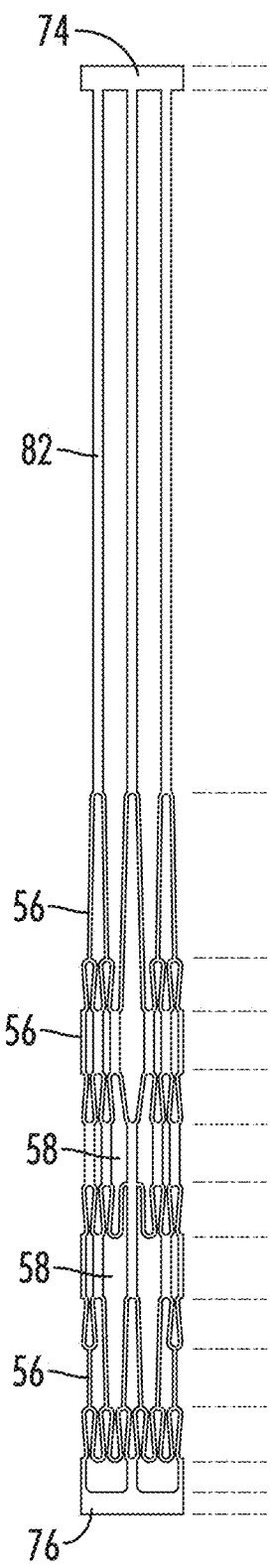
FIG. 2A illustrates a side, elevation view of the memory metal tube of FIG. 1B after being cut by a laser.
Figure 2B:
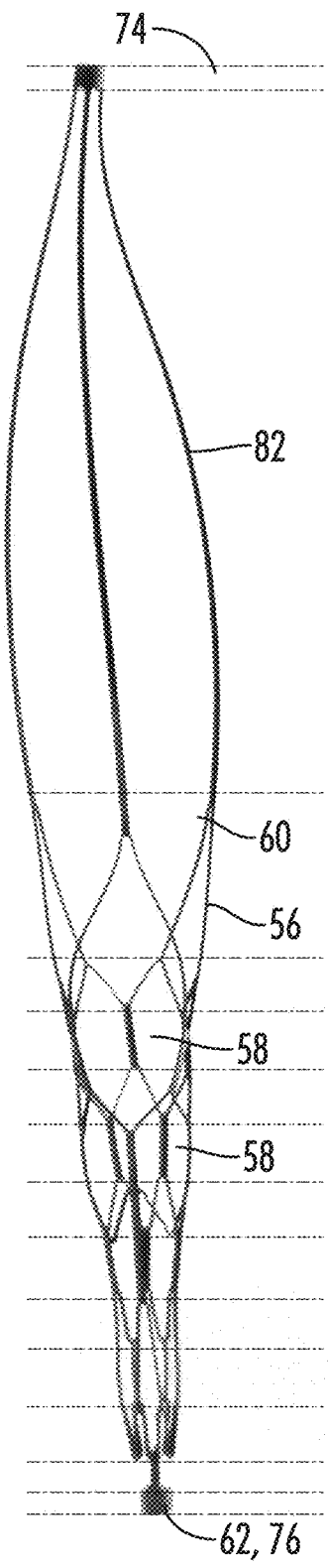
FIG. 2B illustrates a side, perspective view of the memory metal tube of FIG. 1B after being cut by a laser.
Figure 2C:
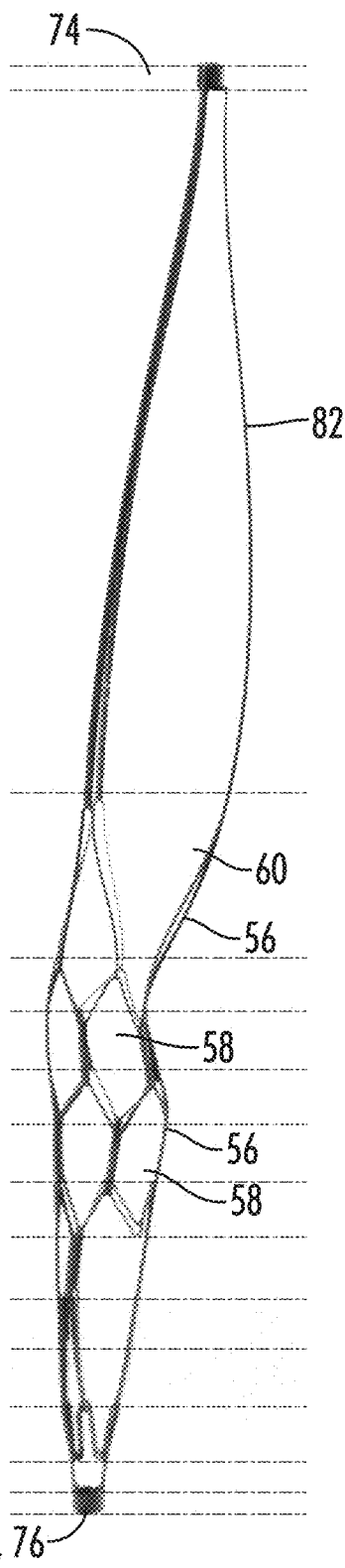
FIG. 2C illustrates another side, perspective view of the memory metal tube of FIG. 1B after being cut by a laser.
Figure 4A:
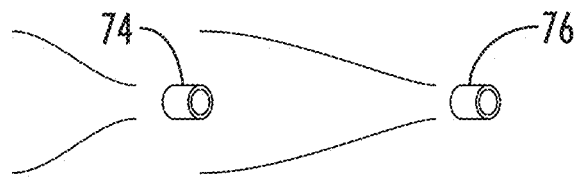
FIGS. 4A-4D illustrate the welding steps of the method of manufacturing shown in FIG. 3.
Figure 4B:
Figure 4C:
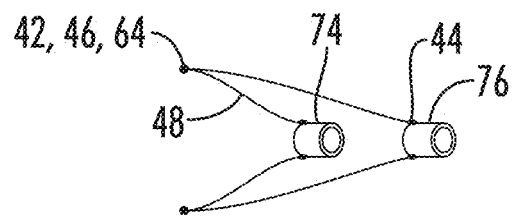
Figure 4D:
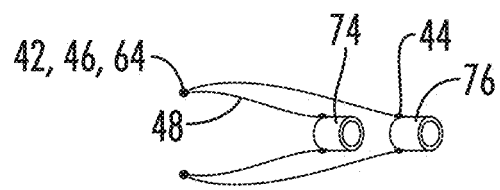
Figure 5:
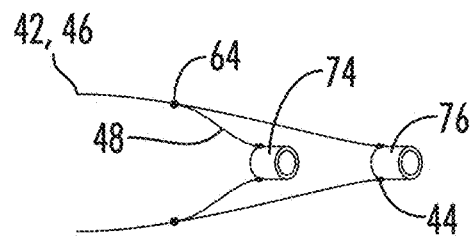
FIGS. 5 and 6 illustrate different locations that connector strips may be welded to the proximal memory metal strips.
Figure 6:
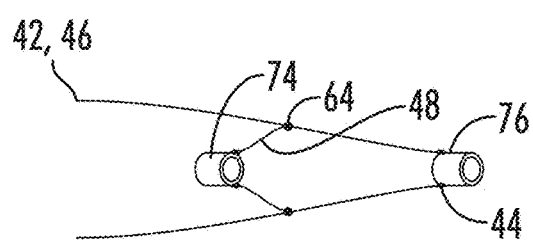
Figure 7:
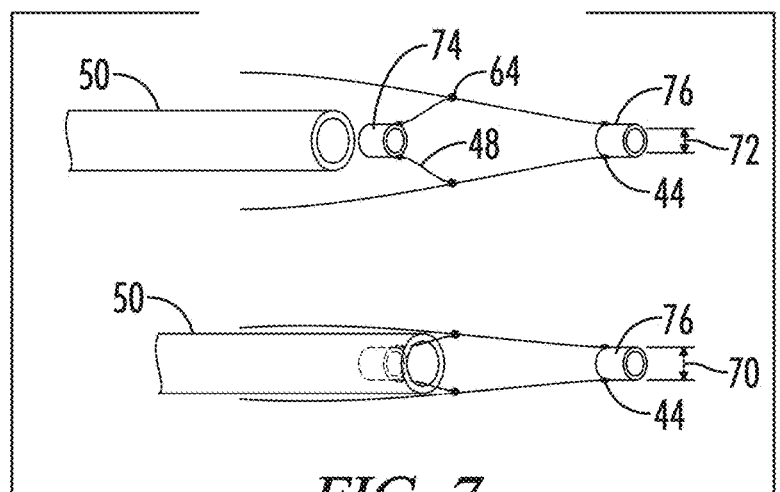
FIG. 7 illustrates a side, elevation view of a catheter and the distal body of FIG. 6.
Figure 8:
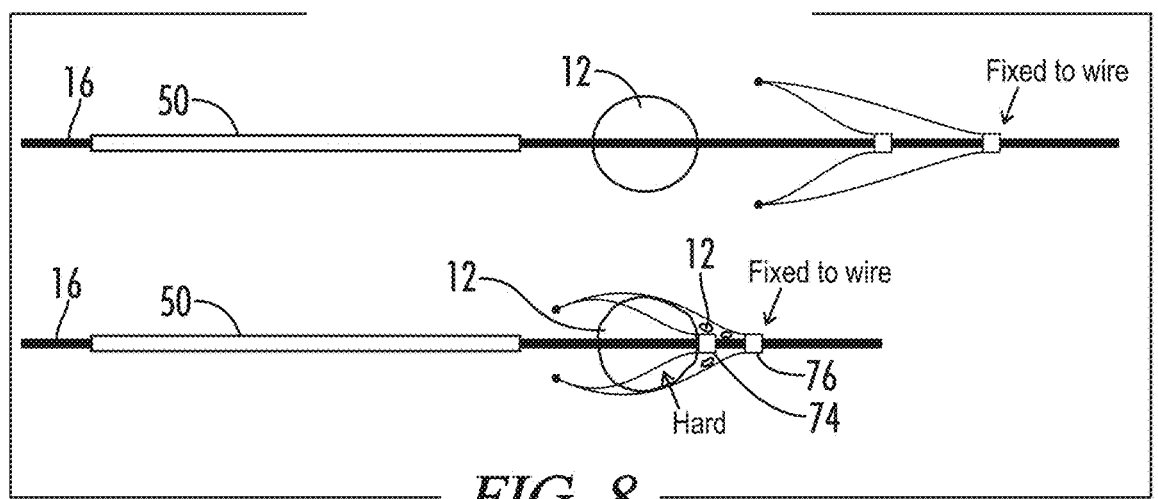
FIG. 8 illustrates a side, elevation view of a deployable system of one embodiment of the present invention being used to capture a blood clot.
Figure 9:
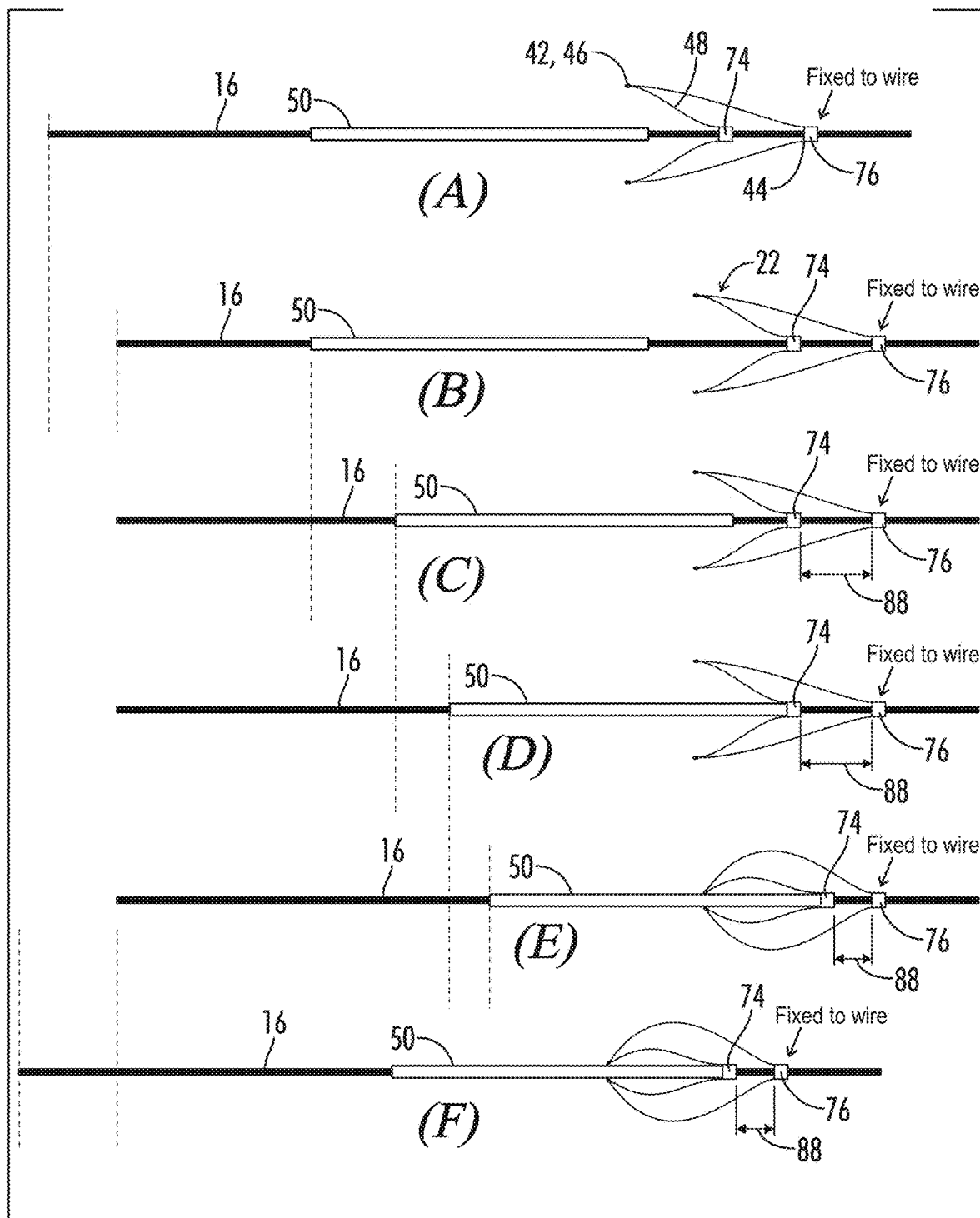
FIG. 9 illustrates a side, elevation view of a claw of one embodiment of the present invention being closed by a claw actuator tube.
Figure 10:
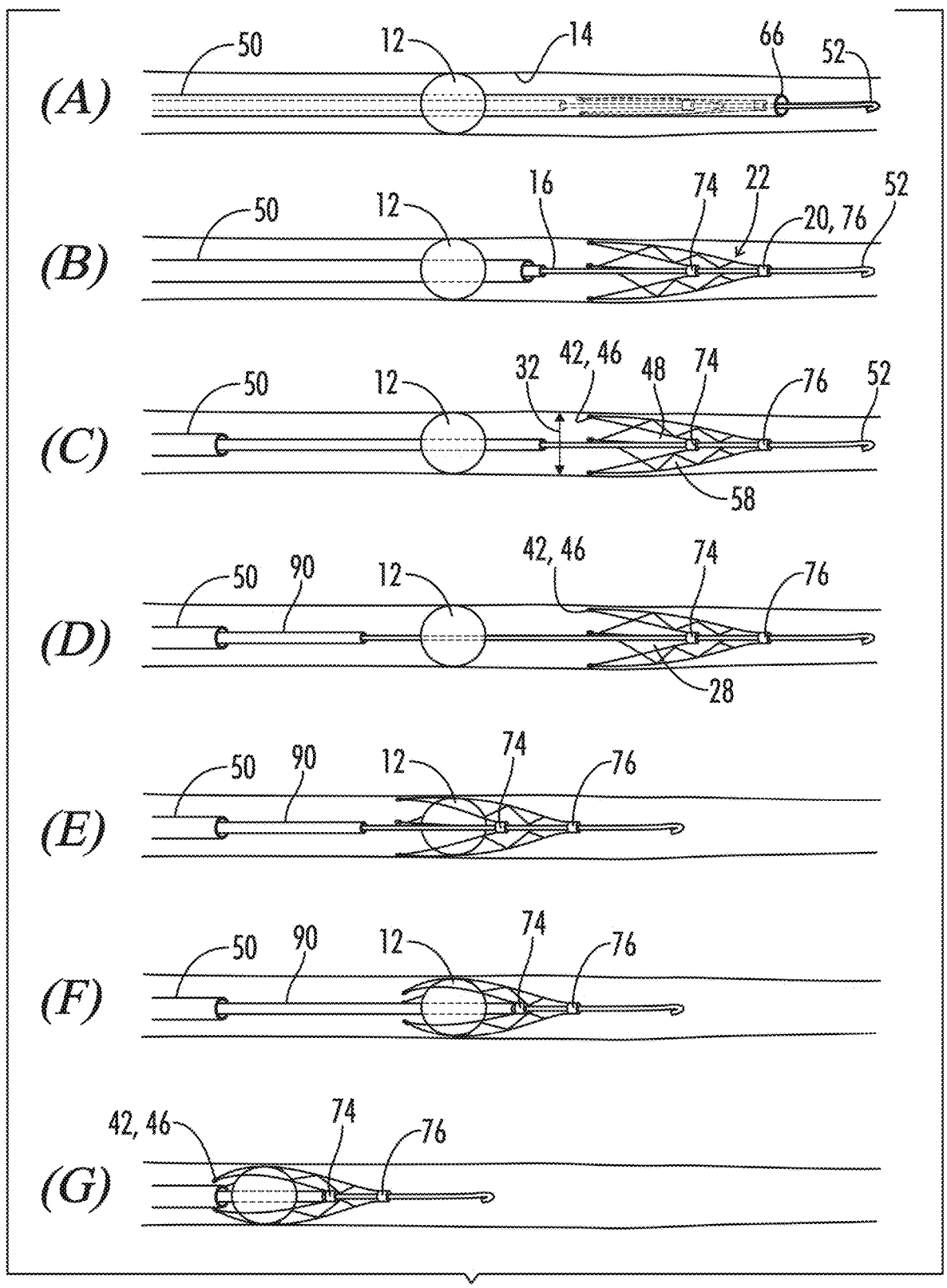
FIG. 10 illustrates a side, elevation view of a deployable system of one embodiment of the present invention being used to capture a blood clot.

Optionally, the distal body 22 includes a basket 54 distal to the proximal memory metal strips 40, the basket 54 comprised of a plurality of memory metal strips 56 distal relative to the proximal memory metal strips 40. The distal memory metal strips 56 may, for example, form a basket 54 with a plurality of mesh openings 58. Optionally, the size of the mesh openings 58 in the basket 54 when the distal body 22 is in its relaxed state is less (preferably significantly less) than the diameter of an average-sized ischemic blood clot 12 so that the blood clot 12 does not escape from the distal basket 54 after being captured by the distal body 22. Optionally, the basket 54 has an open proximal end 60 and a substantially closed distal end 62, which is formed by distal tube 76. Optionally, the distal and proximal hubs 74 and 76 and the distal basket 54 are comprised of a nitinol having the same material composition. Optionally, the size of the mesh openings 58 decreases from the proximal end 60 of the basket 54 to the distal end 62. The distal basket 54 is best seen in FIG. 2 and can be comprised of a different number of cell patterns. The distal basket 54 is not shown in FIGS. 3-10 for ease of illustrating the other components in the system 10.

Optionally, the proximal hub 74 and the distal hub 76 are cylindrical tubes comprising substantially circular apertures that span the length of the hubs 74 and 76 and the hubs 74 and 76 have approximately the same inner diameter 72 and the same outer diameter 70. Preferably, the inner diameter 72 is at least slightly larger than the diameter of the pull wire 16 so that the pull wire 16 can slide through the proximal hub 74. In some embodiments, the outer diameters 70 of the proximal and distal hubs 74 and 76 may be from about 0.011 inches to about 0.054 inches and the inner diameters 72 of the proximal and distal hubs 74 and 76 may be from about 0.008 inches to about 0.051 inches.

Optionally, the distal body 22 further comprises an x-ray marker 64 that is more visible under x-ray as compared to the proximal memory metal strips 40 when the distal body 22 is located in a cranial blood vessel inside the body of a human and the x-ray is taken from outside the human's body. If the connector strips 48 are welded to the proximal memory metal strips 40, the x-ray markers 64 may be, for example, located at the welding site. In some cases, the increased thickness at the welding site may in of itself comprise the x-ray marker 64. Preferably, the x-ray marker 64 is comprised of a radiopaque material. Some examples of radiopaque materials can include, but are not limited to, gold, platinum, palladium, tantalum, tungsten alloy, polymer material loaded with radiopaque filler, and the like. Preferably, the proximal memory metal strips 40 are comprised of nitinol and the x-ray marker 64 is comprised of a material having a density greater than the nitinol.

A catheter 50 with an open proximal end (not shown) and an open distal end 66 initially envelopes the system 10. As used herein, the term "catheter" generally refers to any suitable tube through which the system 10 can be deployed. Preferably, the catheter 50 is sterile and comprised of a biocompatible material (i.e., a material that does not irritate the human body during the course of a 45 minute operation that involves using the system 10 to remove a clot 12 from an intracranial blood vessel 14). The catheter 50 can be any suitable shape, including but not limited to generally cylindrical. Preferably, the catheter 50 is a microcatheter. For purposes of the present invention, when it is said that the catheter 50 envelopes the system 10, it will be understood that the catheter 50 envelopes at least one component of the system 10 (preferably, the distal body 22, the lead wire 52, and the pull wire 16). In some embodiments, the catheter 50 is about 2.5 French in diameter. Optionally, the catheter 50 is delivered to the region of the lumen 14 that has the obstruction 12 as follows: a guide wire is delivered to the obstruction region past the obstruction 12; the catheter 50 is delivered over the guide wire; the guide wire is removed; and the system 10 is delivered with its pull wire 16 and lead wire 52 through the catheter 50. Optionally, the pull wire 16 is used to push the system 10 through the catheter 50 as well as to retrieve the distal body 22 after capturing the obstruction 14 as described below. The system 10 may utilize a plurality of catheters 50, such as, for example, a wider catheter that travels to the brain and a very flexible, smaller diameter microcatheter that is delivered from the first catheter and travels through the small arteries of the brain. Preferably, the catheter 50 is comprised of a biocompatible, polymeric material (i.e., one or more polymeric materials such as silicone, PVC, latex rubber or braided nylon).

Optionally, in the relaxed, opened-claw state, the distal body 22 or optionally just the distal basket 54 has a tapered shape (e.g., substantially conical or bullet in shape) so that the distal body 22 or just the distal basket 54 tapers from the distal body 22 or the distal basket's 54 proximal end to the distal end.

The proximal end of the system 10 is shown at the left end of FIGS. 1 and 3-10 and the distal end of the system 10 is shown at the right end of FIGS. 1 and 3-10 because a principal use of the system 10 is to remove a blood clot 12 from a human intracranial artery 14, in which case the system 10 generally will enter the artery 14 at its proximal end by the surgeon entering the patient's body near the groin and pushing the catheter 50 towards the brain. The diameter of human arteries 14 generally decrease from their proximal end to their distal end. However, when used in other types of lumens, the distal body 22 may be located proximally relative to the catheter 50 as the term proximally and distally are used in that lumen.

The surgeon may deploy the distal body 22 by, for example, moving the catheter 50 proximally so as to unsheathe the distal body 22 or by pushing the distal body 22 out of the catheter 50.

Use of the system 10 will now be described to remove a blood clot 12 from an intracranial artery 14 of a human ischemic stroke patient, however, it will be appreciated that the system 10 may be used to remove other objects from other interior lumens.

A catheter 50, which contains the collapsed distal body 22 is positioned in the lumen 14 distal to the clot 12. See FIG. 10A.

The distal body 22 is deployed from the catheter 50 and the height and width of the distal body 22 expand to about the height and width of the blood vessel 14. See FIG. 10B.

The catheter 50 is pulled proximally and a claw-actuator tube 90 is deployed into the blood vessel 14. See FIG. 10C.

The distal body 22 is moved proximally so that the clot 12 is located in the interior 28 of the distal body 22. See FIGS. 10D and 10E.

The claw-actuator tube 90 is moved distally, which pushes the proximal hub 74 distally so that the distance 88 between the proximal hub 74 and the distal hub 76 (which is fixed to the pull wire 16 and kept stationary) decreases. Distal movement of the proximal hub 74 exerts tension on the connector and proximal memory metal strips 40 and 48, which in turn, closes the claw 46. See FIG. 10F. (The claw actuator tube 90 should float on the pull wire 16—i.e., have an aperture extending the tube's length that has a diameter larger than the diameter of the pull wire 16—and the aperture of the claw actuator tube 90 should be smaller than the diameter of the proximal hub 74 so that the claw actuator tube 90 pushes the proximal hub 74).

The system 10 is withdrawn proximally and removed from the body. See FIG. 10G.

To test the efficacy of the system 10, a distal body 22 with a distal basket 54, proximal and distal hubs 74 and 76, and a claw 46 comprised of three proximal memory metal strips 42 was tested in a flow model that included a tube and a moist cotton ball located in the tube. The cotton ball was used to simulate a blood clot. The system 10 was deployed distal to the cotton ball. The claw 46 was closed by moving the proximal hub 74 distally to capture the cotton ball. The system 10 and cotton ball were withdrawn proximally in the tube.

In some embodiments, the distal body 22 is prepared by a process that includes one or more of the following steps, as illustrated in FIGS. 1-4
a) providing a single tube 68 comprised of a memory metal such as nitinol, the single tube 68 having an exterior, a substantially hollow interior, a wall separating the exterior from the substantially hollow interior, an open proximal end 74, an open distal end 76, a middle portion 78 between the open proximal end 74 and the open distal end 76 (see FIG. 1A);
b) cutting the wall of the middle portion 78 with a laser 80 (see FIG. 1B);
c) removing the pieces of the middle portion 78 cut by the laser 80 to form a proximal tube 74, a distal tube 76 and a middle portion 78 comprising a plurality of memory metal strips 82 attached to the proximal tube 74;
d) altering the shape of the middle portion 78 using a mandrel and allowing the middle portion 78 to expand relative to the distal tube 76 and proximal tube 74 to form the distal basket 54;
e) quenching the middle portion 78 at room temperature;
f) removing the mandrel from the middle portion 78 (see FIGS. 2 and 3A);
g) mechanically or chemically electropolishing the middle portion 78 to remove oxides;
h) cutting the memory metal strips 82 to form a first segment 84 comprising the proximal tube 74 and a proximal segment of the memory metal strips 82 and a second segment 86 comprising the distal tube 76 and a distal segment of the memory metal strips 82 (see FIG. 3B); and
i) joining the proximal segments to the distal segments such that the distal segments form the proximal end 24 of the distal body 22, such that the proximal tube 74 is located inside the interior 28 of the distal body 22, and such that the proximal tube 74 is located distal relative to the distal body proximal end 24 (see FIGS. 3C-3E).

In some embodiments, the method further includes placing the pull wire 16 through the proximal tube 74 so that the proximal tube 74 is slideable along at least a segment of the pull wire 16.

In some embodiments, the method further includes attaching the pull wire 16 to the distal tube 76 so that the distal tube 76 is not slideable along the pull wire 16 but instead the distal tube 76 moves with the pull wire 16.

In some embodiments, after step i, the proximal end 24 of the distal body 22 forms a claw 46 comprised of between 2 to 4 proximal memory metal strips 40, the claw proximal memory metal strips 40 configured to move towards each other and the pull wire 16 by moving the proximal tube 74 distally and toward the distal tube 76 (i.e., decreasing the distance 88 between the tubes 74 and 76) and the claw memory metal strips 40 configured to move away from each other and away from the pull wire (i.e., increasing the distance 88 between the tubes 74 and 76) by moving the proximal tube 76 proximally and away from the distal tube 76 (as described previously).

In some embodiments, the middle portion 78 is expanded by heating the mandrel and the middle portion 78 by, for example, placing the mandrel and the middle portion 78 in a fluidized sand bath at about 500° C. for about 3 to about 7 minutes. As the middle portion 78 is heated, the heating causes the crystalline structure of the memory metal tube 68 to realign. Preferably, the mandrel is tapered (e.g., substantially conical or bullet in shape) so that the distal basket 54 formed from the middle portion 78 tapers from the proximal end 60 to the distal end 62. Preferably, the proximal and distal ends of the tube 74 and 76 are not shape set by the mandrel and are not cut by the laser 80 so that the proximal and distal ends 74 and 76 do not change in shape and only slightly expand in size under heating and return to the size of the native tube 68 after the heat is removed. Preferably, the laser cuts are programmed via a computer. To ensure that the laser cuts only one surface of the tube wall at the time (and not the surface directly opposite the desired cutting surface), the laser 80 is preferably focused between the inner and outer diameter of the desired cutting surface and a coolant is passed through the memory metal tube 68 so that the laser 80 cools before reaching the surface directly opposite the desired cutting surface.

The portions of the wall not cut by the laser 80 create the distal basket 53, proximal and distal tubes 74 and 76, and memory metal strips 40, 48 and 56, as described.

Preferably, the memory metal selected for the native tube 68 has a heat of transformation below average human body temperature (37° C.) so that the distal body 22 has sufficient spring and flexibility after deployment from the catheter 50 in the human blood vessel 14.

In some embodiments, the native tube 68 (and hence the distal and proximal tubes 74 and 76) have an outer diameter of less than about 4 French, e.g., a diameter of about 1 to about 4 French. In some embodiments, the diameter of the pull wire 16 is between about 0.008 inches and about 0.051, as noted above, and in such embodiments, the diameter of the pull wire 16 may be approximately equal to the inner diameter 72 of the native nitinol tube 68.

Without being bound by any particular theory, it is believed that manufacturing the distal body 22 from a single memory metal tube 68 provides ease of manufacturing and safety from mechanical failure and provides tensile strength necessary for the system 10 to remove hard thrombus 12 and other obstructions.

THE EMBODIMENTS OF FIGS. 11-29

FIGS. 11-29 illustrate an alternate embodiment 200 that includes one or more of the following additional features, as described below: twisting proximal strips/tethers 252, unattached/free distal-pointing crowns 258 that optionally curve inward and have x-ray markers 244, and enlarged openings/ drop zones 262 in the basket 246 immediately distal to the unattached, distal-pointing crowns 258 that allow the obstruction or other object 270 to enter the distal basket interior 222.

Figure 11:
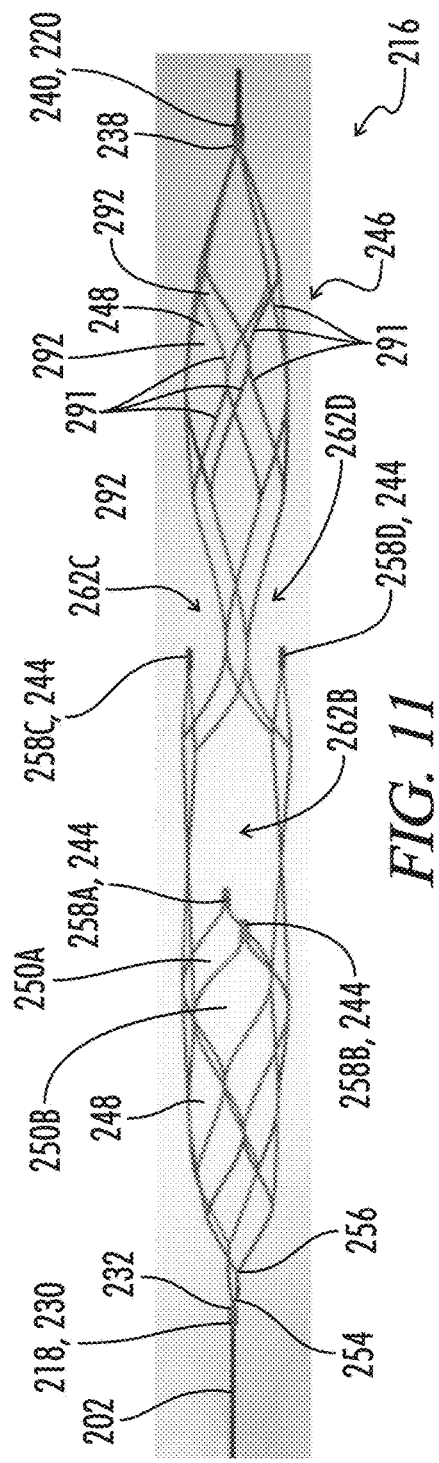
FIG. 11 illustrates a first, perspective view of a distal body of an alternate embodiment of the present invention; the distal body is in what is referred to herein as "Orientation 1".

More specifically, as shown in FIGS. 11-29, the system 200 may include a pull wire 202 having a proximal end 204 and a distal end 206, as described above, a distal body 216 attached to the pull wire 202, the distal body 216 comprising an interior 222, a proximal end 218, a distal end 220, a distal body length 226 extending from the proximal end 218 to the distal end 220, a distal body height 224, a proximal hub 228 (preferably in the form of a tube and which has a proximal end 230 and a distal end 232) forming the proximal end 218 of the distal body 216, a basket 246 comprised of a plurality of cells/openings 248 formed by a plurality of basket strips 291 that preferably are comprised of a memory metal, optionally a distal hub 236 that forms the distal end 220 of the basket 246 (preferably in the form of a tube that has a proximal end 238 and a distal end 240), and a plurality of proximal strips 252 (preferably the proximal strips 252 are comprised of a memory metal), each proximal strip 252 having a proximal end 254 attached to the proximal hub/tube 228, and a distal end 256 attached to a cell 248 (more specifically a proximal-pointing crown of a cell 248 located at the proximal end of the basket 246), the basket comprising a basket interior 292, the distal body 216 having a relaxed state wherein the distal body 216 has a first height and width, a collapsed state wherein the distal body 216 has a second height and width, the second height less than the first height, the second width less than the first width; and a delivery catheter 208 for delivering the distal body 216, as described above, having an interior 210, a proximal end 212 leading to the interior 210 and a distal end 214 leading to the interior 210, the delivery catheter 208 comprised of a biocompatible (preferably polymeric) material and configured to envelope the distal body 216 when the distal body 216 is in the collapsed state. Optionally, the basket interior 292 is substantially hollow—i.e., unlike U.S. Patent Publication No. 2013/0345739, the basket interior 292 does not contain an inner elongate body. Optionally, instead of a distal hub 236, the basket 246 includes an open distal end. Optionally, at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246. In other words, the distal crowns 258 of at least two cells 250 are free floating and are not attached to any strip except for the strips forming part of the at least two cells 250; such distal crowns 258 are referred to below as unattached, distal-pointing crowns 258. Preferably, the distal tips of the unattached, distal-pointing crowns 258 terminate at an x-ray marker 244. (Cells labeled with the numerals 250, 250A, 250B, 250C, and 250D refer to the at least two cells that include a proximal crown 260 pointing generally in the proximal direction and an unattached, distal-pointing crown 258, cells labeled with the numerals 262, 262A, 262B, 262C, and 262D refer to the enlarged cells/drop zones adjacent to (preferably immediately distal to) an unattached, distal-pointing crown 258, and cells designated with numeral 248 refer to generally the cells of the basket 246). (When it is said that the enlarged cells/drop zones 262 are preferably immediately distal to an unattached, distal-pointing crown 258, it will be understood that at least a portion of an enlarged cell/drop zone 262 is immediately distal to an unattached, distal-pointing crown 258, and that a portion of the enlarged cell/drop zone 262 may be proximal to an unattached, distal-pointing crown 258, as shown in FIGS. 11-12 due to the shape of the enlarged cells/drop zones 262). It will be understood that part number 250 refers generally to one or more of the at least two cells, whereas part numbers 250A, 250B, 250C, and 250D refer to a specific one of the at least two cells. Similarly, it will be understood that part number 262 refers generally to one or more of the enlarged cells/drop zones, whereas part numbers 262A, 262B, 262C, and 262D refer to a specific one of the enlarged cells/drop zones. Similarly, it will be understood that part number 258 refers generally to one or more of the unattached, distal-pointing crowns, whereas part numbers 258A, 258B, 258C, and 258D refer to a specific one of the unattached, distal-pointing crowns.

Figure 12A:
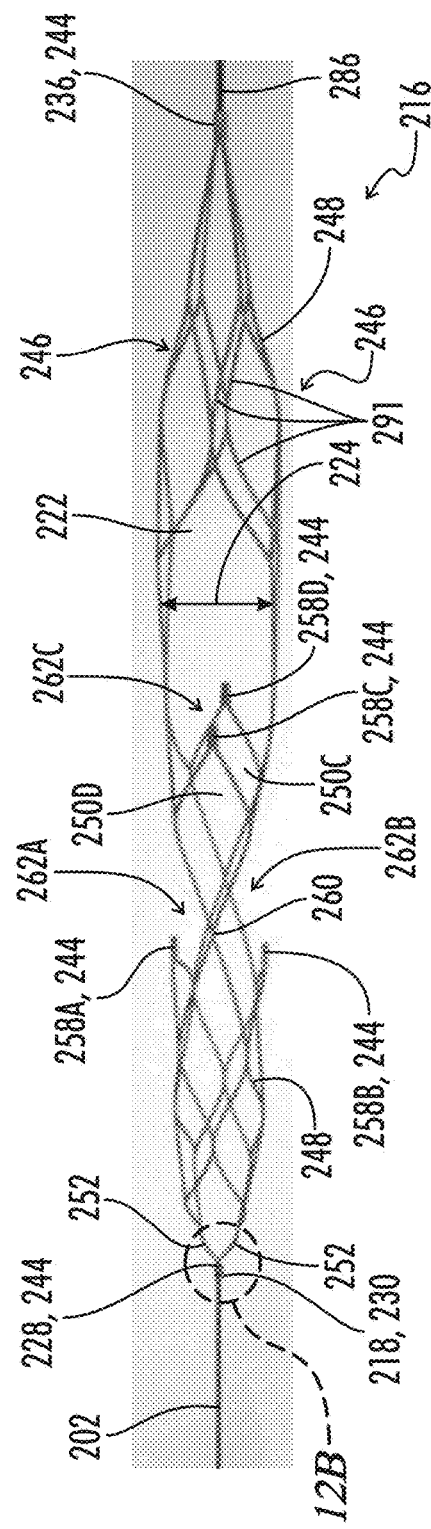
FIG. 12A illustrates a second, perspective view of the distal body of FIG. 11; the distal body is in what is referred to herein as "Orientation 2".
Figure 12B:
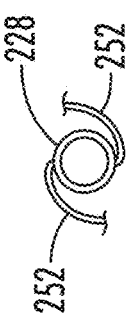
FIG. 12B illustrates a proximal, elevation view of the proximal strips of the distal body of FIG. 11.

Optionally, at least two of the unattached, distal-pointing crowns 258 are located approximately 180 degrees (e.g., about 150 to about 180 degrees) relative to each other and approximately the same distance from the proximal hub/tube 228, as best seen in FIG. 12A. Optionally, the basket 246 comprises a first pair of unattached, distal-pointing crowns 258A and 258B, each of the first pair of unattached, distal-pointing crowns 258A and 258B is located approximately the same distance from the proximal hub/tube 228 and approximately 180 degrees relative to each other, and the basket 246 further comprises a second pair of unattached, distal-pointing crowns 258C and 258D located distally relative to, and approximately 90 degrees (e.g., between about 60 and about 90 degrees) relative to, the first pair of unattached, distal-pointing crowns 258A and 258B. Optionally, the second pair of unattached, distal-pointing crowns 258C and 258D form cells 250C and 250D that are adjacent to, but offset from, the cells 250A and 250B formed by the first pair of unattached, distal-pointing crowns 258A and 258B. (In other words, optionally, the center of cell 250A is about 90 degrees relative to the centers of cells 250C and 250D and optionally the center of cell 250B is also about 90 degrees relative to the centers of cells 250C and 250D). Optionally, at least one of (and preferably all) the unattached, distal-pointing crowns 258A, 258B, 258C or 258D comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the x-ray markers 244 comprise a heavy metal welded to the unattached, distal-pointing crowns 258. Optionally, the unattached, distal-pointing crowns 258 curve subtly towards the interior 222 of the distal basket 246, which decreases the likelihood that the unattached, distal-pointing crowns 258 will rub against and damage the vessel wall 268. Optionally, the basket 246 comprises at least two cells proximal to the at least two cells 250 that include the unattached, distal-pointing crowns 258. Optionally, the unattached, distal-pointing distal crowns 258 are located about at least 5 mm (e.g., about 5 to about 30 mm) from the proximal hub/tube 228. Optionally, the unattached, distal-pointing crowns 258 are located at least about 5 mm from the distal hub/tube 236. Optionally, the unattached, distal-pointing crowns 258 of the at least two cells 250 also each form part (namely a portion of the proximal boundary) of an enlarged cell 262 (which is the entry point of hard thrombus 270B into the basket interior 222) and further wherein the surface area of the enlarged cells 262 in the relaxed state is greater than the surface area of the other cells of the basket 246 in the relaxed state. Optionally, the unattached, distal-pointing crowns 258 serve several functions: 1) they form flex points of the basket 246, which makes it easier for the system 200 to navigate the curves of the blood vessels 266 of the brains; 2) through the use of x-ray markers 244 on the unattached, distal-pointing crowns 258, they allow the operator to locate the enlarged cells 262 of the basket 246 that form the point at which hard thrombuses 270B enter the basket 246; and 3) they allow the operator to ratchet or force the object 270 into the basket 246 by moving the unattached, distal-pointing crowns 258 proximally and distally relative to the object 270. (As explained below, the numeral 270 refers to clots/thrombuses and other objects generally, and 270A refers to a soft clot, 270B refers to a hard clot and 270C refers to a deformable, cohesive, adherent clot). Optionally, the proximal end 254 of a proximal strip 252 is located about 65-180 degrees (preferably approximately 180 degrees) relative to the distal end 256 of the same proximal strip 252, as best seen in FIG. 12B. In other words, preferably the proximal end 254 of a first proximal strip 252 is attached to the 12 o'clock position on the proximal tube 228 and the distal end 256 of the first proximal strip 252 (which terminates at a proximal cell 248 of the basket 246) is located at the 6 o'clock position (i.e., 180 degrees from the start position), and the proximal end 254 of a second proximal strip 252 is attached to the 6 o'clock position on the proximal tube 228 and the distal end 254 (which terminates at a cell 248 of the basket 246) of the second proximal strip 252 is located at the 12 o'clock position (i.e., 180 degrees from the start position). This twisting feature serves two functions: 1) it allows the proximal strips 252 to surround the object 270; and 2) it allows the manufacturer to insert a mandrel into the basket 246 during the shape-setting procedure. Optionally, the pull wire 202 is attached to the proximal tube 228 (e.g., by gluing, welding or the like). Preferably, the pull wire 202 does not extend through the distal basket interior 222. Optionally, the proximal strips 252 are integral with the distal end 232 of the proximal tube 228 and the entire distal body 216 is created from a single tube 264 of a memory metal. Optionally, the proximal crowns 260 of the at least two cells 250 that include the unattached, distal pointing-crowns 258 are each attached to another cell 248 of the basket 246. In other words, preferably the basket 246 does not have any free-floating proximal-pointing crowns, as free-floating proximal-pointing crowns could damage the vessel 266 when the distal body 216 is pulled proximally. Optionally, the system 200 further comprises a lead wire 286 extending distally from the distal tube 236, the lead wire 286 having a length of from about 3 mm to about 10 mm. Optionally, the distal hub/tube 236, the proximal hub/tube 228, and the basket 246 are comprised of a nitinol having the same material composition. In other words, as with the prior embodiment of FIGS. 1-10, optionally the entire distal body 216 is manufactured from a single tube of nitinol 264. Optionally, the proximal and distal hubs/tubes 228 and 236 comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the proximal and distal hubs/tube interiors 234 and 242 may comprise tantalum welded or otherwise attached to the interior 234 and 242 of the proximal and distal hubs/tubes 228 and 236. Optionally, the proximal and the distal tubes 228 and 236 are generally cylindrical in shape and each has an outer diameter and an inner diameter, the inner diameter forming apertures of the proximal and distal tubes 228 and 236 and further wherein the outer diameters of the proximal and distal tubes 228 and 236 are substantially the same size and further wherein the inner diameters of the proximal and distal tubes 228 and 236 are substantially the same size. Optionally, the outer diameters of the proximal and distal tubes 228 and 236 are from about 0.011 inches to about 0.054 inches, and further wherein the inner diameters of the proximal and distal tubes 228 and 236 are from about 0.008 inches to about 0.051 inches. Optionally, the pull wire 202 is generally cylindrical and further wherein the diameter of the pull wire 202 is between about 0.008 inches and about 0.051 inches. Optionally, the distal body 216 has a length of between about 10 and about 60 millimeters. Optionally, the first height 224 and first width 226 of the distal body 216 are between about 2 millimeters and about 6 millimeters.

The present disclosure also provides a method of removing a clot or other object 270 from an interior lumen 266 of an animal, the method comprising the steps of:

a) providing the system 200 of FIGS. 11-29, wherein at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246 (i.e., free-floating), and further wherein at least one of the unattached, distal-pointing crowns 258 comprises an x-ray marker 244;

b) positioning the system 200 in the lumen 266;

c) deploying the distal body 216 from the distal end 214 of the delivery catheter 208;

d) allowing the height and width 224 and 226 of the distal body 216 to increase;

e) irradiating the x-ray marker 244 with x-ray radiation and f) moving the object 270 into the distal basket interior 222.

Optionally, the object 270 enters the distal basket interior 222 adjacent to (preferably adjacent and immediately distal to) at least one of the unattached, distal-pointing crowns 258—i.e., in the enlarged cells/drop zones 262. In some embodiments, the distal body 216 is deployed so that at least one (e.g., preferably the two proximal 258A and 258B) of the unattached, distal-pointing crowns 258 is distal to the object 270. As explained below, the x-ray markers 244 of the unattached, distal-pointing crowns 258 are used to locate the distal body 216 relative to the clot or other object 270. It will be appreciated that clots 270 can generally be located in blood vessels 266 by injecting a contrast dye, for example, into the blood vessel 266 proximal and distal to the believed area of obstruction and viewing on an x-ray where the fluid stops moving in the blood vessel 266. It will also be appreciated that if the object 270 is not a blood clot but is a radio-opaque object, the object 270 may be viewed on an x-ray.

Figure 14A:
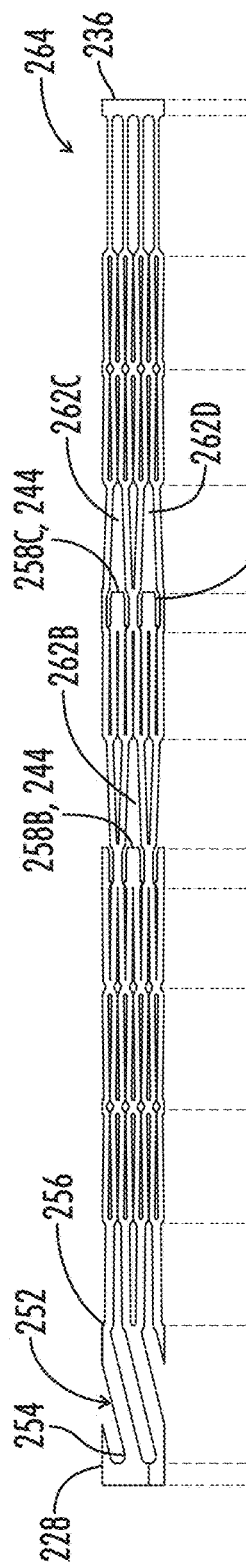
FIG. 14A illustrates a native memory metal tube used to manufacture the distal body of FIG. 11; the native tube has been rolled out flat and the lines in the tube indicate where the tube has been cut by a laser.
Figure 14B:
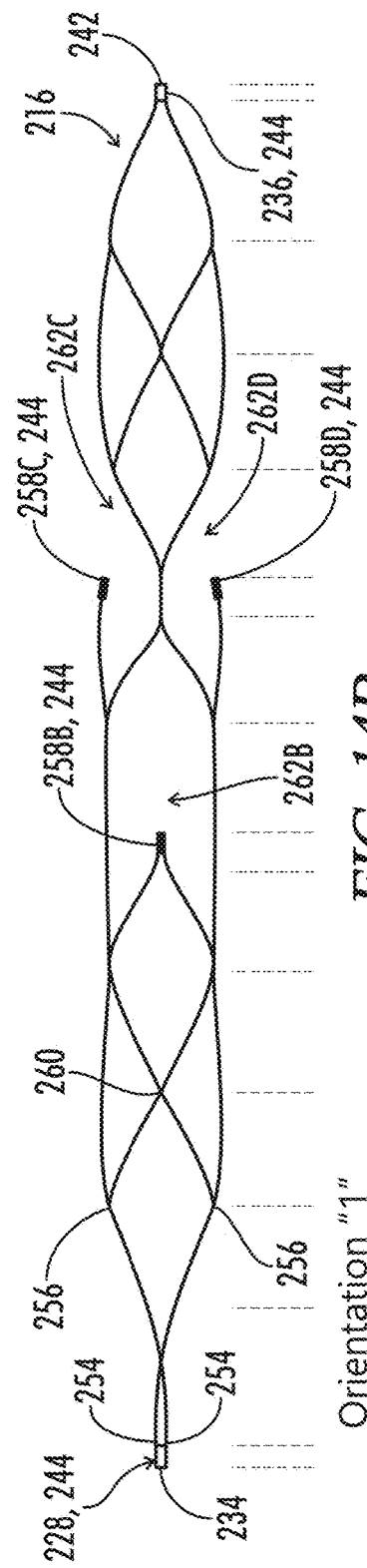
FIG. 14B illustrates a first, perspective view of the distal body manufactured from the native tube of FIG. 14A; the distal body is in Orientation 1.

FIGS. 11 and 14B illustrate a first, perspective view of one embodiment of a distal body 216 with twisting proximal strips 252, unattached distal-pointing crowns 258 that subtly curve inward and have x-ray markers 244, and enlarged openings/drop zones 262 in the basket 246 that allow the obstruction or other object 270 to enter. In FIGS. 11 and 14B, the distal body 216 is in Orientation 1. (To prepare a basket 246 with unattached distal-pointing crowns 258 that curve inward toward the basket interior 292, a mandrel 900 such as that illustrated in FIGS. 30 and 31 may be used. The mandrel 900 includes a generally cylindrical body 901 with tapered proximal and distal ends 902 and 903 that slope like the ends of a pencil. The cylindrical body 901 includes two grooves 904 that extend around the circumference of the cylindrical body 901. The grooves 904 include tapered portions 905 that slope towards the distal end 903, which are designed to shape the unattached distal-pointing crowns

Figure 13:
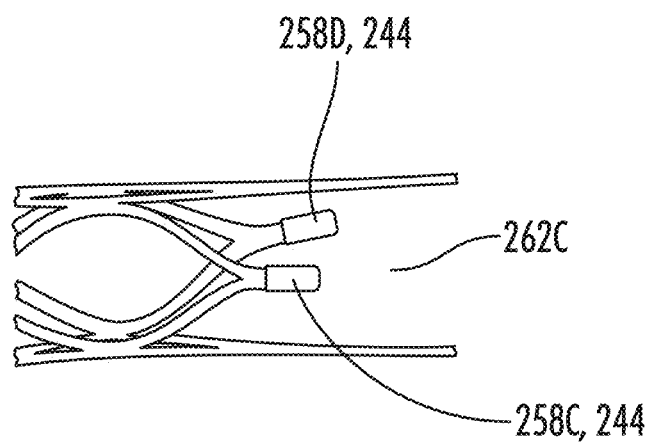
FIG. 13 illustrates a close-up, perspective view of two unattached distal-pointing crowns of the distal body of FIG. 11.
Figure 14C:
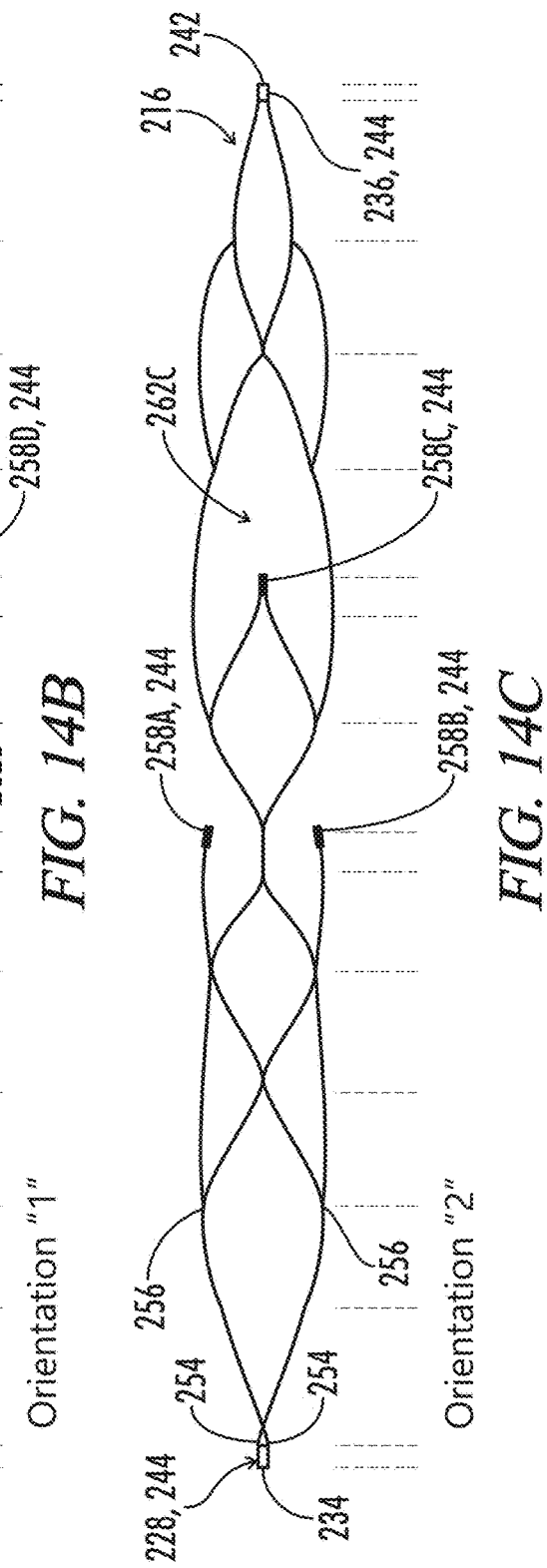
FIG. 14C illustrates a second, perspective view of the distal body manufactured from the native tube of FIG. 14A; the distal body is in Orientation 2.
Figure 30:
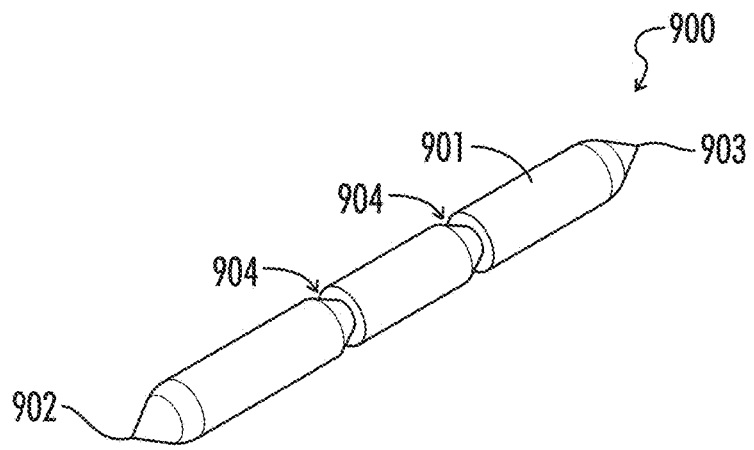
FIG. 30 illustrates a right side perspective view of a mandrel used to prepare unattached distal-pointing crowns that curve radially toward the basket interior.
Figure 31:
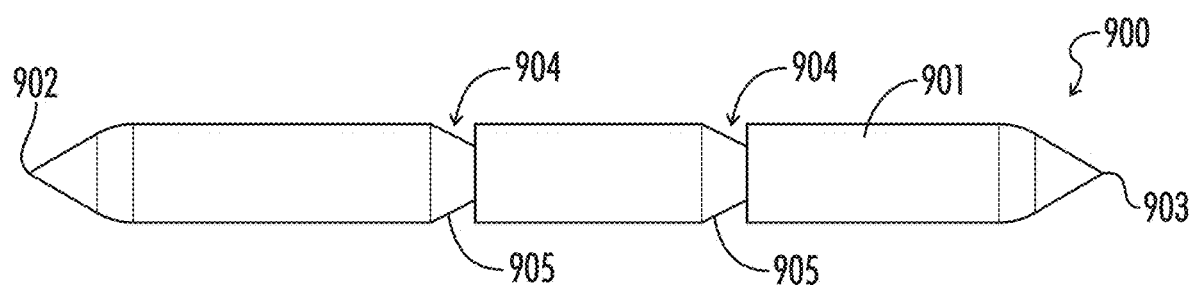
FIG. 31 illustrates a right side elevation view of the mandrel of FIG. 30.

258. The grooves 904 are generally in the shape of a truncated cone, as shown in FIGS. 30-31). The two proximal, unattached distal-pointing crowns 258A and 258B are located approximately the same distance from the proximal hub/tube 228 and are oriented approximately 180 degrees relative to each other. The two distal, unattached distal-pointing crowns 258C and 258D are located approximately the same distance from the proximal hub/tube 228 as each other (and distal to the two proximal, unattached distal-pointing crowns 258A and 258B) and are oriented approximately 180 degrees relative to each other and approximately 90 degrees to the proximal, unattached distal-pointing crowns 258A and 258B. The two proximal enlarged openings/drop zones 262A and 262B distal to the proximal, unattached distal pointing crowns 258A and 258B are located approximately the same distance from the proximal hub/tube 228 and the centers of the two proximal enlarged openings/drop zones 262A and 262B are oriented approximately 180 degrees relative to each other. (As noted above, preferably, the proximal, unattached distal-pointing crowns 258A and 258B form part of the proximal boundary of the proximal, enlarged cells/drop zones 262A and 262B, and the distal, unattached distal-pointing crowns 258C and 258C form part of the proximal boundary of the distal, enlarged cells/drop zones 262C and 262D). The two distal, enlarged openings/drop zones 262C and 262D distal to the distal, unattached distal pointing crowns 258C and 258D are located approximately the same distance from the proximal hub/tube 228 and the centers of the distal, enlarged openings/drop zones 262C and 262D are oriented approximately 180 degrees relative to each other and approximately 90 degrees relative to the proximal enlarged openings/drop zones 262A and 262B. FIGS. 12A and 14C illustrate a second view of the distal body 216 of FIG. 11 (Orientation 2). FIG. 13 is a close-up view of two unattached, distal-pointing crowns 262. The lines in FIG. 14 show how a nitinol tube 264 is cut with a laser to create the distal body 216 shown in FIG. 14B and FIG. 14C. It will be appreciated that FIG. 14B is a simplified view of the distal body 216 and orientation shown in FIG. 11 and FIG. 14C is a simplified view of the distal body 216 and orientation shown in FIG. 12A.

As described below, FIGS. 15-19 describe how the distal body 216 is used to retrieve, soft clots 270A, hard clots 270B, and deformable, cohesive adhesive clots 270C in a human intracranial artery 266. (In FIGS. 15-19, the center of the artery 266 is denominated by the dashed line). As explained below, the distal body 216 has four rows of x-ray markers namely, 1) a first row of one x-ray marker, which is located inside the proximal tube denominated by the numeral 228, 244; 2) a second row of two x-ray markers, which are located at the two proximal, unattached distal-pointing crowns (the two markers are oriented 180 degrees relative to each other) denominated by the numerals 258A, 244 and 258B, 244; 3) a third row of two x-ray markers, which are located at the two distal, unattached distal-pointing crowns (these two markers are oriented 180 degrees relative to each other and 90 degrees relative to the two proximal, unattached distal-pointing crowns) denominated by the numerals 258C, 244 and 258D, 244; and 4) a fourth row of one x-ray marker, which is located inside the distal tube denominated by the numeral 236, 244. (It will be appreciated that the first number in the sequence describes the position of the x-ray marker and the second number, 244, represents the fact that the item is an x-ray marker). As explained below, upon deploying the distal body 216 so that the two proximal, unattached distal-pointing crowns 258A, 244 and 258B, 244 are immediately distal to the clot 270, the surgeon interventionalist (i.e., operator of the distal body 216) detects the four rows of x-ray markers using x-ray radiation from a first vantage point and from a second vantage point that is offset from the first vantage point (e.g. 90 degrees). Next, the surgeon moves the distal body 216 proximally relative to the clot 270 and takes additional x-rays from the first and second vantage points. As explained in greater detail below, the surgeon uses the x-ray markers of the proximal and distal, unattached distal-pointing crowns, namely 258A, 244; 258B, 244; 258C, 244; and 258D, 244 (more specifically, the convergence or lack thereof of the proximal and distal, unattached distal-pointing crowns 258A, 244; 258B, 244; 258C, 244; and 258D, 244 as shown on the x-ray) to determine whether the clot 270 is located inside the distal body interior 222 or whether the clot 270 is collapsing the distal body 216.

Figure 15A:
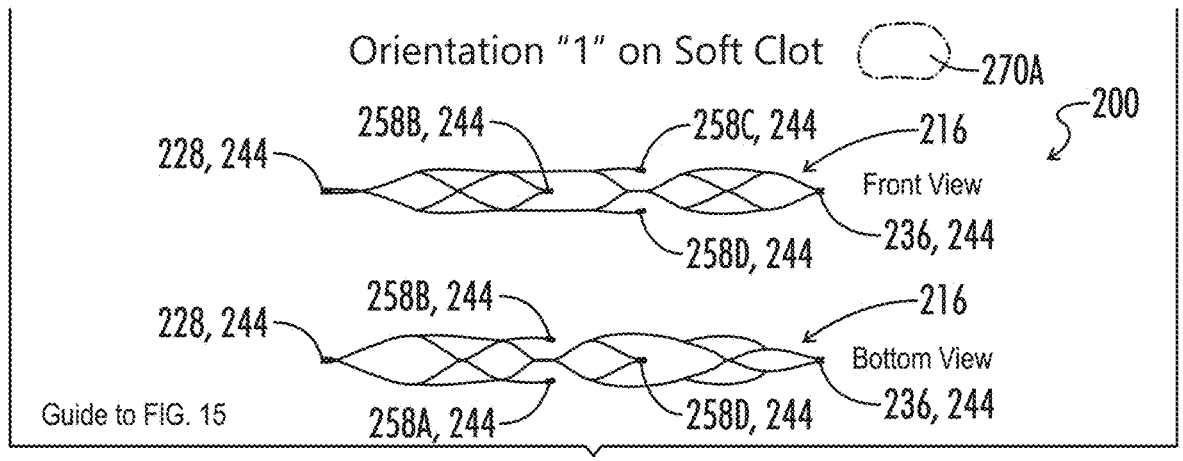
FIGS. 15A-G illustrate stepwise use of the distal body of FIG. 11 in retrieving a soft clot; the distal body is in Orientation 1.
Figure 15B:
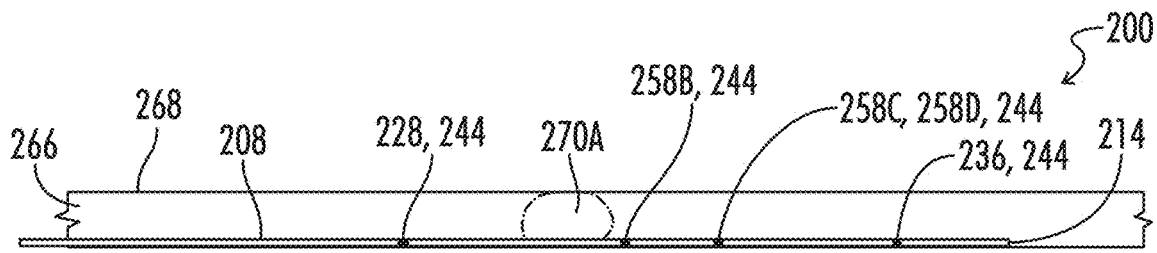
Figure 15C:
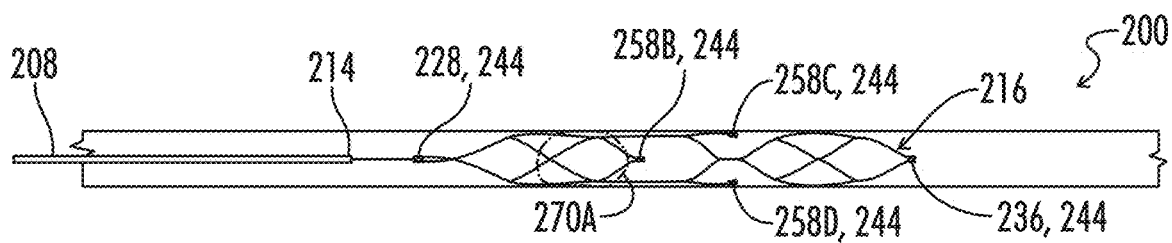
Figure 15D:
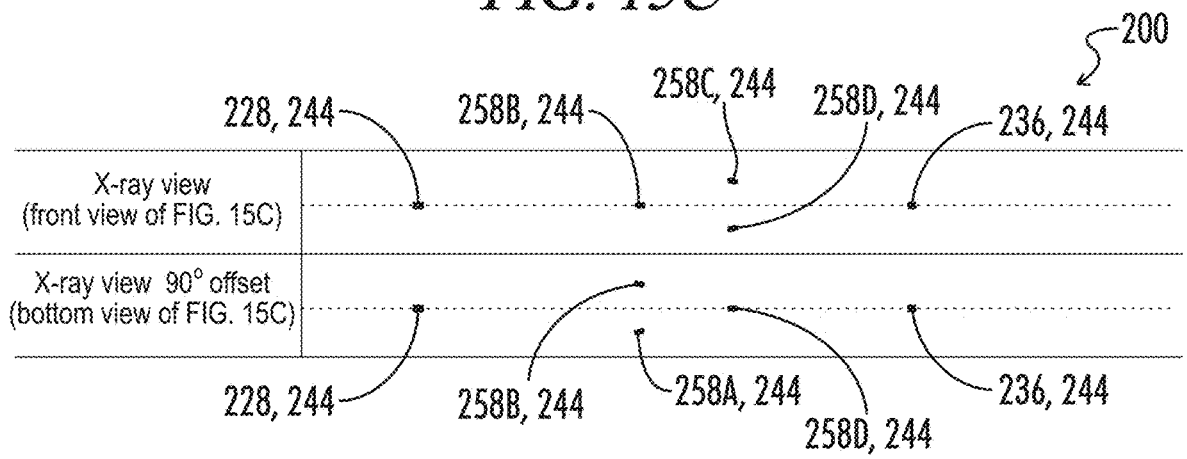
Figure 15E:
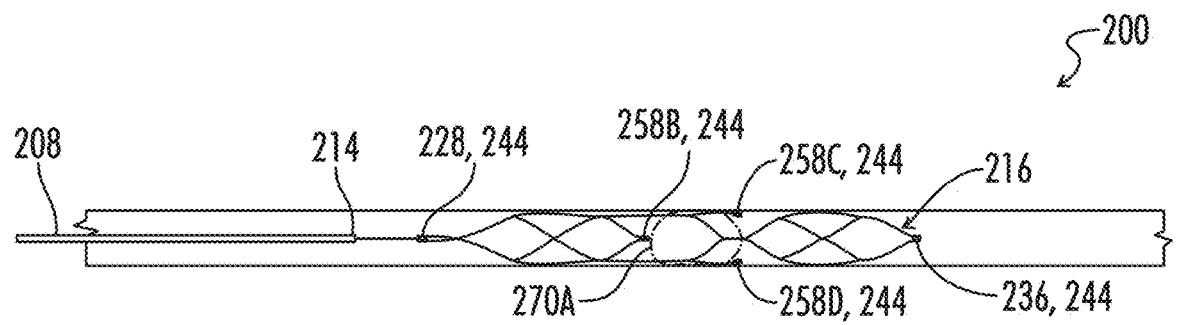
Figure 15F:
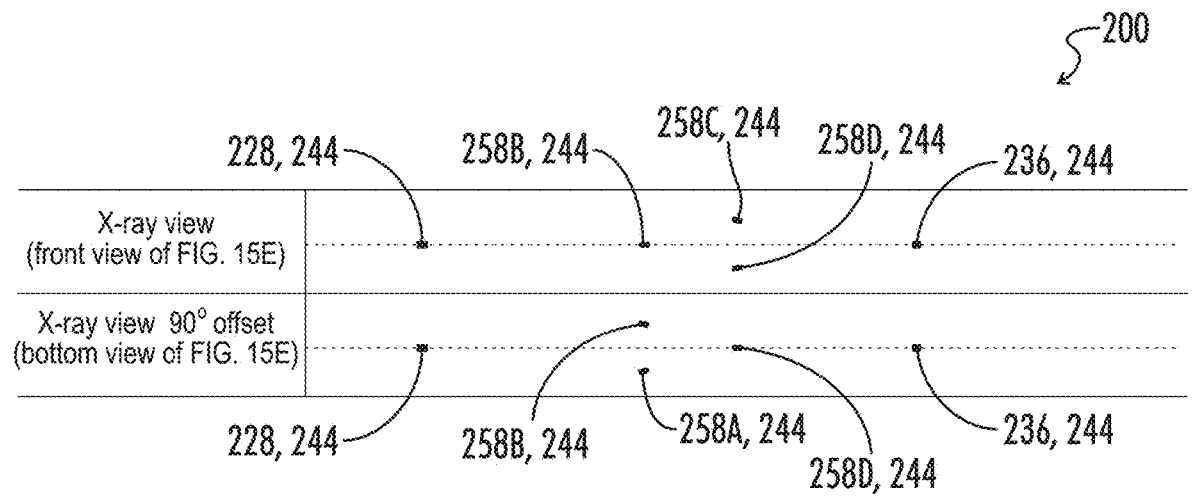
Figure 15G:
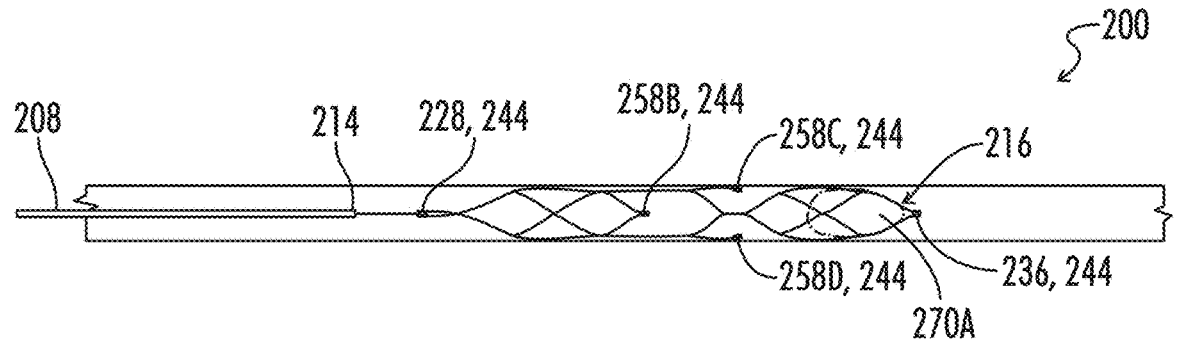

More specifically, FIGS. 15A-G illustrate stepwise use of the distal body 216 in retrieving a soft clot 270A in a human intracranial artery 266. (The distal body 216 in FIGS. 15A-15G is in Orientation 1). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 15B. The distal body 216 is then deployed from the delivery catheter 208 by moving the catheter 208 proximally. The soft clot 270A, which is unable to collapse the distal body 216, then enters the distal body interior 222. See FIG. 15C. However, at this time, the surgeon is unaware that the clot 270A has entered into the distal body interior 222. Thus, without moving the distal body 216, the surgeon irradiates the four rows of x-ray markers at a first vantage point (i.e., from the front of the distal body 216 in the orientation shown in FIGS. 15A-G; i.e., into the page). As shown in FIG. 15D, the first vantage point shows four rows of x-ray markers. The first row is a single point, which represents the x-ray marker located in the proximal tube 228, 244; the proximal tube x-ray marker 228, 244 always appears as a single point. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row 258C, 244 and 258D, 244 is hidden from view on the x-ray at this angle—rather, one marker 258C, 244 is located above the other marker 258D, 244—and as shown in FIG. 15C, the distal body 216 is not collapsed at the distal, unattached distal-pointing crowns 258C, 244 and 258D, 244. The fourth row is a single point, which represents the x-ray marker located in the distal tube 236, 244; the distal tube x-ray marker 236, 244 always appears as a single point. Without moving the distal body 216, the surgeon then irradiates the four rows of x-ray markers from a second vantage point 90 degrees offset from the first vantage point (i.e., from the bottom of the distal body 216 in the orientation shown in FIG. 15A). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker 258A, 244 and 258B, 244 in the second row is hidden from view on the x-ray at this offset angle—rather, one marker 258B, 244 is located above the other marker 258A, 244—and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the x-ray markers at the second row 258A, 244 and 258B, 244 nor the x-ray markers at the third row 258C, 244 and 258D, 244 (i.e., the x-ray markers at both the proximal and distal unattached distal pointing-crowns) have converged. As shown in FIG. 15E, the surgeon then moves the distal body 216 proximally relative to the soft clot 270A so that the distal, unattached distal-pointing crowns 258C, 244 and 258D, 244 are immediately distal to the clot 270A and then the surgeon irradiates the four rows of x-ray markers again from the first vantage point and the second vantage point. As shown in FIG. 15F, the results are the same as FIG. 15D. With the results from FIGS. 15D and 15F, the surgeon concludes that neither x-ray markers at the second row 258A, 244 and 258B, 244 nor the x-ray markers at the third row 258C, 244 and 258D, 244 (i.e., the x-ray markers at both the proximal and distal unattached distal pointing-crowns) converged at either the original position of the distal body 216 (FIGS. 15C and 15D) or the position after moving the distal body 216 proximally (FIGS. 15E and 15F), and, thus, the distal body 216 was expanded in the vessel 266 in both positions. Thus, the surgeon concludes that the clot is a soft clot 270A that has entered into the distal body interior 222 and the surgeon removes the distal body 216 and the soft clot 270A, captured by the distal body 216, by moving the distal body 216 proximally out of the vessel 266, as shown in FIG. 15G.

Figure 16A:
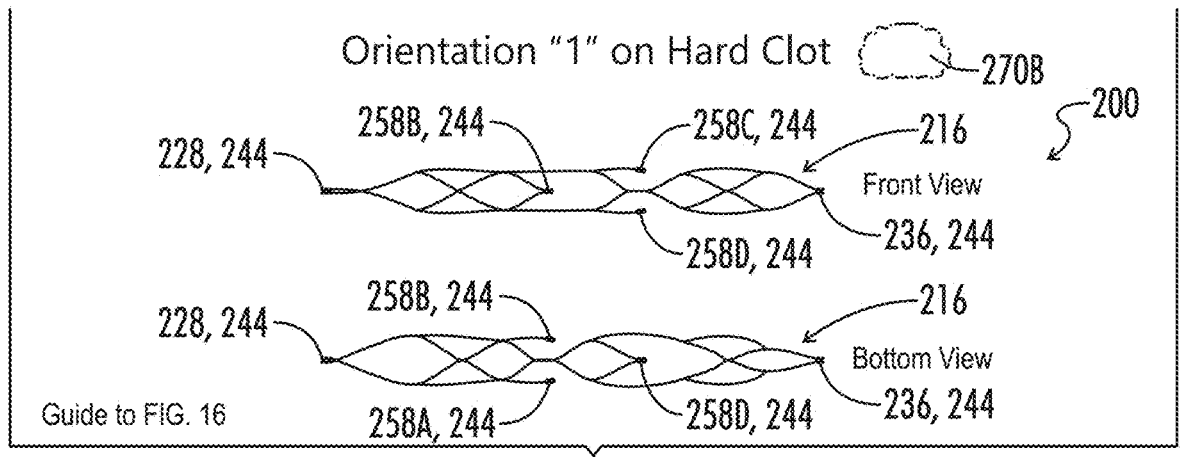
FIGS. 16A-H illustrate stepwise use of the distal body of FIG. 11 in retrieving a hard clot; the distal body is in Orientation 1.
Figure 16B:
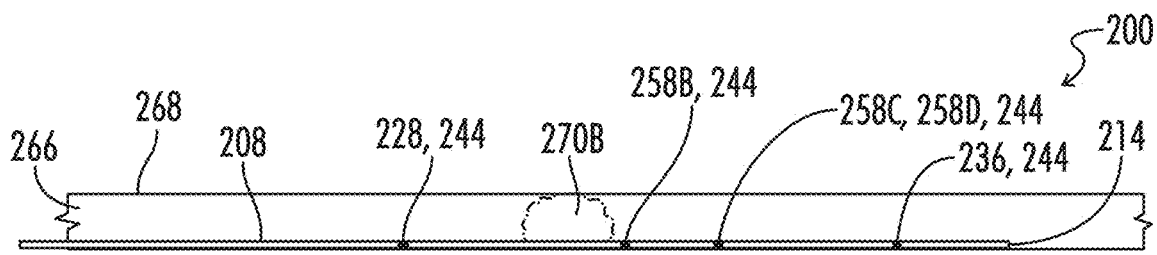
Figure 16C:
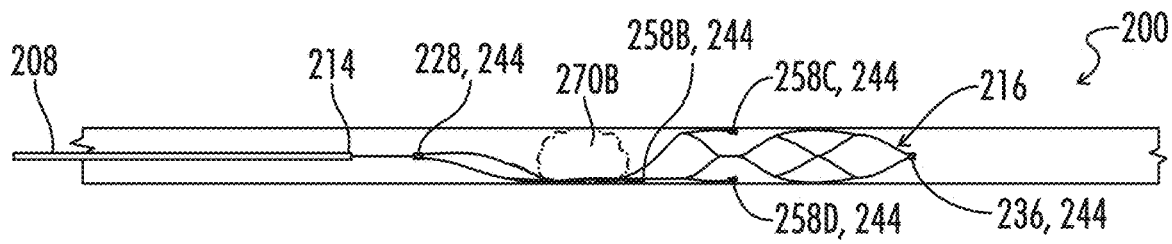
Figure 16D:
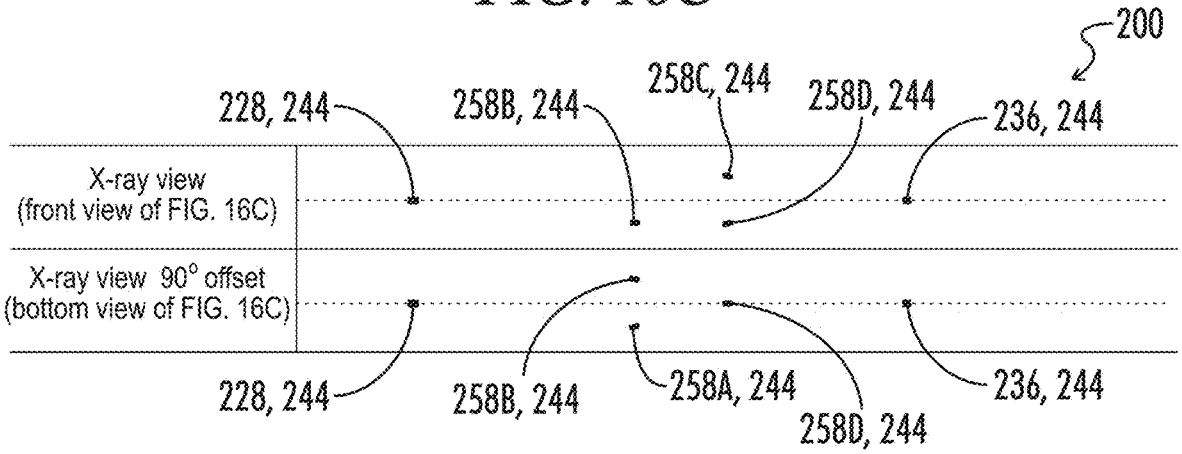
Figure 16E:
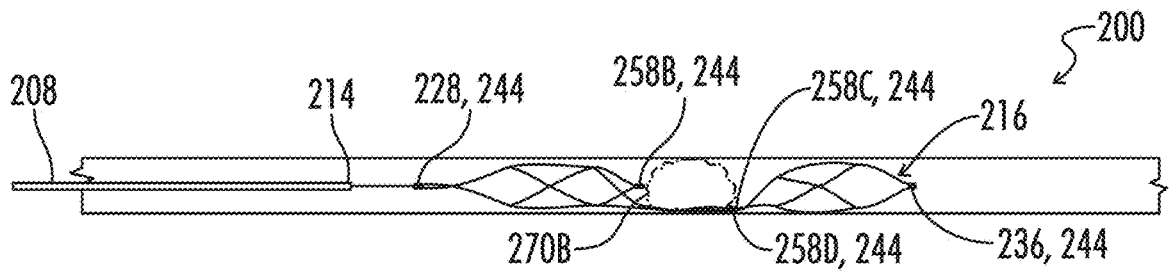
Figure 16F:
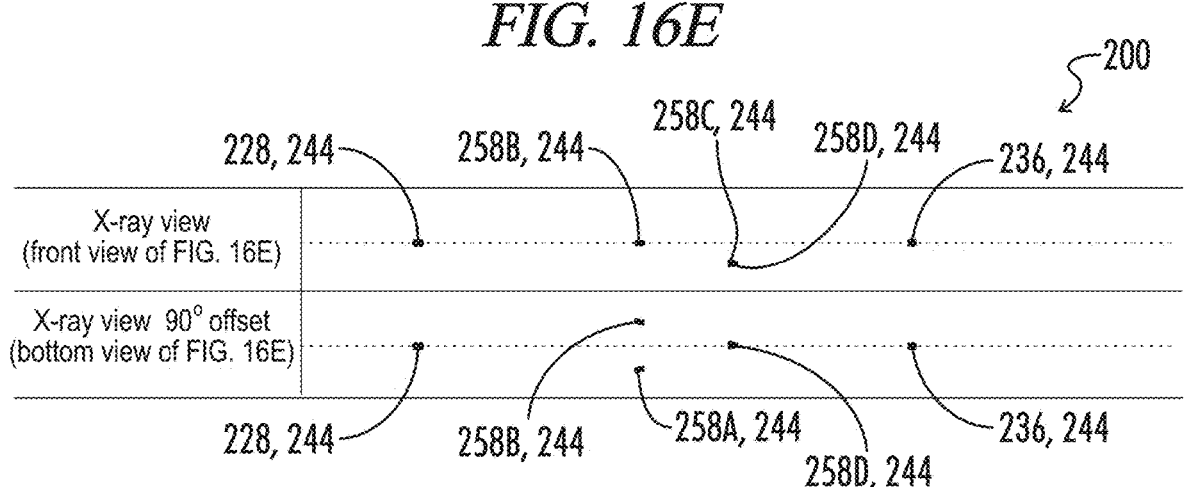
Figure 16G:
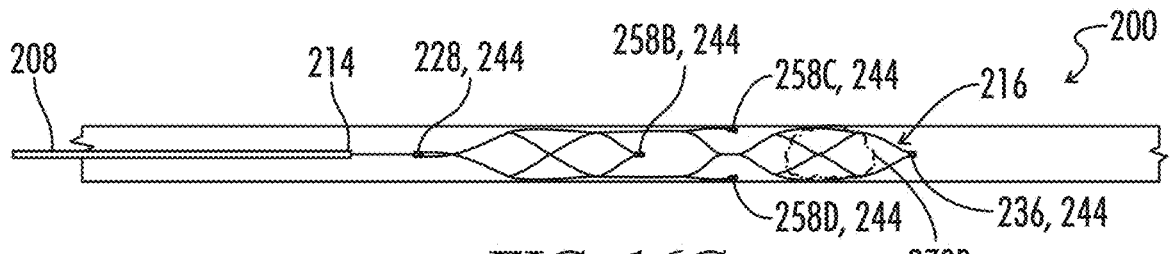
Figure 16H:
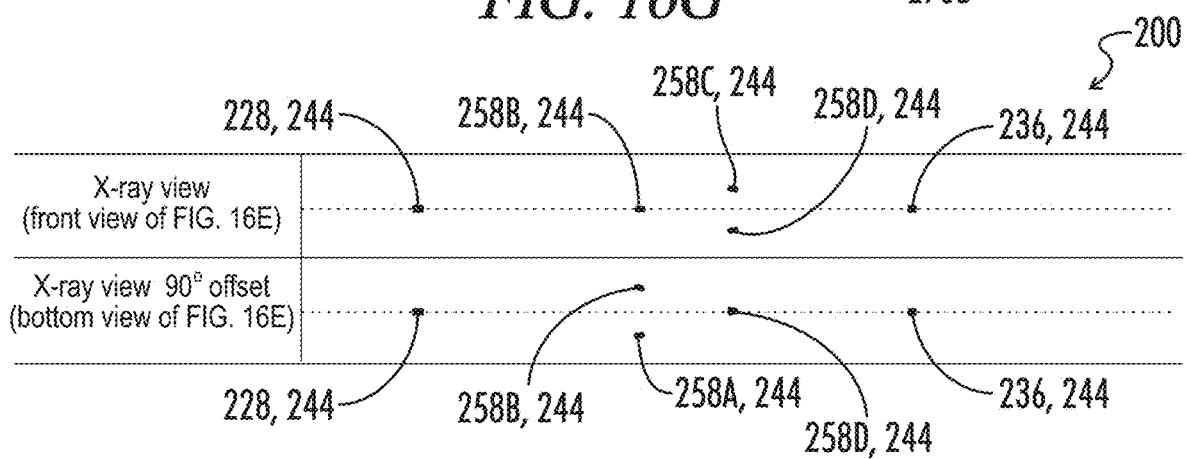

FIGS. 16A-H illustrate stepwise use of the distal body 216 in retrieving a hard clot 270B in a human intracranial artery 266. (In FIGS. 16A-H, the distal body 216 is in Orientation 1). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 16B. The distal body 216 is then deployed from the delivery catheter 208 by moving the catheter 208 proximally. The hard clot 270B, which is located above the distal body 216, collapses the distal body 216, as shown in FIG. 16C. However, at this time, the surgeon is unaware that the clot 270B has collapsed the distal body 216. Thus, without moving the distal body 216, the surgeon irradiates the x-ray markers at a first vantage point (i.e., from the front of the distal body 216; i.e., into the page). As shown in FIG. 16D, the first vantage point shows four rows of x-ray markers. The first row is, as always, a single point, representing the x-ray marker located in the proximal tube—i.e., 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row is hidden from view on the x-ray at this angle—rather, one marker 258C, 244 is located above the other marker 258D, 244—and as shown in FIG. 16C, the distal body 216 is not collapsed at the distal, unattached distal-pointing crowns 258C, 244 and 258D, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has two points, which represents the two x-ray markers located at the proximal, unattached distal-pointing crowns 258A, 244 and 258B, 244; the reason that this second row of markers shows up as two points is that neither marker in the second row is hidden from view on the x-ray at this offset angle—rather, one marker 258B, 244 is located above the other marker 258A, 244—and although the distal body 216 is collapsed at the proximal, unattached distal-pointing crowns as shown in FIG. 16C, the second row of x-ray markers have not converged because the clot 270B is on top of the second row of x-ray markers. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the second row 258A, 244 and 258B, 244 nor the third row 258C, 244 and 258D, 244 of x-ray markers (i.e., the x-ray markers at both the proximal and distal unattached distal pointing-crowns) has converged. As shown in FIG. 16E, the surgeon then moves the distal body 216 proximally so that the distal, unattached distal-pointing crowns 258C, 244 and 258D, 244 are immediately distal to the clot 270B and the surgeon then irradiates the x-markers again from the first vantage point. As shown in FIG. 16F, the first row is, as always, a single point, representing the x-ray marker located in the proximal tube 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has only one point because the clot 270B, which is on top of the third row of x-ray markers 258C, 244 and 258D, 244 (i.e., the markers at the distal, unattached distal-pointing crowns), has pushed the third row of x-ray markers 258C, 244 and 258D, 244 together. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker in the second row is hidden from view on the x-ray at this offset angle and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the bottom x-ray marker of the third row 258D, 244 is directly in front of the top x-ray marker of the third row 258C, 244, and thus, the top x-ray marker of the third row 258C, 244 is hidden from view. The fourth row is, as always, a single point, which represents the x-ray marker located in the distal tube 236, 244. Knowing that the distal, unattached distal-pointing crowns 258C, 244 and 258D, 244 have converged as shown in FIG. 16F, the surgeon moves the distal body 216 proximally and the hard clot 270B falls into the distal body interior 222 in the enlarged cell/drop zone 262C immediately distal to the top, distal, unattached distal-pointing crown 258C. See FIG. 16G. To confirm that the hard clot 270B has entered the distal body interior 222, the surgeon takes x-rays from the first and second vantage points. The results are shown in FIG. 16H. As compared to 16F, the front x-ray view of FIG. 16H shows that the distal, unattached distal-pointing crowns 258C, 244 and 258D, 244 are not converged, and, thus, the surgeon concludes that the hard clot 270B has entered the distal body interior 222. The surgeon then removes the distal body 216 and the hard clot 270B, captured by the distal body 216, by moving the distal body 216 proximally out of the vessel 266.

Figure 17A:
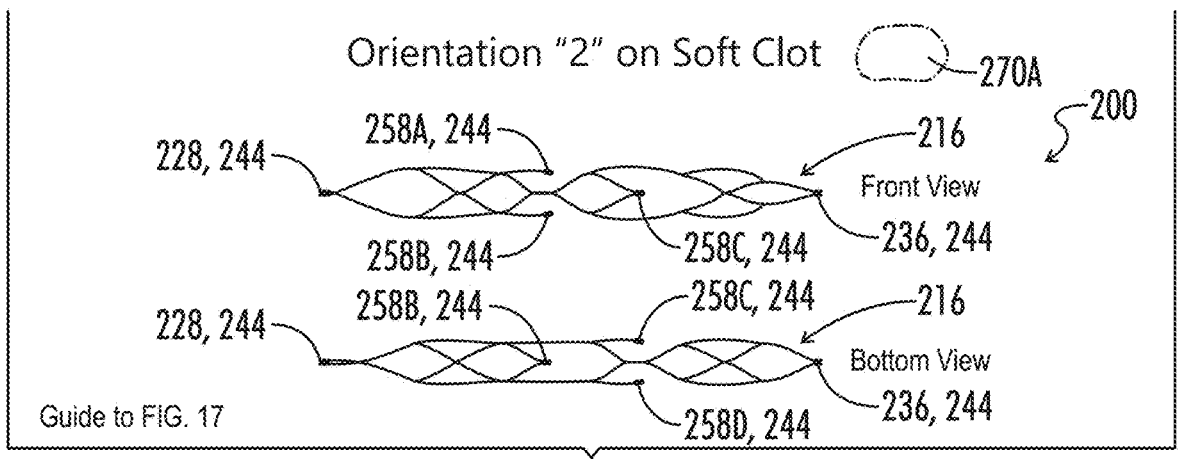
FIGS. 17A-G illustrate stepwise use of the distal body of FIG. 11 in retrieving a soft clot; the distal body is in Orientation 2.
Figure 17B:
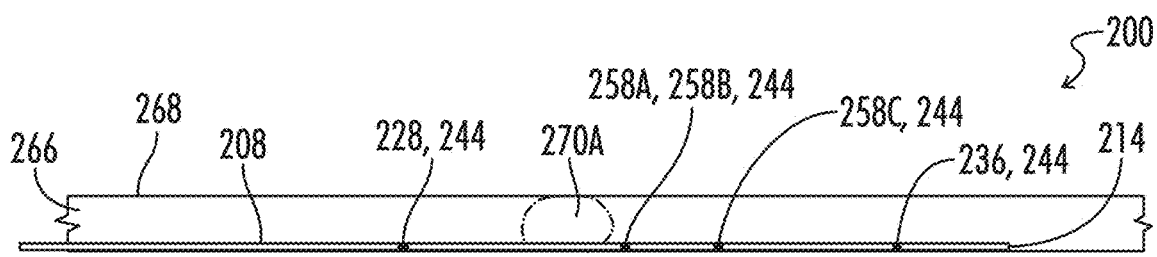
Figure 17C:
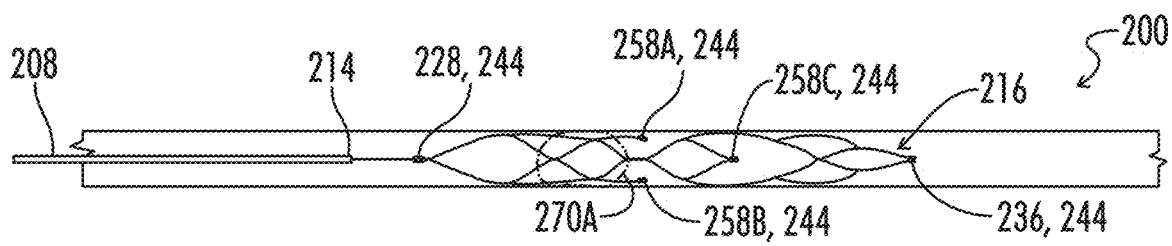
Figure 17D:
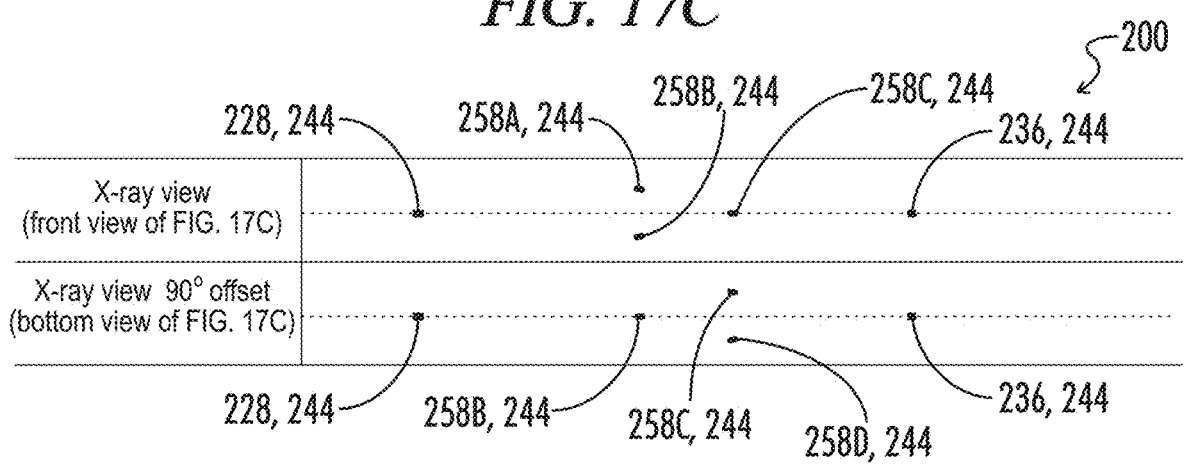
Figure 17E:
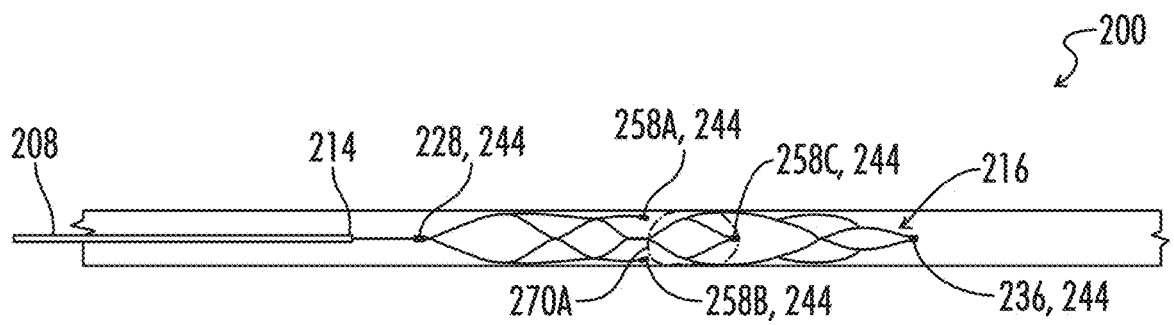
Figure 17F:
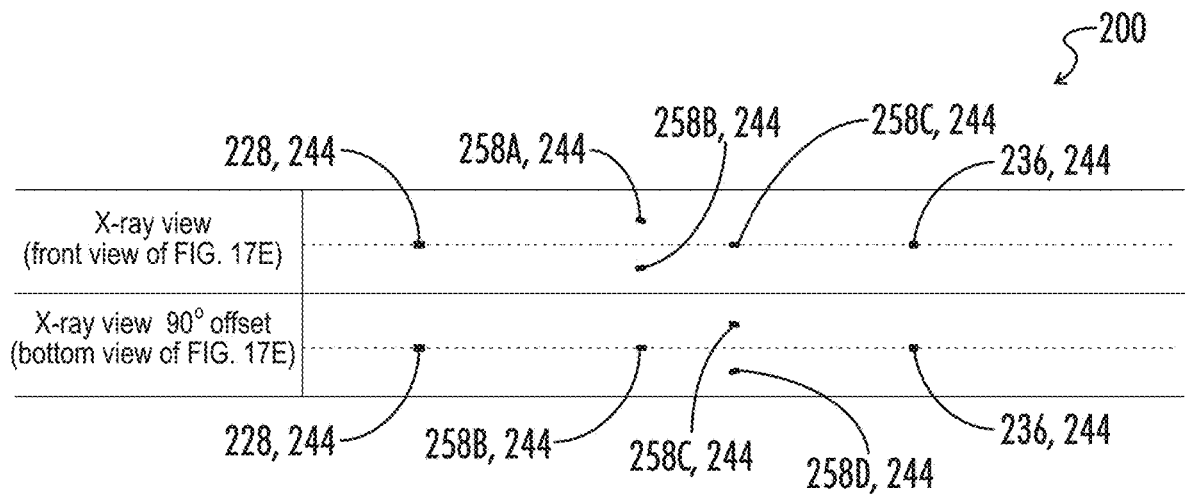
Figure 17G:
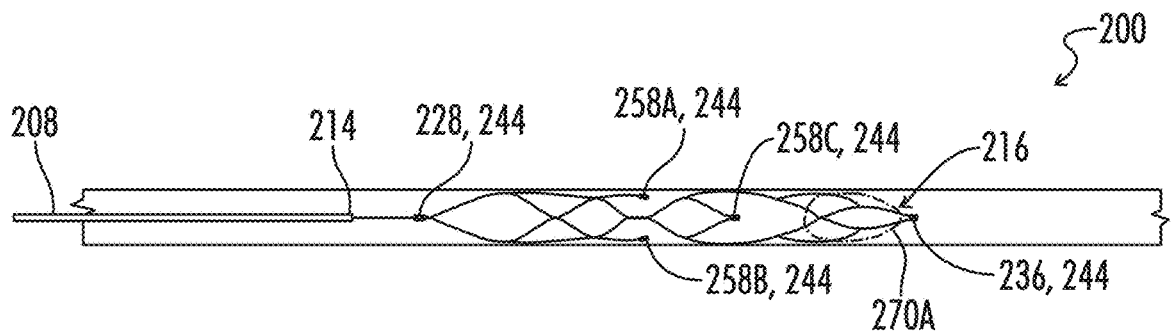

FIGS. 17A-G illustrate stepwise use of the distal body 216 in retrieving a soft clot 270A in a human intracranial artery 266. (In FIGS. 17A-G, the distal body 216 is in Orientation 2). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 17B. The distal body 216 is then deployed from the catheter 208 by moving the catheter 208 proximally. The soft clot 270A, which is unable to collapse the distal body 216, then enters the distal body interior 222. See FIG. 17C. However, at this time, the surgeon is unaware that the clot 270A has entered into the distal body interior 222. Thus, without moving the distal body 216, the surgeon irradiates the x-ray markers at a first vantage point (i.e., from the front of the distal body; into the page). As shown in FIG. 17D, the first vantage point shows four rows of x-ray markers. The first row is, as always, a single point, representing the x-ray marker located in the proximal tube 228, 244. The second row has two points, which represents the two x-ray markers located at the proximal, unattached distal-pointing crowns 258A, 244 and 258B, 244; the reason that this second row of markers has two points is that neither marker in the second row is hidden from view on the x-ray at this angle—rather, one marker 258A, 244 is located above the other marker 258B, 244— and as shown in FIG. 17C, the distal body 216 is not collapsed at the proximal, unattached distal-pointing crowns 258A, 244 and 258B, 244. The third row has a single point, which represents the x-ray marker located at the front (in Orientation 2), distal, unattached distal-pointing crown 258C, 244; the reason that this third row of markers is a single point is that the rear (in Orientation 2) x-ray marker 258D, 244 of the third row is hidden from view because it is directly behind the front x-ray marker 258C, 244 of the third row. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body, as shown in this view). As shown, the first row is, as always, a single point, which represents the x-ray marker located in the proximal tube 228, 244. The second row is a single point, which represents the x-ray marker located at the bottom (in Orientation 2), proximal, unattached distal-pointing crown 258B, 244; the reason that this second row of markers is a single point is that the top (in Orientation 2) x-ray marker of the second row 258A, 244 is directly behind the bottom x-ray marker of the second row 258B, 244, and thus, hidden from view. The third row has two points, which represents the two x-ray markers located at the distal, unattached distal-pointing crowns 258C, 244 and 258D, 244; the reason that this third row of markers shows up as two points is that neither marker in the third row is hidden from view on the x-ray at this offset angle and the distal body 216 is not collapsed at the distal, unattached distal-pointing crowns 258C, 244 and 258D, 244. The fourth row is, as always, a single point, which represents the x-ray marker located in the distal tube 236, 244. The surgeon, thus, concludes that neither the second row 258A, 244 and 258B, 244 nor the third row of x-ray markers 258C, 244 and 258D, 244 (i.e., the x-ray markers at both the proximal and distal unattached distal pointing-crowns) has converged. As shown in FIG. 17E, the surgeon then moves the distal body 216 proximally relative to the clot 270A so that the distal, unattached distal-pointing crowns 258C, 244 and 258D, 244 are immediately distal to the clot 270A and then the surgeon irradiates the x-markers again from the first vantage point and the second vantage point. As shown in FIG. 17F, the results are the same as FIG. 17D. With the results from FIGS. 17D and 17F, the surgeon concludes that neither the second row 258A, 244 and 258B, 244 nor the third row of x-ray markers 258C, 244 and 258D, 244 (i.e., the x-ray markers at both the proximal and distal unattached distal pointing-crowns) were converged at either the original position of the distal body 216 (FIGS. 17C and 17D) or the position after moving the distal body 216 proximally (FIGS. 17E and 17F), and, thus, the distal body 216 was expanded in the vessel 266 in both positions. Thus, the surgeon concludes that the clot 270A is a soft clot 270A that has entered into the distal body interior 222 and the surgeon removes the distal body 216 and the soft clot 270A, captured by the distal body 216, by moving the distal body 216 proximally out of the vessel 266, as shown in FIG. 17G.

FIGS. 18A-G illustrate stepwise use of the distal body 216 in retrieving a hard clot 270B in a human intracranial artery 266. (In FIGS. 18A-G, the distal body 216 is in Orientation 2). (As described below, the primary differences between FIGS. 18A-G and FIGS. 16A-G is that the clot 270B enters the distal body interior 222 in an enlarged cell/drop zone 262A immediately distal to one of the proximal, unattached distal-pointing crowns 258A in FIGS. 18A-G, as compared to FIGS. 16A-G where the clot 270B enters the distal body interior 222 in an enlarged cell/drop zone 262C immediately distal to one of the distal, unattached distal-pointing crowns 258C). First, as always, the surgeon determines the location of the clot 270B in the vessel 266 using, for example, a contrast dye injected proximal and distal to the clot 270B.

Figure 18A:
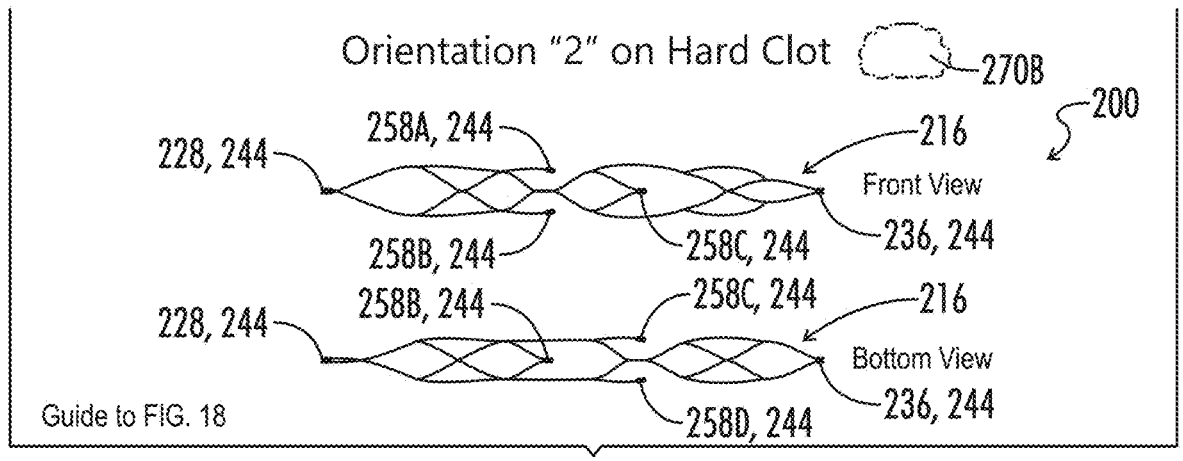
FIGS. 18A-G illustrate stepwise use of the distal body of FIG. 11 in retrieving a hard clot; the distal body is in Orientation 2.
Figure 18B:
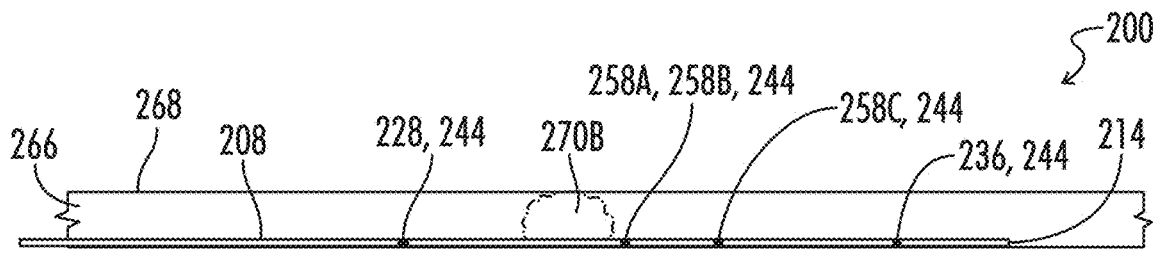
Figure 18C:
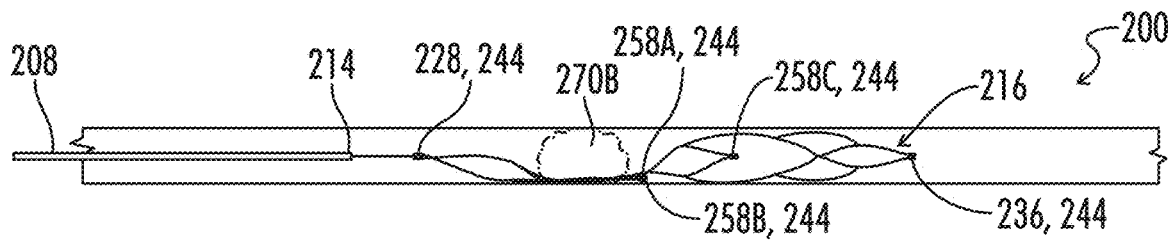
Figure 18D:
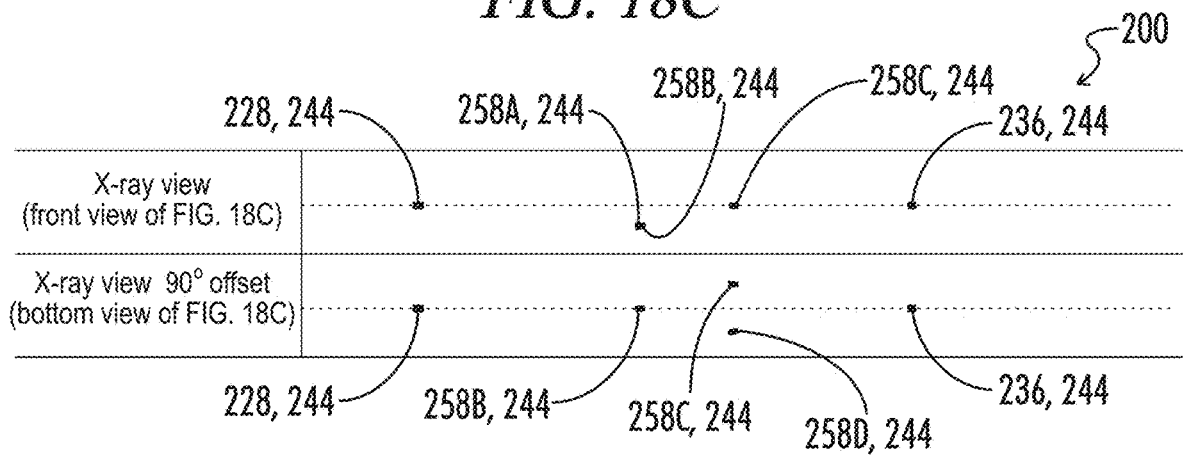
Figure 18E:
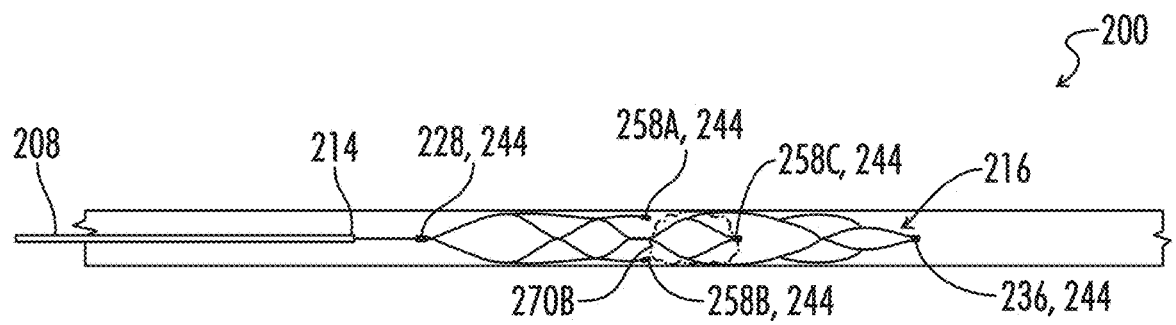
Figure 18F:
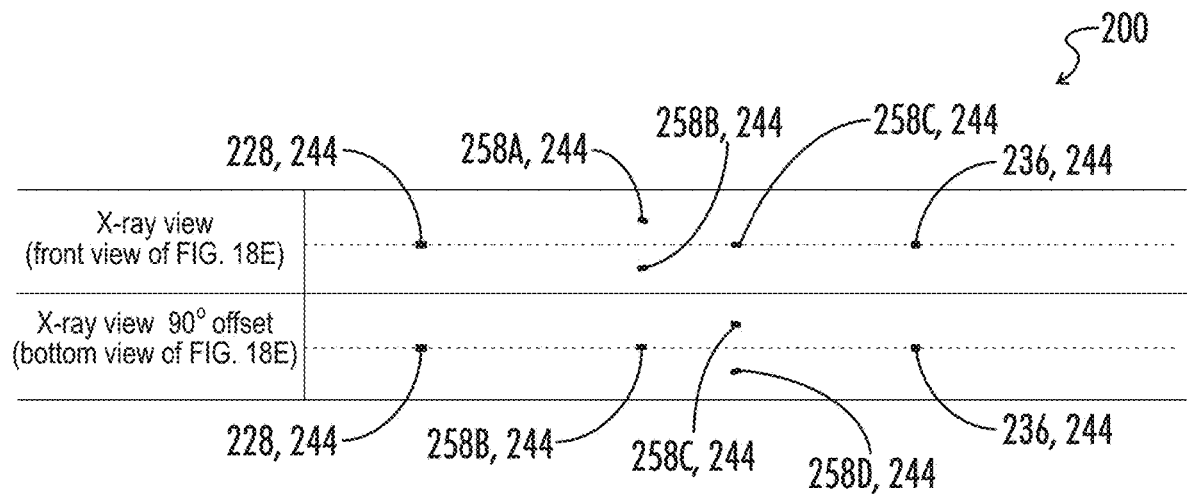
Figure 18G:
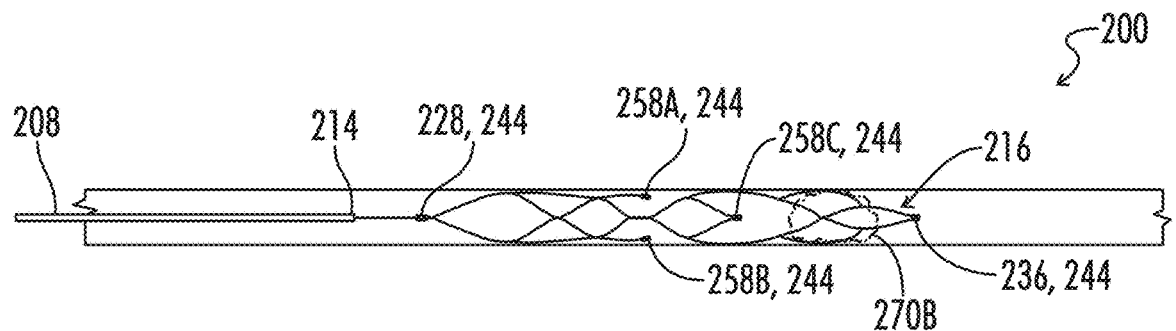

Next, the delivery catheter 208, which is enveloping the distal body 216, is positioned in the blood vessel 266 so that the two proximal, unattached distal-pointing crowns 258A and 258B are immediately distal to the clot 270B. See FIG. 18B. The distal body 216 is then deployed from the catheter 208 by moving the catheter 208 proximally. The hard clot 270B, which is located above the distal body 216, collapses the distal body 216, as shown in FIG. 18C. However, at this time, the surgeon is unaware that the clot 270B has collapsed the distal body 216. Thus, without moving the distal body 216, the surgeon irradiates the x-ray markers at a first vantage point (i.e., from the front of the distal body in Orientation 2; into the page). As shown in FIG. 18D, the first vantage point shows four rows of x-ray markers. The first row is, as always, a single point, representing the x-ray marker located in the proximal tube 228, 244. The second row has only one point because the clot 270B, which is on top of the second row of x-ray markers 258A, 244 and 258B, 244 (i.e., the markers at the proximal, unattached distal-pointing crowns), has pushed them together. The third row has only one point, which represents the x-ray marker located at the front (in Orientation 2), proximal, unattached distal-pointing crown 258C, 244; the reason that this third row of markers is a single point is that the rear (in this view) x-ray marker of the third row 258D, 244 is hidden from view because it is directly behind the front x-ray marker of the third row 258C, 244. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the top (in Orientation 2) x-ray marker of the second row 258A, 244 is located behind the bottom (in Orientation 2) x-ray marker 258B, 244 and thus, the top x-ray marker of the second row 258A, 244 is hidden from view. The third row has two points, which represents the x-ray markers located at the distal, unattached distal-pointing crowns 258C, 244 and 258D, 244; in this x-ray view neither of the x-ray markers of the third row is hidden from view. The fourth row is, as always, a single point, which represents the x-ray marker located in the distal tube 236, 244. The surgeon, thus, concludes that the second row of x-ray markers 258A, 244 and 258B, 244 (i.e., the x-ray markers at the proximal, unattached distal pointing-crowns) has converged. As shown in FIG. 18E, the surgeon then moves the distal body 216 proximally so that the distal, unattached distal-pointing crowns 258C, 244 and 258D, 244 are immediately distal to the clot 270B. Unbeknownst to the surgeon, the clot 270B enters the distal body interior 222 immediately distal to the top (in Orientation 2), proximal unattached distal-pointing crown 258A and the distal body 216 is no longer collapsed. The surgeon then irradiates the x-markers again from the first vantage point. As shown in FIG. 18F, the first row is, as always, a single point, representing the x-ray marker located in the proximal tube 228, 244. The second row has two x-ray markers because the distal body 216 is not collapsed and neither the top (in Orientation 2) 258A, 244 nor the bottom 258B, 244 (in Orientation 2) x-ray marker of the second row (i.e., the marker at the proximal, unattached distal-pointing crowns) is hidden from view. The third row has only one point because the rear (in Orientation 2), distal unattached distal-pointing crown 258D, 244 is hidden behind the front (in Orientation 2), distal, unattached distal pointing-crown 258C, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the x-ray marker at the top (in Orientation 2), proximal, unattached distal-pointing crown 258A, 244 is hidden behind the bottom (in Orientation 2), proximal, unattached-distal pointing crown 258B, 244. The third row has two points because neither the front nor the rear x-ray markers at the distal, unattached, distal-pointing crowns 258C, 244 and 258D, 244 is hidden from view. The fourth row is, as always, a single point, which represents the x-ray marker located in the distal tube 236, 244. Based on the information from FIGS. 18D and 18F, the surgeon concludes that the clot 270B has entered into the distal body interior 222. The surgeon then removes the distal body 216 and the hard clot 270B, captured by the distal body 216, by moving the distal body 216 proximally out of the vessel 266, as shown in FIG. 18G. Upon comparing FIGS. 16A-G and FIGS. 18A-G it will be appreciated that the orientation of the enlarged cells/drop zone 262A-D relative to the orientation of a hard clot 270B determine which enlarged cell/drop zone 262A, 262B, 262C, or 262D, the hard clot 270 enters the distal body interior 222 through. For example, in FIG. 16C, the hard clot 270B is located above the distal body 216, and thus, the hard clot 270B must enter through the enlarged cell/drop zone located at the top of the distal body, which in the orientation of the distal body shown in FIGS. 16A-G, is the enlarged cell/drop zone 262C immediately distal to the top, distal, unattached, distal-pointing crown 258C. In FIG. 18C, the hard clot 270B is again located above the distal body and, thus, the hard clot 270B must enter through the enlarged cell/drop zone located at the top of the distal body. However, in FIG. 18C, the enlarged cell/drop zone located at the top of the distal body 216, in the orientation of the distal body 216 shown in FIGS. 18A-G, is the enlarged cell/drop zone 262A immediately distal to the top, proximal, unattached, distal-pointing crown 258A.

Figure 19A:
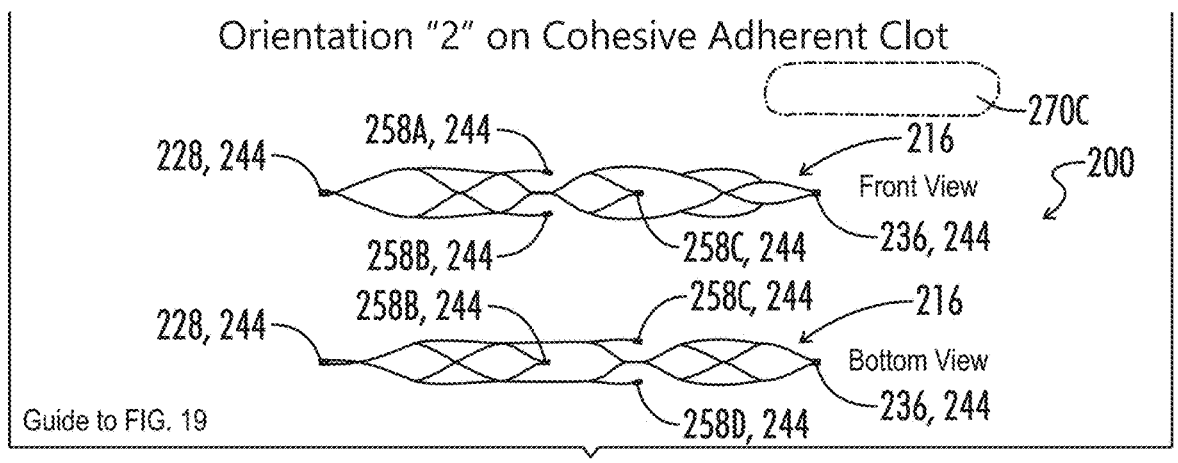
FIGS. 19A-N illustrate stepwise use of the distal body of FIG. 11 in retrieving a deformable, cohesive adherent clot; the distal body is in Orientation 2.
Figure 19B:
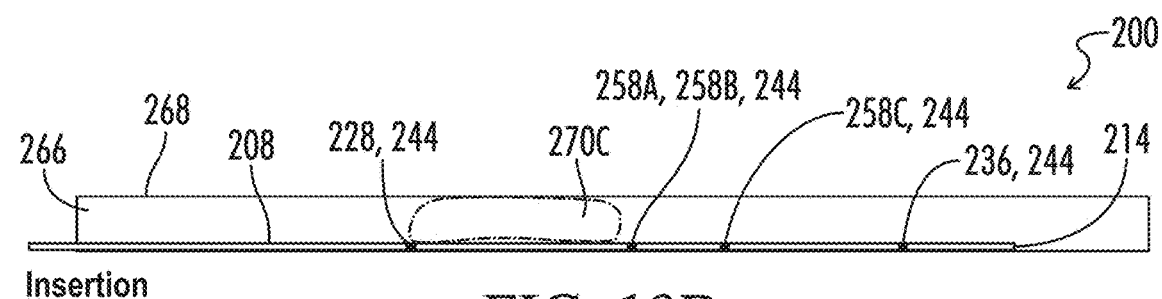
Figure 19C:
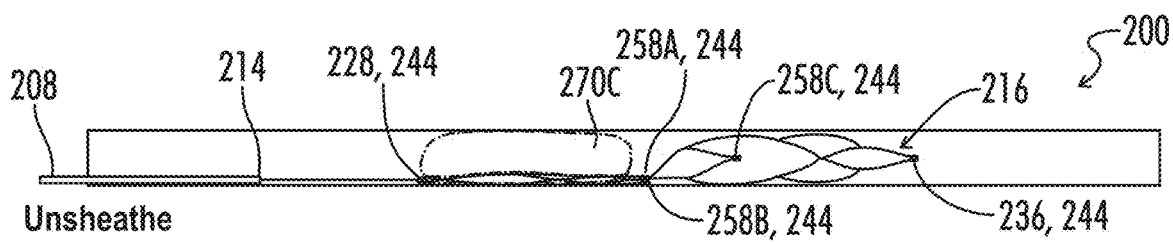
Figure 19D:
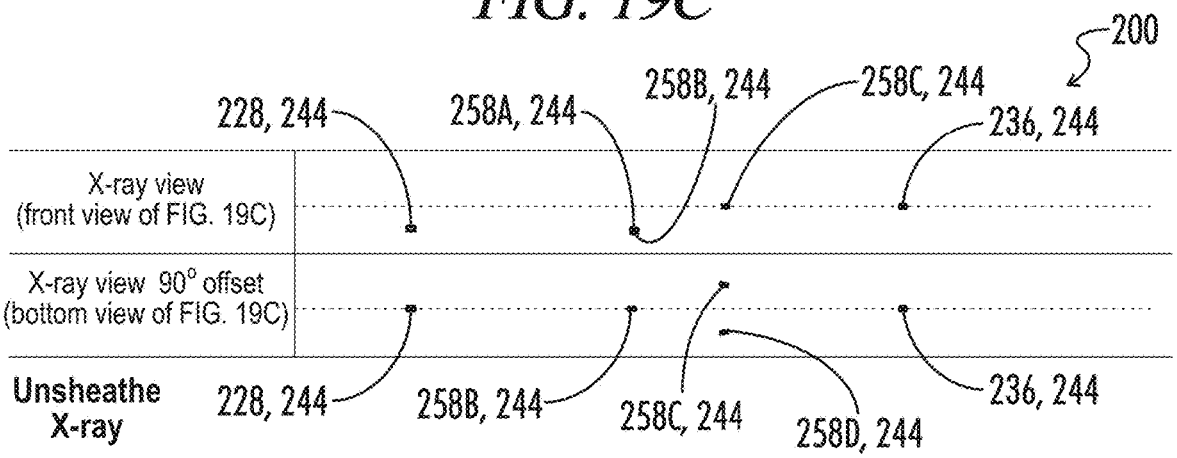
Figure 19E:
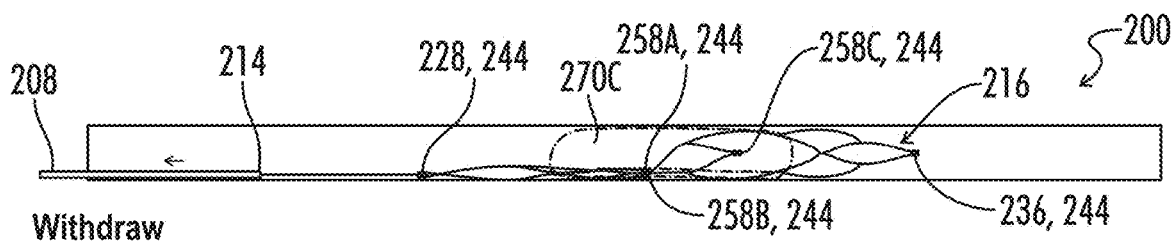
Figure 19F:
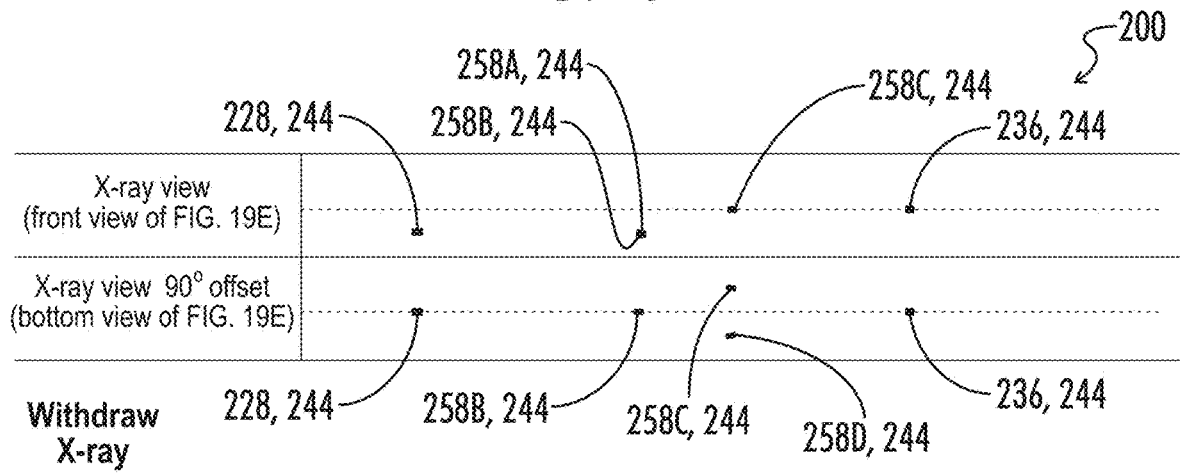
Figure 19G:
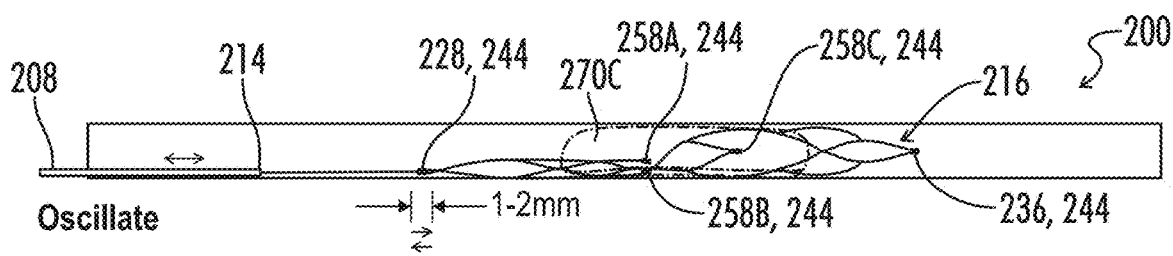
Figure 19H:
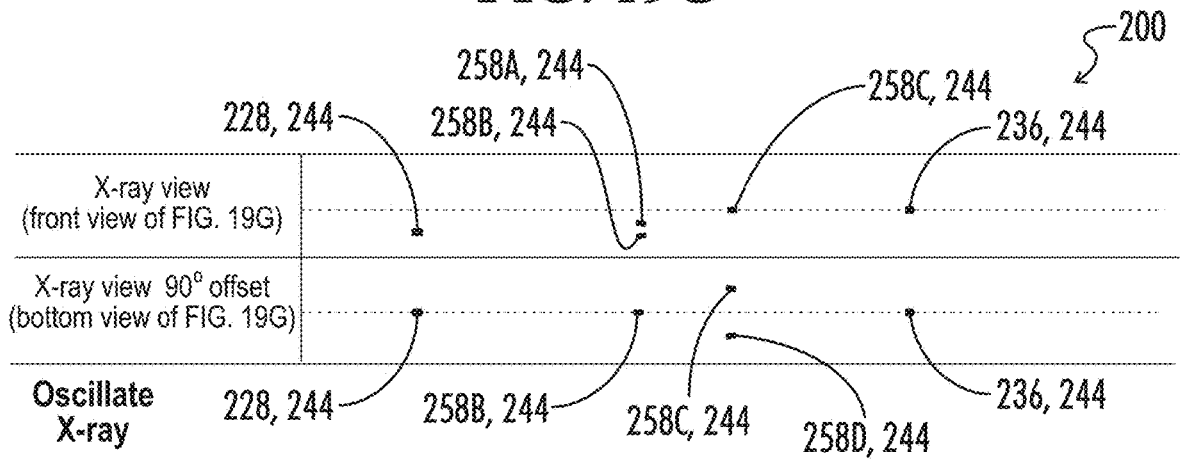
Figure 19I:
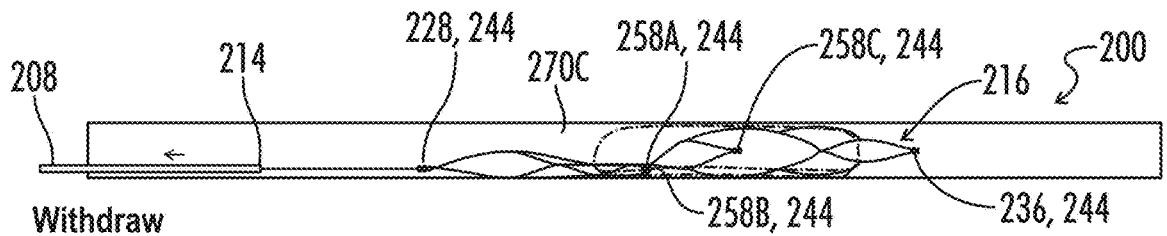
Figure 19J:
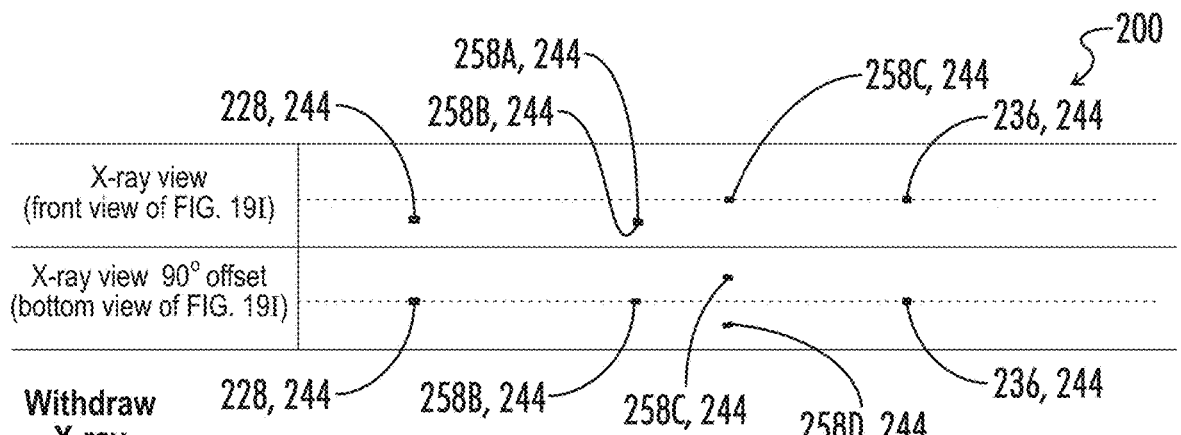
Figure 19K:
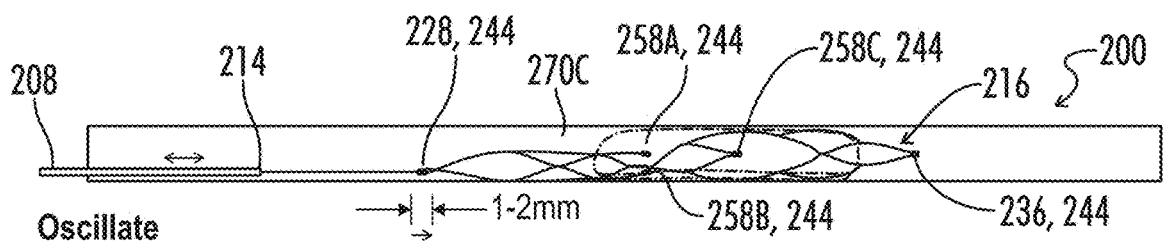
Figure 19L:
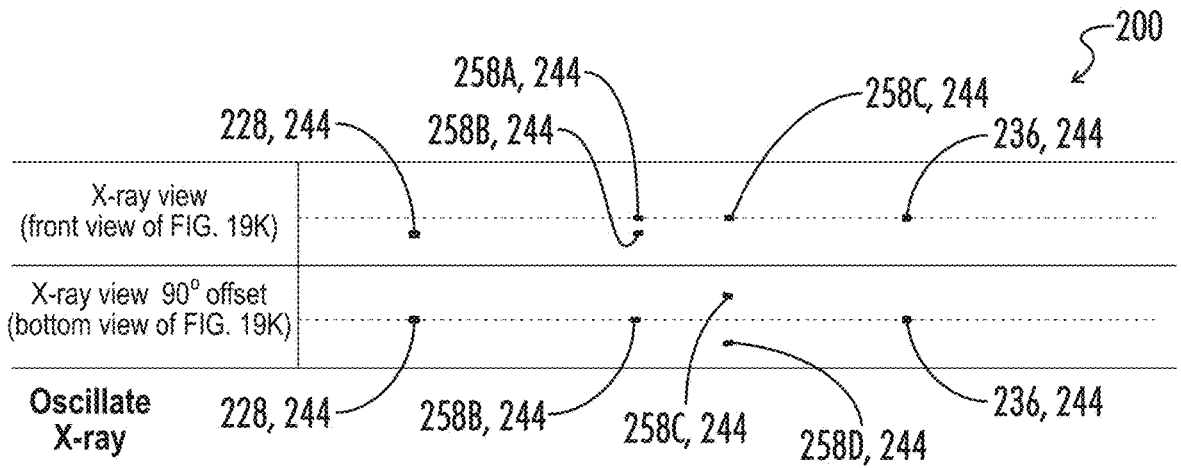
Figure 19M:
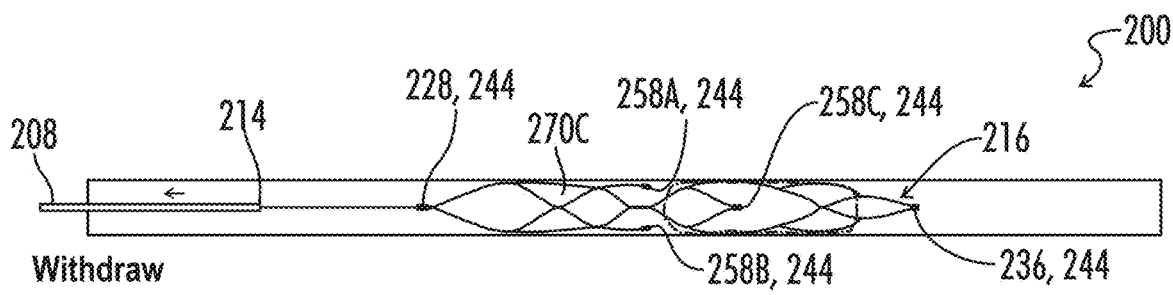
Figure 19N:
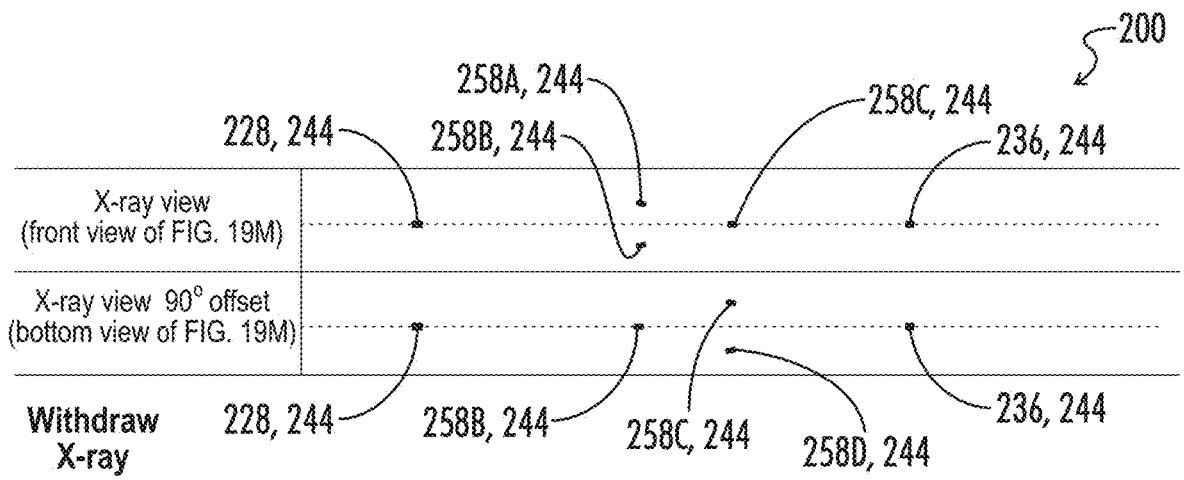

FIGS. 19A-N illustrate stepwise use of the distal body 216 in retrieving a deformable cohesive, adherent clot 270C—i.e., a clot that is difficult to break up and is tightly adhered to the vessel wall 268—in a human intracranial artery 266. (In FIGS. 19A-N, the distal body 216 is in Orientation 2). First, as always, the surgeon determines the location of the clot 270C in the vessel 266 using, for example, a contrast dye injected proximal and distal to the clot 270C. Next, the delivery catheter 208, which is enveloping the distal body 216, is positioned in the blood vessel 266 so that the two proximal, unattached distal-pointing crowns 258A and 258B are immediately distal to the clot 270C. See FIG. 19B. The distal body 216 is then deployed from the catheter 208 by moving the catheter 208 proximally. The deformable, cohesive adherent clot 270C, which is located above the distal body 216, collapses the distal body 216, as shown in FIG. 19C. However, at this time, the surgeon is unaware that the clot 270C has collapsed the distal body 216. Thus, without moving the distal body 216, the surgeon irradiates the x-ray markers at a first vantage point (i.e., from the front of the distal body; i.e., into the page). As shown in FIG. 19D, the first vantage point shows four rows of x-ray markers. The first row is, as always, a single point, representing the x-ray marker located in the proximal tube 228, 244. The second row has a single point, corresponding to the top (in Orientation 2) and bottom (in Orientation 2), proximal, unattached distal-pointing crowns 258A, 244 and 258B, 244, which have converged because the clot 270C is collapsing the distal body 216. The third row has a single point, which represents the x-ray marker located at the front (in Orientation 2), distal, unattached distal-pointing crown 258C, 244; the x-ray marker located at the rear, distal, unattached distal-pointing crown 258D, 244 is hidden from view. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has a single point, which corresponds to the bottom (in Orientation 2), proximal, unattached distal-pointing crown 258B, 244; the top (in Orientation 2), proximal, unattached distal-pointing crown 258A, 244 is located behind the bottom, proximal, unattached distal-pointing crown 258B, 244 and hidden from view. The third row has two points, which correspond to the front (in Orientation 2) 258C, 244 and rear 258D, 244 (in Orientation 2), distal, unattached distal-pointing crowns, neither of which is blocked in this view. The fourth row is, as always, a single point, which represents the x-ray marker located in the distal tube 236, 244. As shown in FIG. 19E, the surgeon then moves the distal body 216 proximally (i.e., slightly withdraws the distal body 216). The surgeon then irradiates the x-markers again from the first and second vantage points. As shown in FIG. 19F, the results are exactly the same as in FIG. 19D. Based on the observation that the proximal, unattached distal-pointing crowns 258A, 244 and 258B, 244 have converged at both the original position (FIGS. 19C and 19D in which the proximal, unattached distal-pointing crowns 258A, 244 and 258B, 244 are immediately distal to the clot 270C) and the second position (FIGS. 19E and 19F), the surgeon concludes that the clot 270C is a deformable cohesive, adherent clot 270C. The surgeon then oscillates the distal body 216 proximally and distally a small distance (e.g., about 1 mm to about 2 mm) in the vessel 266, and the clot 270C begins to enter the distal body 216, as shown in FIG. 19G. The surgeon then irradiates the x-markers again from the first and second vantage points. As shown in FIG. 19H, the results are exactly the same as in FIG. 19D and FIG. 19F except that the second row of markers 258A, 244 and 258B, 244 (at the proximal, unattached distal-pointing crowns) are beginning to move apart. The surgeon then moves the distal body 216 proximally again, as shown in FIG. 19I. The surgeon then irradiates the x-markers again from the first and second vantage points. As shown in FIG. 19J, the results are exactly the same as in FIGS. 19D and 19F, as the clot 270C has caused the second row of markers 258A, 244 and 258B, 244 to re-converge. The surgeon then oscillates the distal body 216 proximally and distally a small distance (e.g., about 1 mm to about 2 mm) in the vessel 266, and the clot 270C begins to further enter the distal body interior 222, as shown in FIG. 19K. The surgeon then irradiates the x-markers again from the first and second vantage points. As shown in FIG. 19L, the results are the same as in FIG. 19H. The surgeon then moves the distal body 216 again proximally, and, instead of collapsing the second row of markers 258A, 244 and 258B, 244, the clot 270C fully enters the distal body interior 222, as shown in FIG. 19M. The surgeon then irradiates the x-markers again from the first and second vantage points. As shown in FIG. 19N, the results show that the second row of markers 258A, 244 and 258B, 244 (at the proximal, unattached distal-pointing crowns) have moved apart. Satisfied that the x-ray markers in the second row 258A, 244 and 258B, 244 (at the proximal, unattached distal-pointing crowns) are sufficiently far apart and that the x-ray markers in the third row (at the distal, unattached distal-pointing crowns) 258C, 244 and 258D, 244 have stayed far apart, the surgeon concludes that the deformable cohesive, adherent clot 270C has been sufficiently captured by the distal body 216 and the surgeon then removes the distal body 216 and the clot 270C, captured by the distal body 216, by moving the distal body 216 proximally out of the vessel 266.

Several observations can be made from FIGS. 15-19, as indicated above. For example, the x-ray markers at the proximal and distal, unattached distal-pointing crowns 258A-D, 244 provide the surgeon feedback concerning the interaction between the distal body 216 and the clot 270 in the blood vessel 266. In addition, the guiding principle of a soft clot 270A is that the soft clot 270A does not collapse the distal body 216, and thus, x-ray markers at the proximal and distal, unattached distal-pointing crowns 258A-D, 244 always appear as two points except when a marker is hidden behind another marker (due to the view). When it comes to a hard clot 270B, the hard clot 270B is generally able to enter the distal body interior 222 without needing to oscillate the distal body 216 proximally and distally (unlike a deformable cohesive, adherent clot 270C). However, to capture the hard clot 270B, the hard clot 270B must be oriented properly relative to the enlarged cell/drop zones 262A, 262B, 262C, or 262D. (This is the reason that the distal body 216 has four enlarged cells/drop zones: one enlarged cells/drop zone at 0 degrees 262B, one enlarged cells/drop zone at 90 degrees 262C, one enlarged cells/drop zone at 180 degrees 262A and one enlarged cells/drop zone at 270 degrees 262D). As a guiding principle, an enlarged cell/drop zone 262A, 262B, 262C, or 262D is properly oriented to the clot 270B when the x-ray markers at the proximal, unattached distal-pointing crowns 258A, 244 and 258B, 244 or the distal, unattached distal pointing crowns 258C, 244 and 258D, 244 are together at both a first x-ray view and a second x-ray view 90 degrees relative to the first x-ray view, and the hard clot 270B can enter the enlarged cell/drop zone 262A, 262B, 262C, or 262D by moving the distal body 216 proximally. See FIGS. 16F and 18D. Finally, the guiding principal of retrieval of deformable cohesive, adherent clots 270C is that oscillation of the distal body 216 causes the deformable cohesive, adherent clots 270C to gradually enter the distal basket interior 222 over time.

Figure 21:
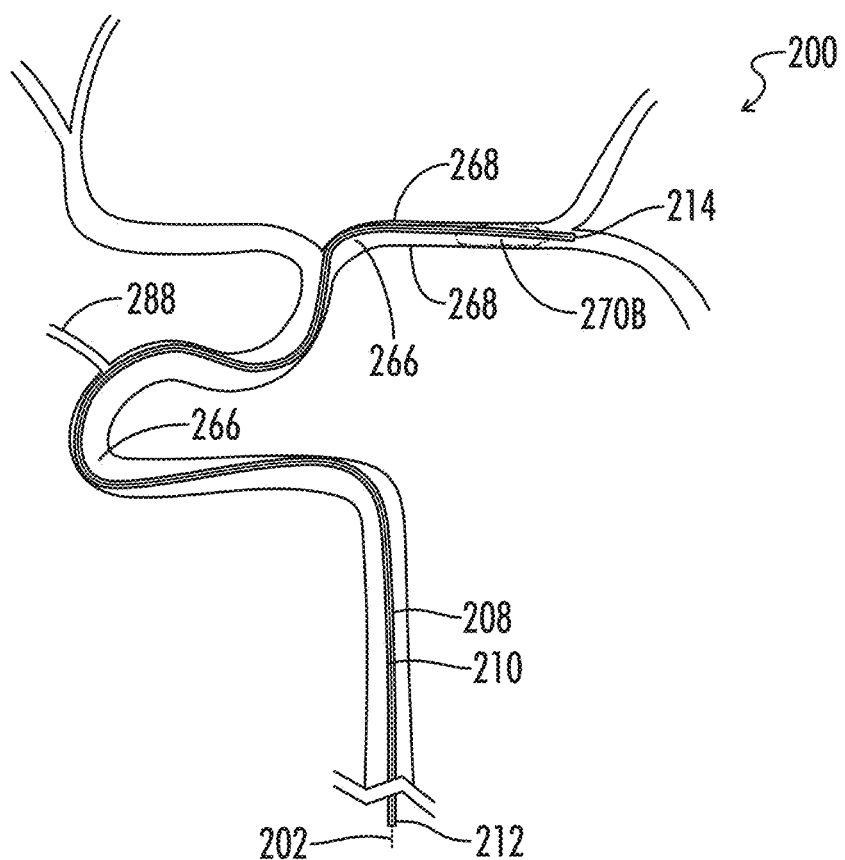
FIG. 21 shows a perspective view of a clot retrieval system that includes the distal body of FIGS. 20B-C being delivered in a blood vessel using a delivery catheter.
Figure 22:
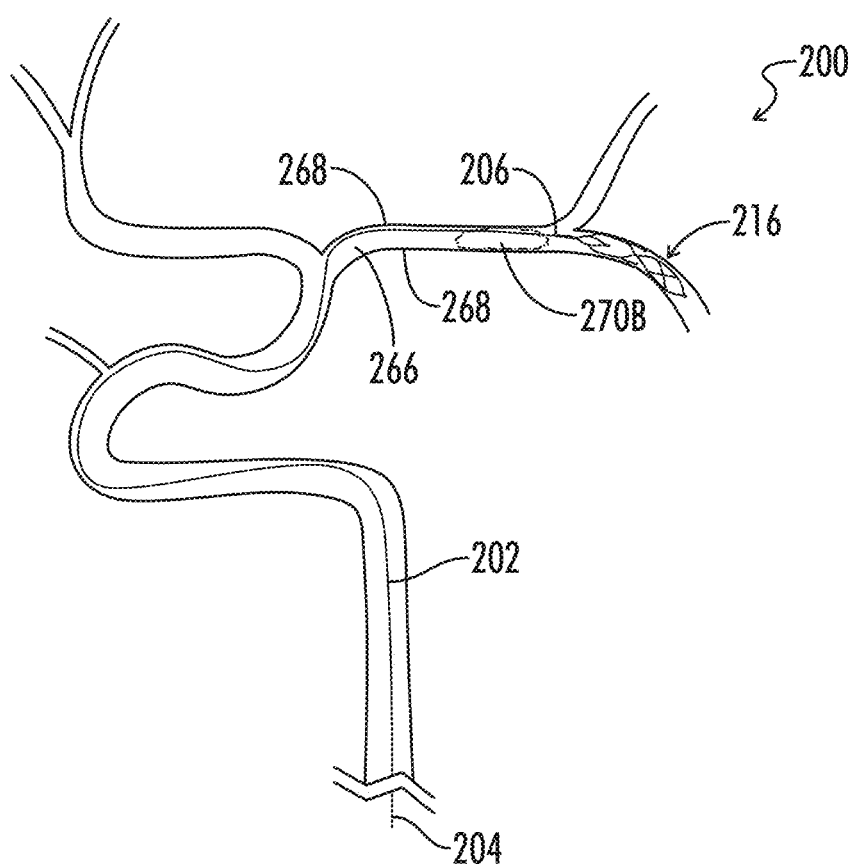
FIG. 22 shows a perspective view of the distal body of FIG. 21, after deployment of the distal body and retraction of the delivery catheter, in a blood vessel.
Figure 23:
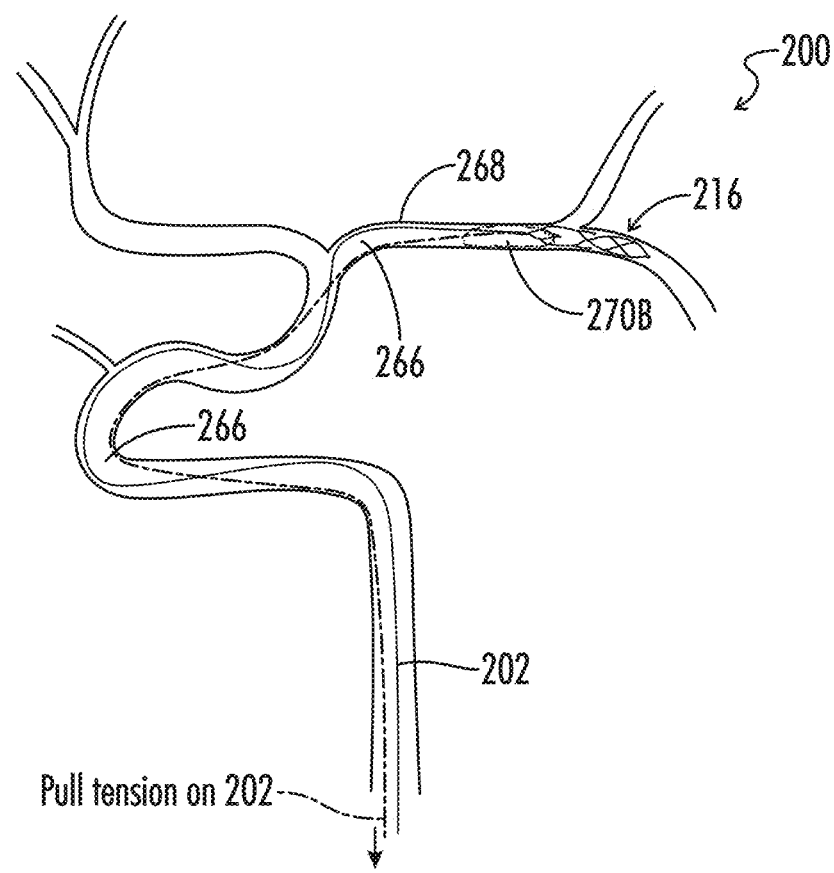
FIG. 23 shows a perspective view of the distal body of FIG. 21; as compared to FIG. 22, the distal body has been moved proximally and tension has been exerted on the pull wire.
Figure 24:
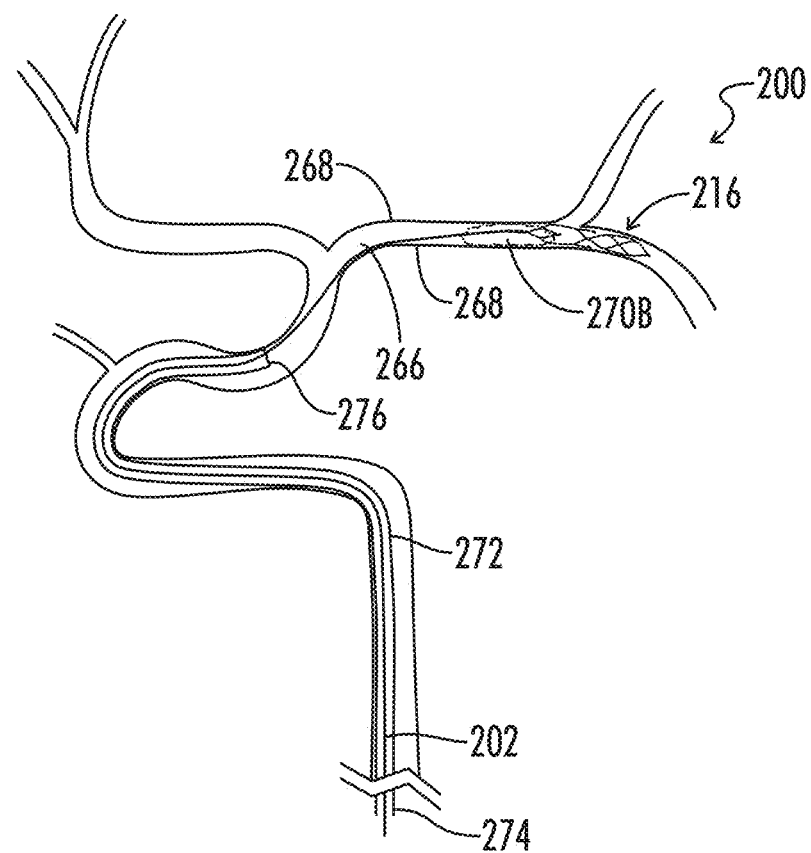
FIG. 24 shows a perspective view of a suction catheter that is being delivered over the pull wire of the system of FIG. 21.
Figure 25:
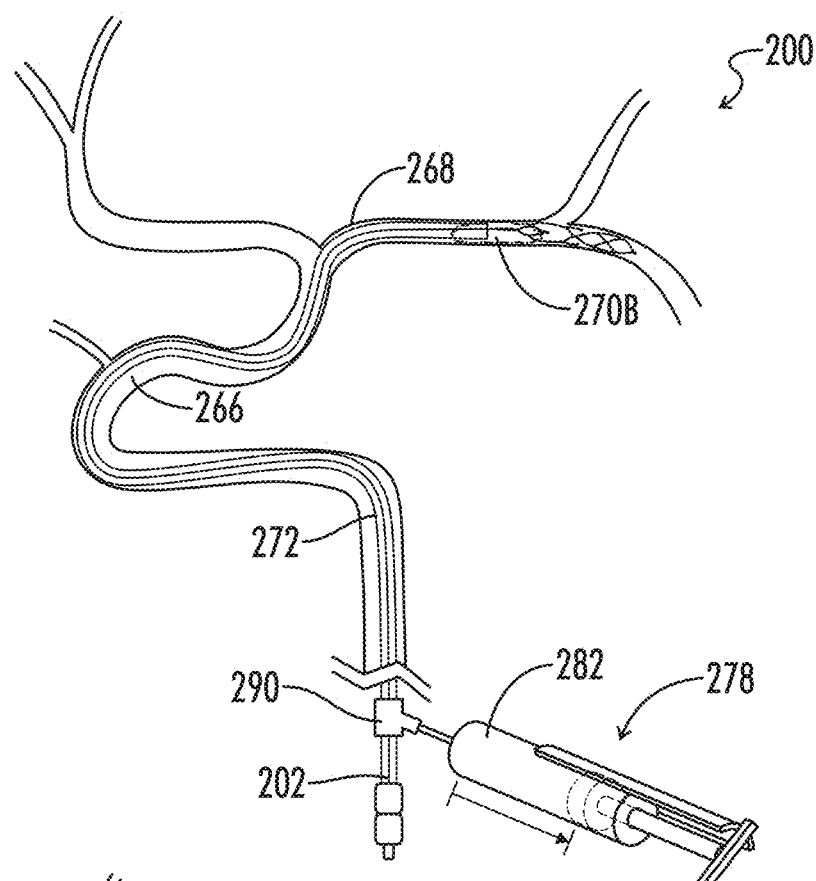
FIG. 25 shows a perspective view of the distal end of the suction catheter of FIG. 24 being pushed into a clot; a syringe is sucking the clot to the suction catheter because the user has pulled back on the lever of the syringe.
Figure 26:
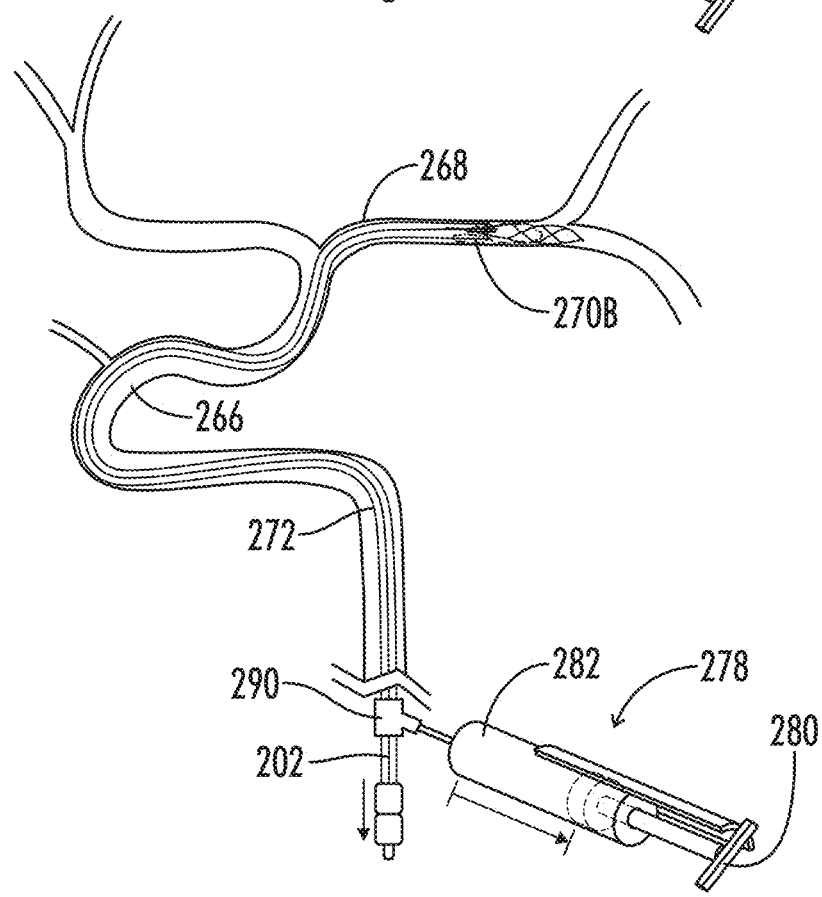
FIG. 26 shows a perspective view of the distal end of the suction catheter of FIG. 24 being pushed into a clot.
Figure 27:
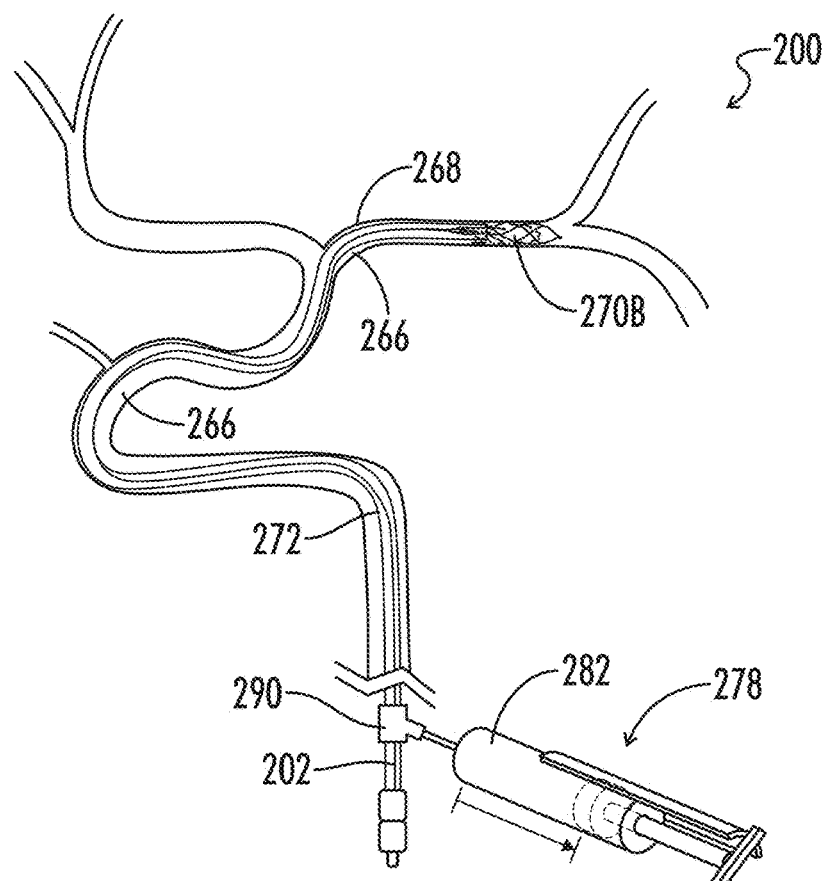
FIG. 27 shows a perspective view of the system of FIG. 24.
Figure 28:
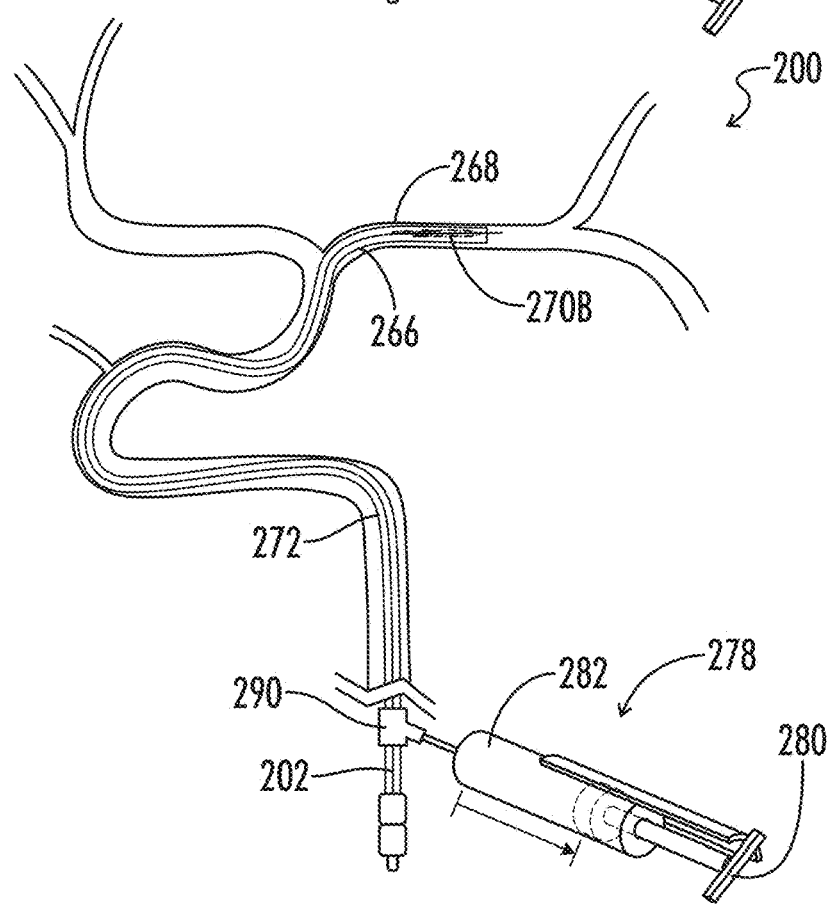
FIG. 28 shows a perspective view of the system of FIG. 24.
Figure 29:
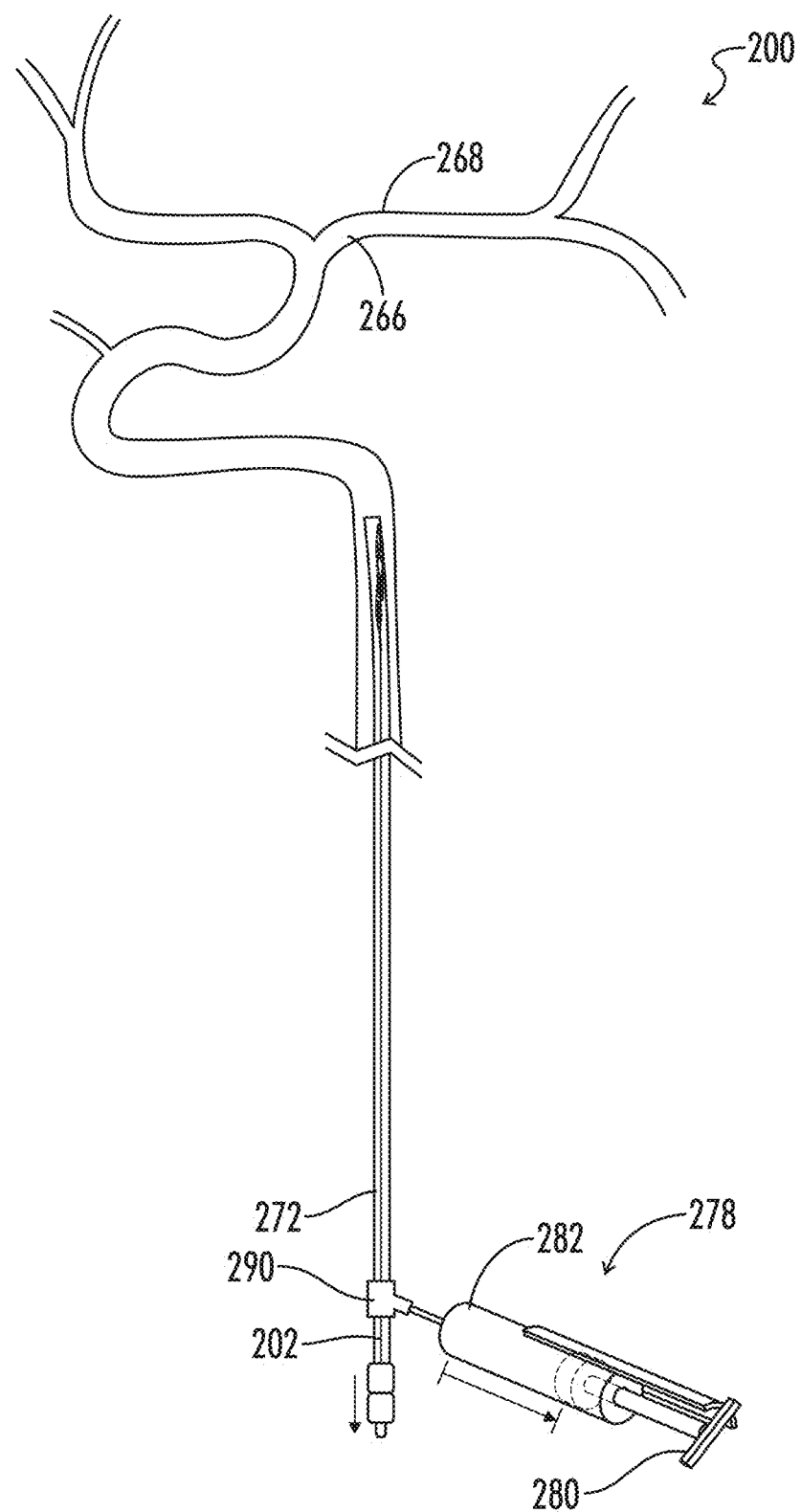
FIG. 29 shows a perspective view of the system of FIG. 24; the system, and captured clot, is being removed proximally from the vessel.

FIGS. 20A, 20B and 20C show a distal body 216 that is similar to the distal body 216 of FIGS. 14A, 14B and 14C except that the distal body 216 of FIGS. 20A, 20B and 20C is slightly shorter and its unattached, distal-pointing crowns 258A, 258B, 258C, and 258D are closer to the proximal tube 228. The shortened distal body 216 of FIGS. 20A, 20B and 20C is particularly adapted for tortuous blood vessels 266. FIG. 21-29 show stepwise deployment of the distal body 216 of FIGS. 20A, 20B and 20C in use with a manual (i.e., hand-operated), volume-dependent (i.e. volume locked) suction catheter 272 that is locked at between about 10 to about 60 cubic centimeters (cc). Optionally, the suction catheter 272 has an outer diameter of between about 0.05 inches and about 0.09 inches and its outer diameter is substantially larger than the outer diameter of the delivery catheter 208. The clot 270 is located in the vessel 266 through the use of, for example, contrast dye injected proximal and distal to the clot 270. As shown in FIG. 21, a delivery catheter 208 containing the distal body 216 of FIGS. 20A, 20B and 20C is positioned in the tortuous vessel 266 distal to the clot 270. The delivery catheter 208 is withdrawn, deploying the distal body 216. See FIG. 22. The distal body 216 is moved proximally relative to the clot 270 and tension is exerted on pull wire 202. See FIG. 23. While maintaining tension on the pull wire 202, a suction catheter 272 having a proximal end 274 and a distal end 276 is delivered over the pull wire 202 that is attached to the distal body 216. See FIG. 24. (The reason for exerting tension on the pull wire 202 is that the pull wire 202 serves as the guide/track for the movement of the suction catheter 272 and without tension, the suction catheter 272 and pull wire 202 could end up in the ophthalmic artery 288). The distal end 276 of the suction catheter 272 is positioned against the clot 270. A syringe 278 is attached to the suction catheter 272 using a rotating hemostatic valve 290, which allows the surgeon to aspirate while a pull wire 202 is in the system. The surgeon aspirates the syringe 278 by pulling back on the lever 280 to a mark on the base 282 corresponding to between about 10 and about 60 cubic centimeters of fluid. The surgeon then locks the lever 280 (and attached plunger) into place, leaving the suction catheter 272 under suction. The surgeon captures the clot 270 in the distal body 216 using the techniques described in FIGS. 15-19. The distal body 216 and clot 270 become captured by the suction catheter 272. See FIGS. 27 and 28. The surgeon then removes the suction catheter 272 and the distal body 216 and the clot 270, captured by the suction catheter 272, by moving the suction catheter 272 proximally out of the vessel 266. See FIG. 29. It is believed that the suction catheter 272 would be helpful in the event that a small portion of the clot 270 breaks off when retrieving the clot 270 using the distal body 216.

To examine effectiveness of the systems 200, the systems 200 of FIGS. 11-20, without the use of a suction catheter 272, were used to retrieve soft and hard clots 270A and 270B induced in a pig weighing between 30 to 50 kg. The weight of the pig was chosen so that the size of its vessels 266 would be approximate to the size of a human vessel. The pig was anesthetized. Several hard clots 270B were prepared by mixing pig blood and barium and incubating the mixture for 2 hours. Several soft clots 270A were prepared by mixing pig blood, thrombin and barium and incubating the mixture for 1 hour. The clots 270A and 270B, each of which had a width of 4 to 6 mm and a length of 10 to 40 mm, were then inserted into a vessel 266 having a diameter of 2 to 4 mm. (Only one clot 270A and 270B was located in the vessel 266 at a time). Angiograms were then performed to confirm occlusion. After waiting ten minutes after confirming occlusion, the distal bodies 216 of FIGS. 11-20 were then delivered distal to the clots 270A and 270B as described above and were used to retrieve the clots 270A and 270B as described in FIGS. 11-19. In each case, the distal bodies 216 were successful in retrieving the clots 270A and 270B.

THE EMBODIMENTS OF FIGS. 32-45

Figure 42:
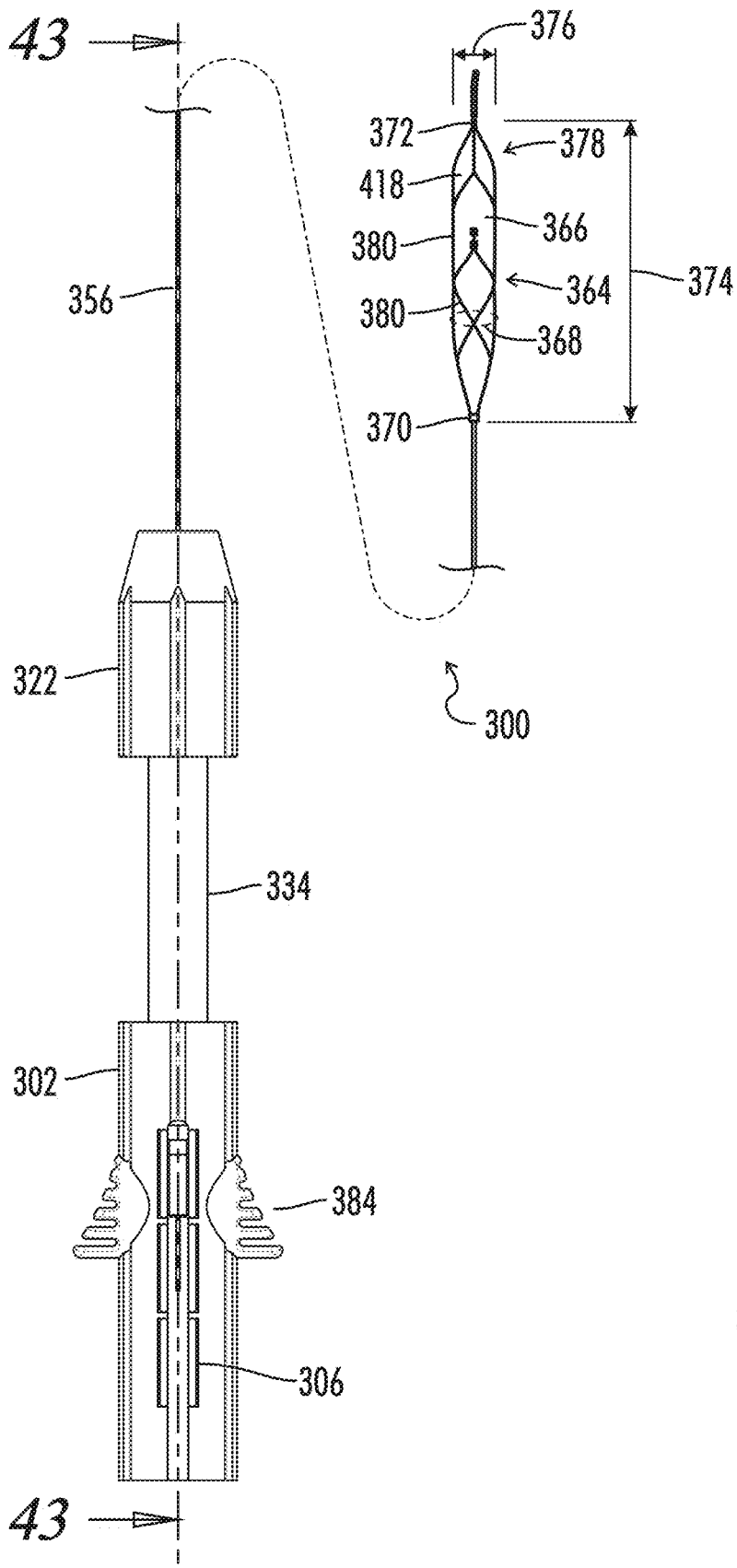
FIG. 42 illustrates a top plan view of the strain gauge and pull wire of FIG. 32A attached to a distal body.
Figure 43:
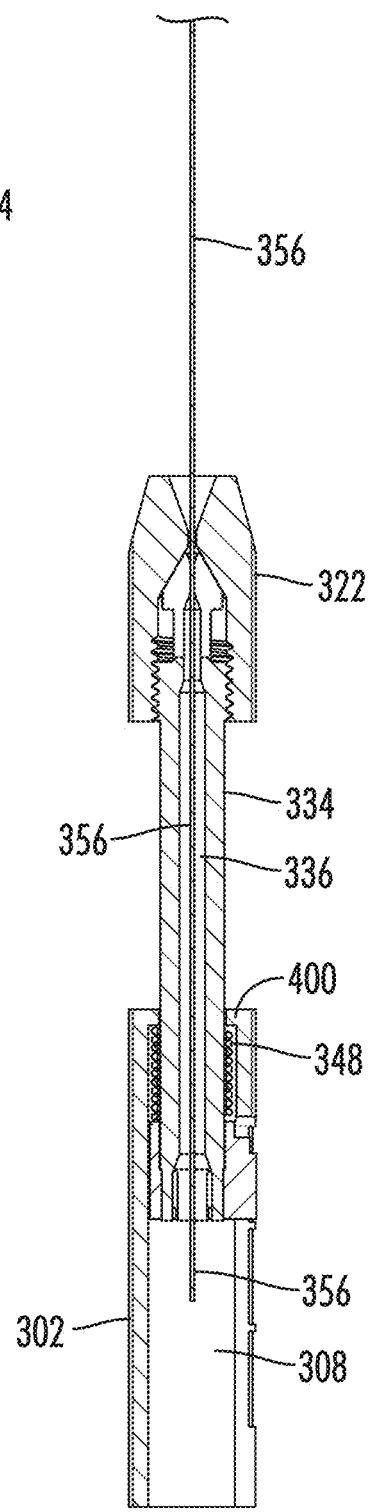
FIG. 43 illustrates a top sectional view of the strain gauge and pull wire of FIG. 32A.
Figure 44:
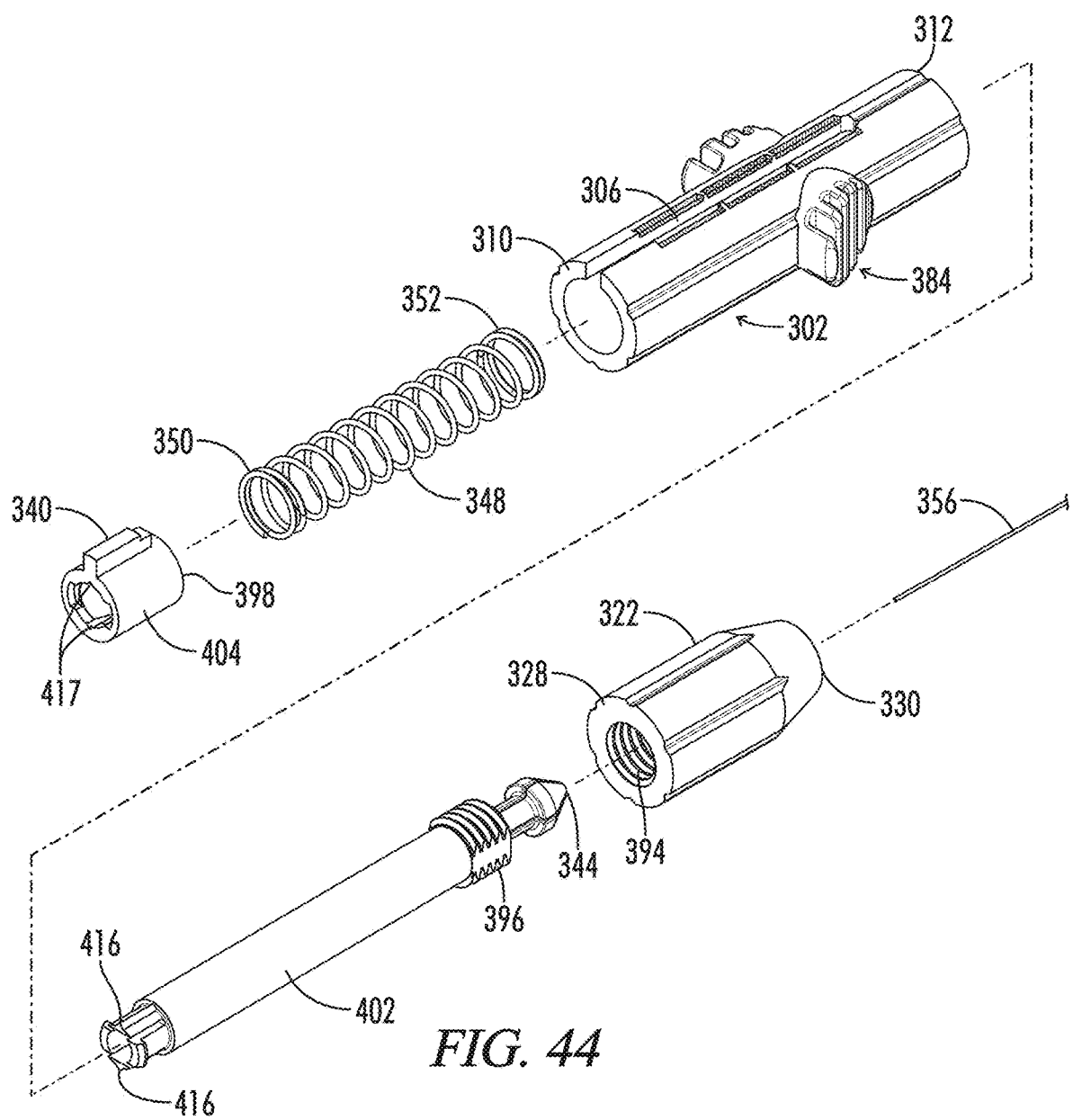
FIG. 44 illustrates a fully exploded side perspective view of the strain gauge and pull wire of FIG. 32A.

FIGS. 32-41 and 43-45 illustrate a strain gauge that may be used with any suitable stent retriever, such as (as is illustrated in FIG. 42) the distal body of FIGS. 11-20, which is currently available under the trade name NEVA from Legacy Ventures LLC dba Vesalio (Nashville, Tenn.). Alternatively, for example, the SOLITAIRE revascularization device (Medtronic, Minneapolis, Minn.), or TREVO retriever (Stryker, Kalamazoo, Mich.) or other suitable stent retrievers may be used with the strain gauge. Additional stent retrievers are described in U.S. Patent Publication 2018/0296235, the entire contents of which are incorporated herein by reference. Optionally, the strain gauge includes a clamp 392 that releasably engages the pull wire 356, which in turn is attached to a distal body 364, as shown in FIGS. 32-45. As described more particularly below, the strain gauge illustrated in FIGS. 32-45 is comprised of a proximal outer tube 302, a distal outer tube 322 and an inner tube 334.

More particularly, in some embodiments, as shown in FIGS. 32-45, the present disclosure provides a system 300 for removing a blood clot from a human blood vessel that includes a proximal outer tube 302 comprising a proximal outer tube exterior 304 comprising a slot 306, a proximal outer tube interior 308, a proximal outer tube proximal end 310, a proximal outer tube distal end 312, and a proximal outer tube length 314 extending from the proximal outer tube proximal end 310 to the proximal outer tube distal end 312. The proximal outer tube 302 serves as the handle and is held by the surgeon's hand and may include two handle flanges 384 comprising grooves 386 located on opposite sides of the proximal outer tube exterior 304 (e.g., located approximately 180 degrees apart). The surgeon's fingers may engage the handle flanges 384. Optionally, the handle flanges 384 have a proximal end 388 and a distal end 390 and the handle flanges 384 extend laterally from the proximal outer tube 302 to a greater extent at the proximal end 388 of the handle flanges 384 as compared to the distal end 390 of the handle flanges 384 so that the handle flanges 384 are sloped, as best seen in FIG. 38.

Figure 33A:
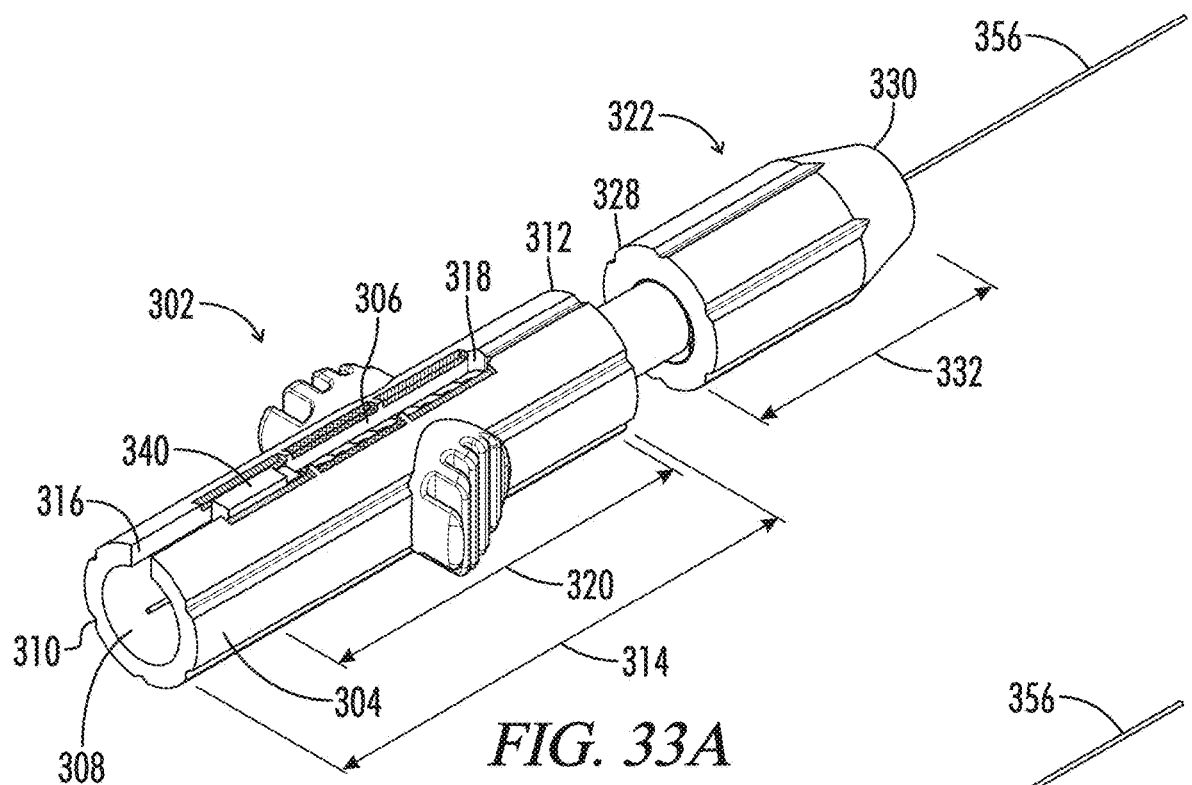
FIG. 33A illustrates a side perspective view of the strain gauge and pull wire of FIG. 32A.
Figure 33B:
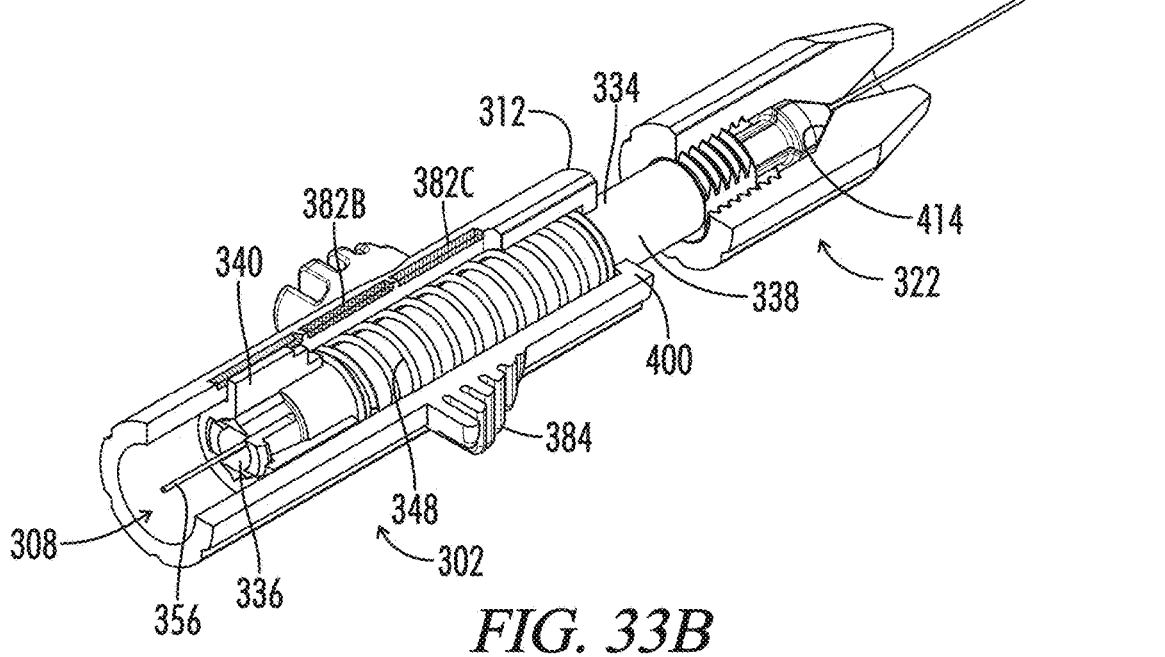
FIG. 33B illustrates a side perspective view of the strain gauge and pull wire of FIG. 33A with portions of the distal outer tube and proximal outer tube removed to better show the internal components.
Figure 45:
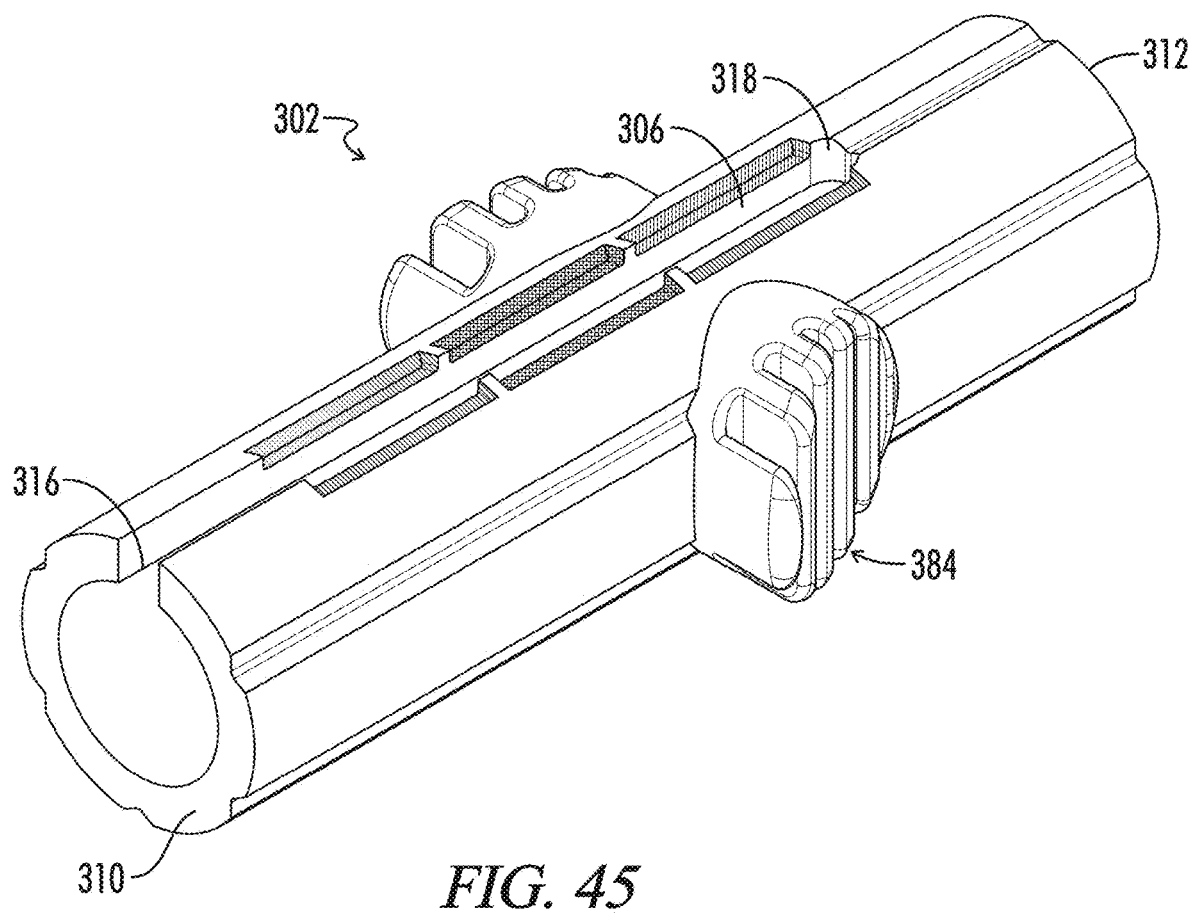
FIG. 45 illustrates a side perspective view of the proximal outer tube of the strain gauge of FIG. 32A.

Optionally, the slot 306 comprises a slot proximal end 316, a slot distal end 318, and a slot length 320 extending from the slot proximal end 316 to the slot distal end 318 and parallel to the proximal outer tube length 314. Optionally, the slot proximal end 316 extends to the proximal end 310 of the proximal outer tube 302 and the slot distal end 318 is located proximal to the distal end 312 of the proximal outer tube 302, as shown in FIG. 45 for example. In other words, the slot length 320 may be less than the proximal outer tube length 314, as shown in FIG. 33A for example.

Optionally, the system 300 further includes a distal outer tube/tightening collar 322 comprising a distal outer tube exterior 324, a distal outer tube interior 326, a distal outer tube proximal end 328 located distal to the proximal outer tube distal end 312, a distal outer tube distal end 330, a distal outer tube length 332 extending from the distal outer tube proximal end 328 to the distal outer tube distal end 330. Optionally, the distal outer tube proximal end 328 is not attached to the proximal outer tube distal end 312 so that the proximal outer tube 302 can move proximally relative to the distal outer tube 322, as shown in FIGS. 33A, 33B, 34A, 34B, 35A, 35B, 42, 43, for example, as tension is placed on the pull wire 356, as described below.

Optionally, the system 300 further includes an inner tube/stem 334 extending from the proximal outer tube interior 308 to the distal outer tube interior 326, the inner tube 334 comprising an inner tube interior 336, an inner tube exterior 338 comprising a fin 340 (which in turn is positioned in the proximal outer tube slot 306), an inner tube proximal end 342, an inner tube distal end 344 and an inner tube length 346 extending from the inner tube proximal end 342 to the inner tube distal end 344. The inner tube 334 has a smaller height and width than the height and width of the proximal outer tube 302 and the distal outer tube 322.

Optionally, the system 300 further includes a compressible spring 348 having a spring proximal end 350, a spring distal end 352, and a spring length 354 extending from the spring proximal end 350 to the spring distal end 352.

Optionally, the system 300 further includes a pull wire 356 having a pull wire proximal end 358 that optionally is located proximal to the proximal outer tube proximal end 310 and a pull wire distal end 360 that is optionally located distal to the distal outer tube distal end 330.

Optionally, the proximal outer tube proximal end 310, the distal outer tube distal end 330, the inner tube proximal and distal ends 342 and 344 are open to allow the pull wire 356 to pass therethrough, the proximal outer tube distal end 312 and the distal outer tube proximal end 328 are open to allow the inner tube 334 (and the pull wire 356 contained therein) to pass therethrough, the inner tube interior 336 is hollow to accommodate the pull wire 356 and the proximal and distal outer tubes interiors 308 and 326 are hollow to accommodate the inner tube 334 and pull wire 356.

Optionally, the pull wire 356 extends through the inner tube interior, proximal end and distal end 336, 342 and 344, as well as the proximal outer tube interior, proximal end, and distal end 308, 310 and 312 and distal outer tube interior, proximal end and distal end 326, 328 and 330.

Optionally, the system 300 further includes a distal body 364 located distal to the distal outer tube 322 and that may include a distal body interior 366, a distal body perimeter 368, a distal body proximal end 370 connected to the pull wire 356, a distal body distal end 372, a distal body length 374 extending from the distal body proximal end 370 to the distal body distal end 372, and a distal body height (not labelled) and width 376 perpendicular to the distal body length 374, the distal body 364 comprising a framework 378 comprised of a plurality of cells 418 formed by a plurality of memory metal strips 380. The distal body 364 may have a relaxed state wherein the distal body 364 has a first height and a first width 376, and a collapsed state wherein the distal body 364 has a second height and a second width 376, the second height of the distal body 364 less than the first height of the distal body 364, the second width of the distal body 364 less than the first width of the distal body 364. As noted above, preferably, the distal body 364 is a stent retriever.

Optionally, the inner tube 334 (and attached fin 340) is attached to the distal outer tube 322 and automatically moves along with the distal outer tube 322, (as well as the pull wire 356, and the distal body 364 when the clamp 392 mentioned below is in the closed position) in the lengthwise direction. In other words, when the clamp 392 is in the closed position, pulling the distal outer tube 322 proximally automatically moves the inner tube 334 (and attached fin 340), pull wire 356 and the distal body 364 proximally, and similarly, pushing the distal outer tube 322 distally automatically moves the inner tube 334 (and attached fin 340), pull wire 356, and the distal body 364 distally.

Figure 32A:
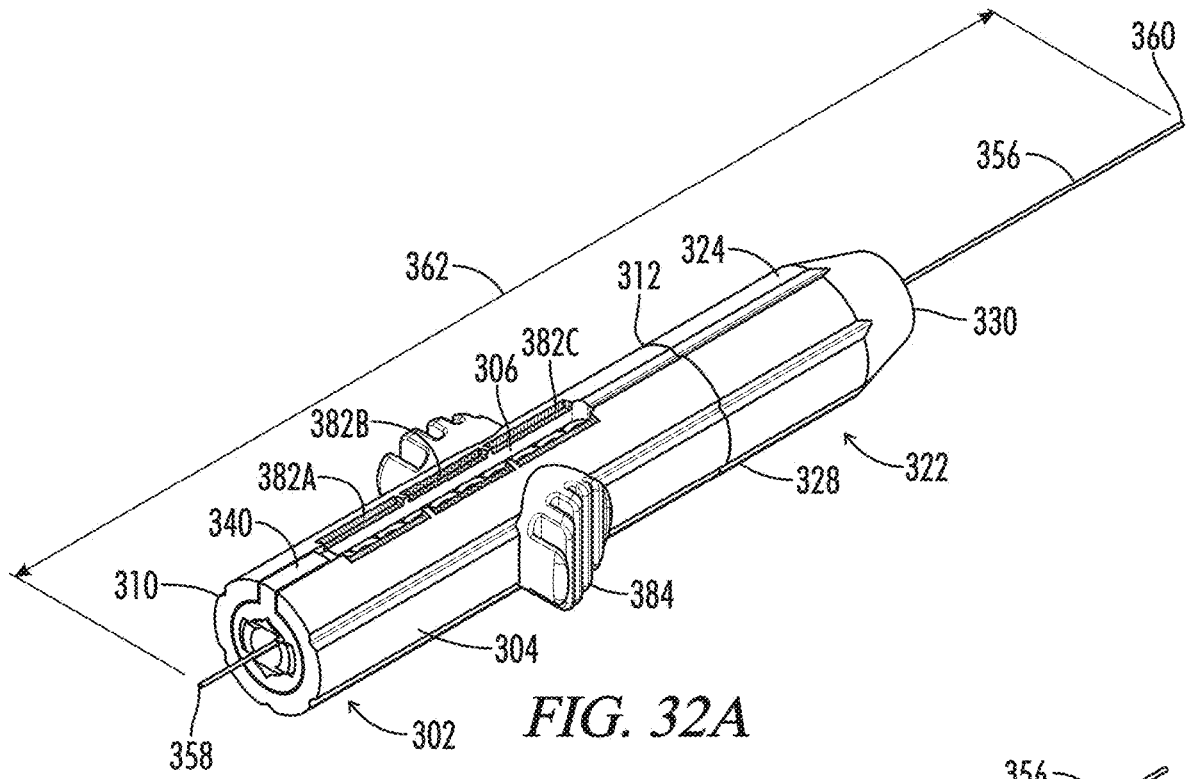
FIG. 32A illustrates a side perspective view of a strain gauge and pull wire of a clot retrieval system of another embodiment of the present invention.
Figure 32B:
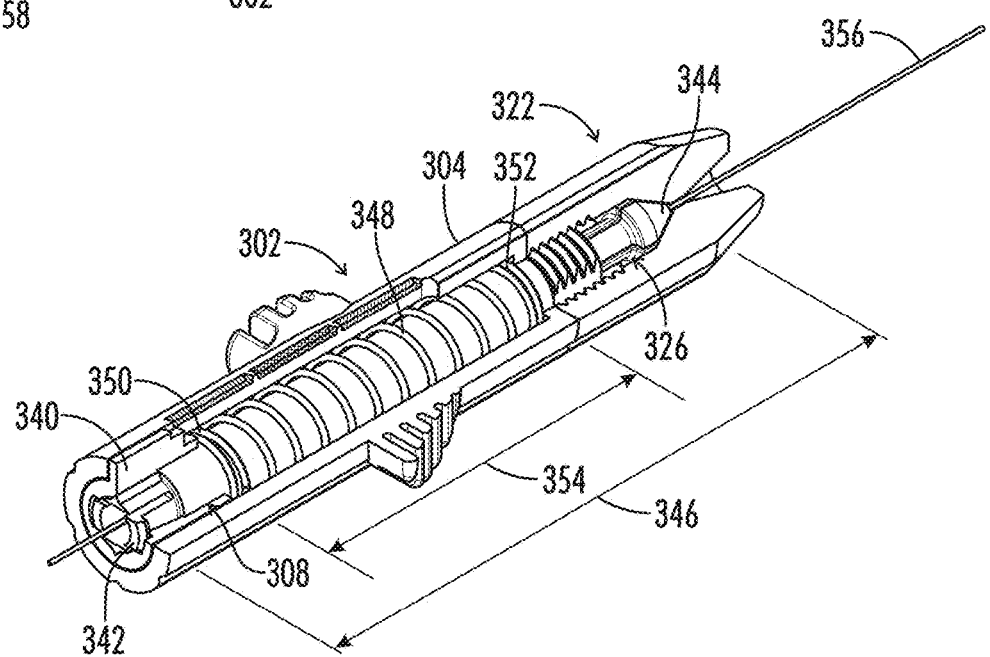
FIG. 32B illustrates a side perspective view of the strain gauge and pull wire of FIG. 32A with portions of the distal outer tube and proximal outer tube removed to better show the internal components.

Optionally, when the clamp 392 is in the closed position, the proximal outer tube 302 is configured to move proximally for a pre-determined distance relative to the inner tube 334, distal outer tube 322, the pull wire 356 and the distal body 364 in the lengthwise direction so the proximal outer tube 302 moves from a position in which the distal end of the proximal outer tube 312 abuts the proximal end of the distal outer tube 322, as shown in FIGS. 32A, 32B and 38, for example, to a position in which the distal end of the proximal outer tube 312 does not abut the proximal end of the distal outer tube 328, as shown in FIGS. 33A, 33B, 34A, 34B, 35A, 35B, 42, 43, for example.

Figure 34A:
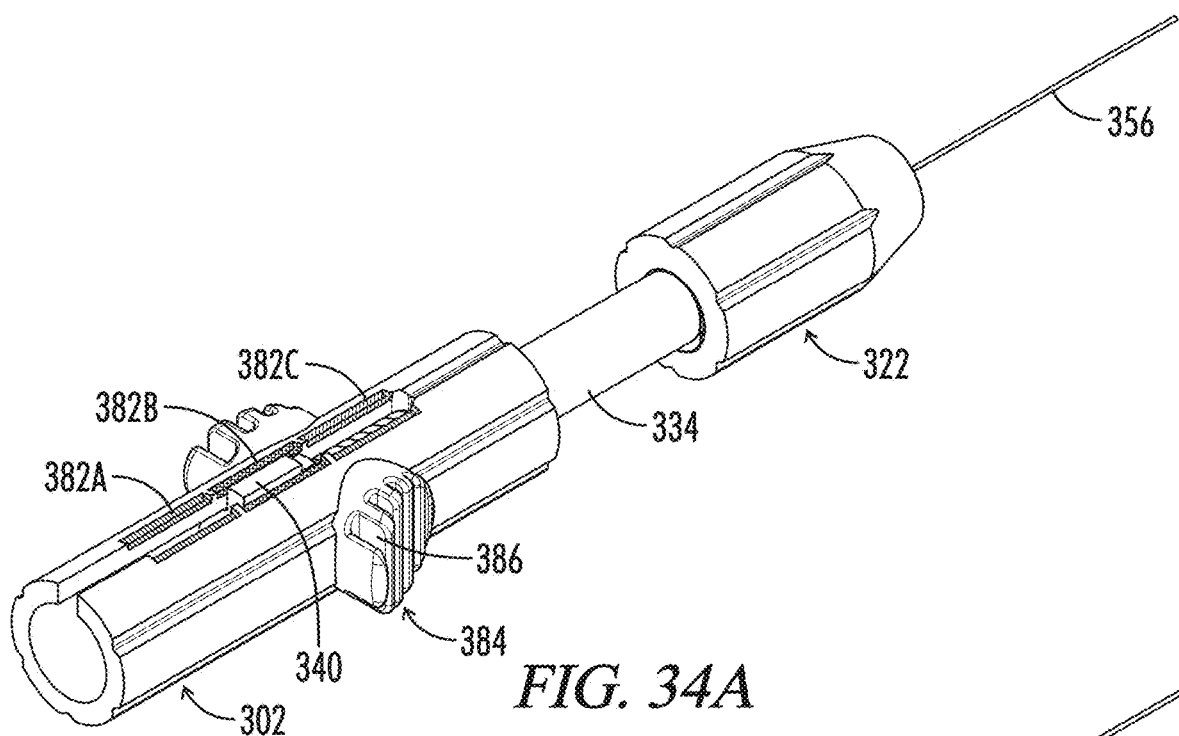
FIG. 34A illustrates a side perspective view of the strain gauge and pull wire of FIG. 32A.
Figure 34B:
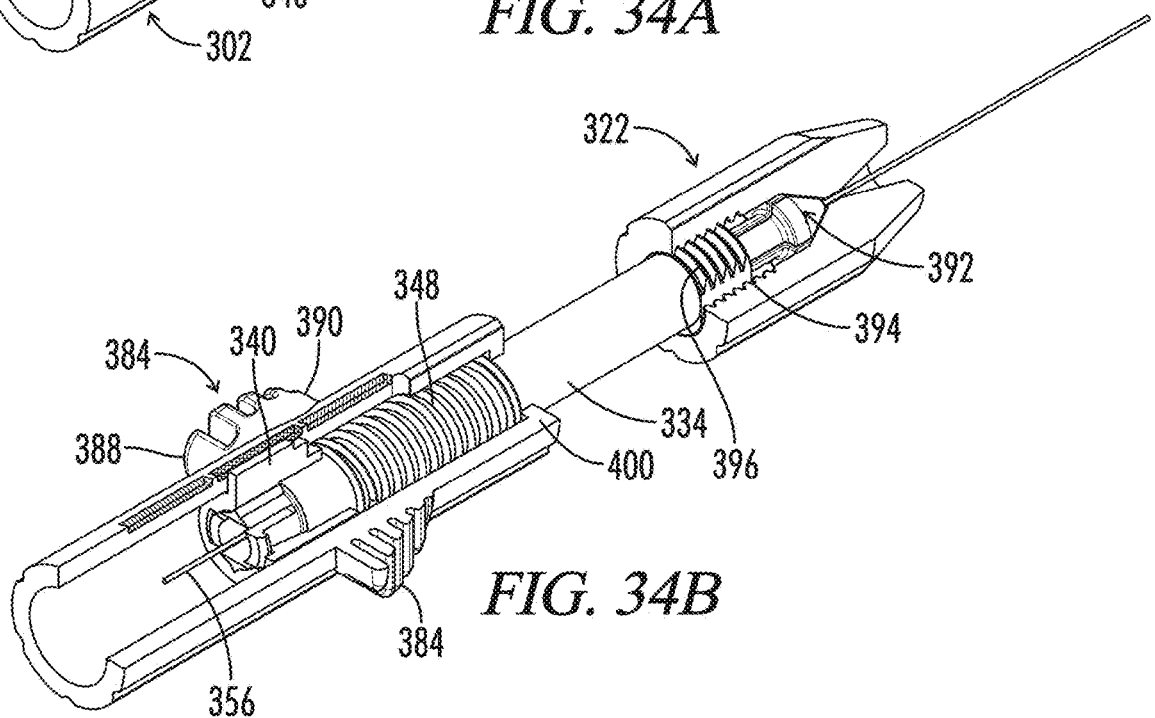
FIG. 34B illustrates a side perspective view of the strain gauge and pull wire of FIG. 34A with portions of the distal outer tube and proximal outer tube removed to better show the internal components.
Figure 35A:
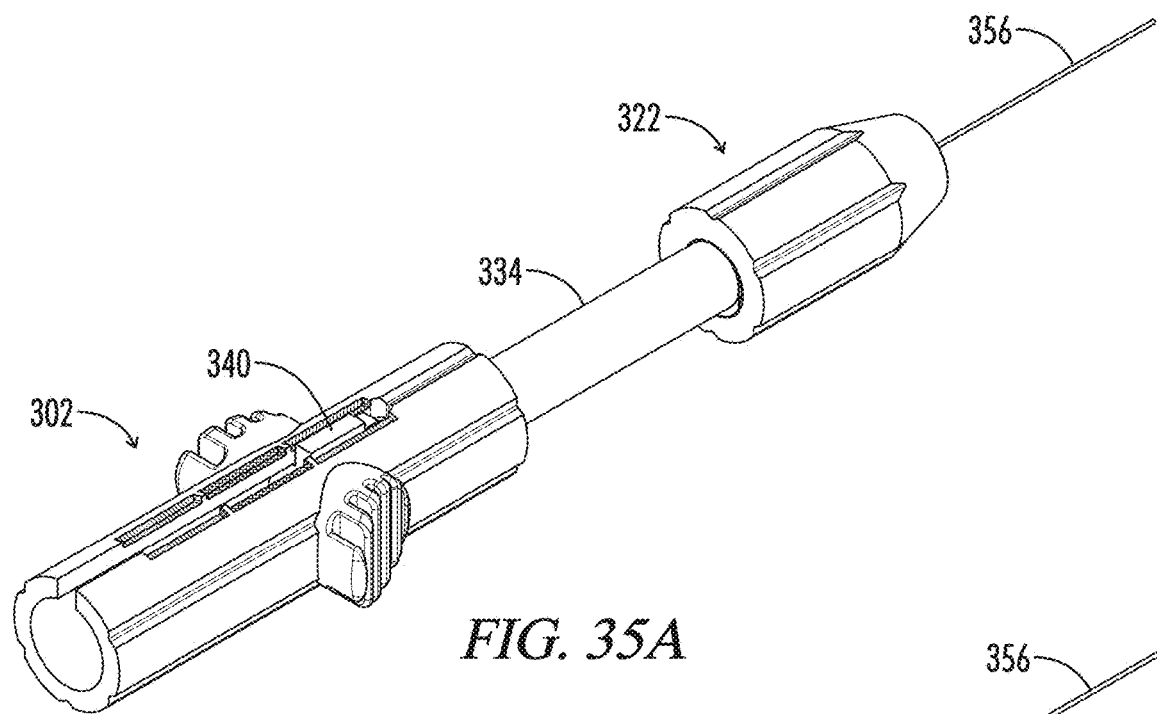
FIG. 35A illustrates a side perspective view of the strain gauge and pull wire of FIG. 32A.
Figure 35B:
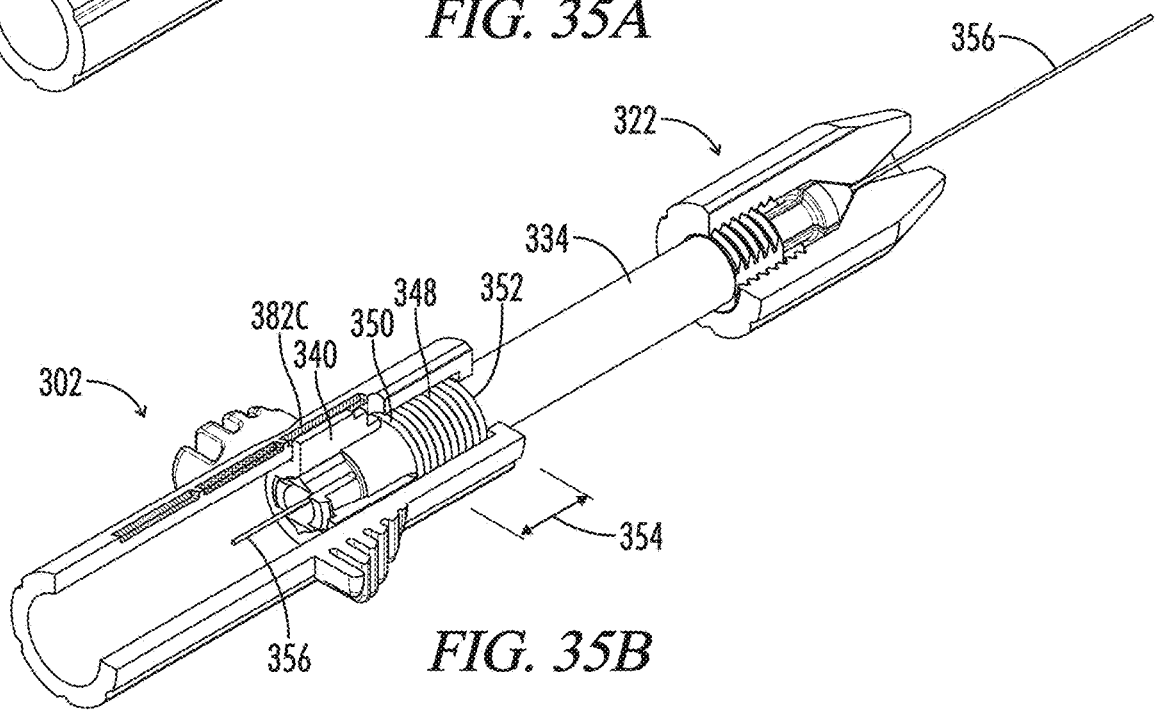
FIG. 35B illustrates a side perspective view of the strain gauge and pull wire of FIG. 35A with portions of the distal outer tube and proximal outer tube removed to better show the internal components.

Optionally, moving the proximal outer tube 302 proximally relative to the distal outer tube 322, the inner tube 334, the pull wire 356 and the distal body 364 causes the proximal outer tube slot 306 to move proximally relative to the fin 340 and causes the spring 348 to move from a relaxed length to a compressed length. Such movement allows the fin 340 to move relative to proximal outer tube indicia 382A, 382B, and 382C, which are adjacent to the slot 306. For example, the proximal-most indicia 382A may represent the least resistance on the pull wire 356 and may be labelled green, indicating to the surgeon that when the fin 340 is adjacent or proximal to the proximal-most indicia 382A (as shown in FIGS. 32A and 33A, for example) the surgeon is able to freely move the proximal outer tube 302 proximally with minimal caution (and thereby the system 300 proximally). Similarly, the middle indicia 382B may represent a medium level of resistance on the pull wire 356 and may be labelled yellow, indicating to the surgeon that when the fin 340 is adjacent to the middle indicia 382B (as shown in FIG. 34A, for example) the surgeon should exercise caution when moving the proximal outer tube 302 proximally (and thereby the system 300 proximally), because of the increased resistance on the pull wire 356. Finally, the distal indicia 382C may represent the most resistance on the pull wire 356 and may be labelled red, indicating to the surgeon that when the fin 340 is adjacent to the distal indicia 382C (as shown in FIG. 35A, for example) the surgeon should exercise more caution when moving the proximal outer tube 302 proximally (and thereby the system 300 proximally), because of the increased resistance on the pull wire 356 may indicate that distal body 364 is caught on something in the human's vasculature system. Thus, a feature of the system 300 is to provide tensile feedback to the surgeon as the surgeon pulls the system 300 proximally so that the surgeon does not break the pull wire 356 or cause the pull wire 356 to separate from distal body 364 or damage the vessel and the indicia 382A-382C may be in the form of colors to indicate various tension zones. The proximal indicia 382A may be calibrated at, for example, 0-1.49 pounds of tension, the middle indicia 382B may be calibrated at, for example, 1.5-2.99 pounds of tension and the distal indicia 382C may be calibrated at, for example, over 3 pounds of tension.

Figure 36:
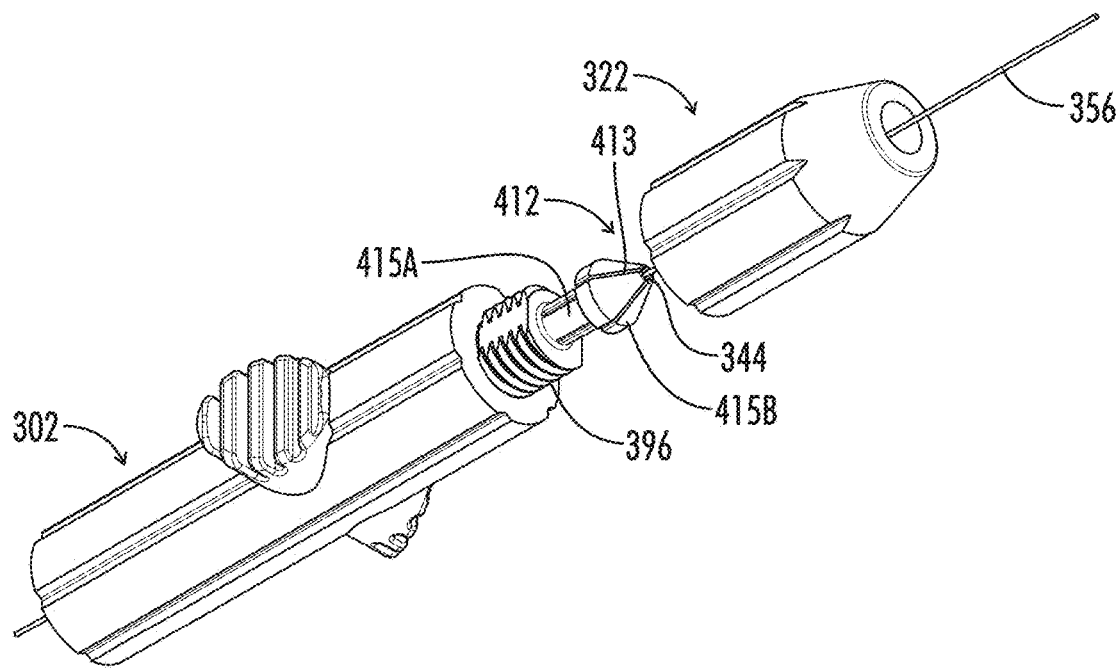
FIG. 36 illustrates a partially exploded side perspective view of the strain gauge and pull wire of FIG. 32A.
Figure 37:
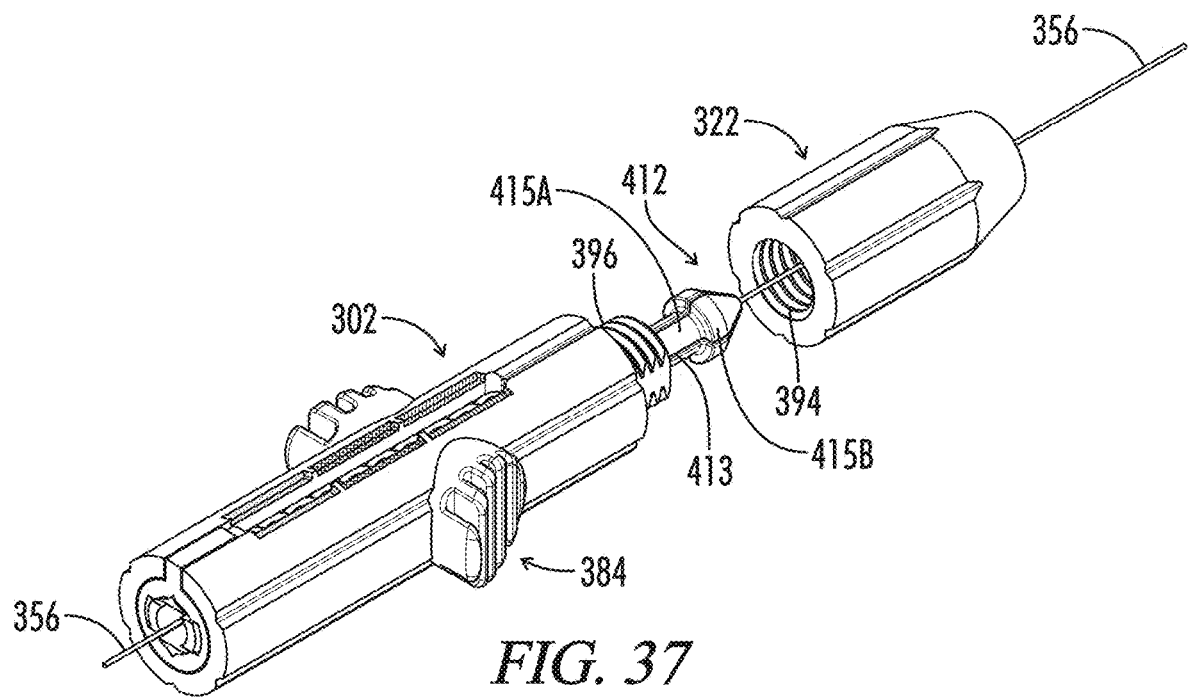
FIG. 37 illustrates a partially exploded side perspective view of the strain gauge and pull wire of FIG. 36; like FIG. 36, in FIG. 37, the inner tube is exploded from the distal outer tube.

Optionally, at least one of the distal outer tube 322 and the inner tube distal end 344 comprises a clamp 392 configured to close around the pull wire 356 and releasably engage the pull wire 356. For example, optionally the clamp 392 is comprised of two or more clamping segments 415A and 415B with the outer surface of the clamping segments 415A and 415B having two or more slits 413 extending therethrough and formed into an inner tube tapered portion 412. Optionally the distal outer tube interior 326 comprises inner tube threads 396 and a conical tapered interior surface 414. For example, when the conical tapered interior surface 414 of the distal outer tube 322 is drawn into contact with the inner tube tapered portion 412, the clamping segments 415A and 415B are forced to collapse and clamp onto pull wire 356. Optionally the inner tube 334 comprises an inner tube height (not labelled) and an inner tube width 410, and the inner tube distal end 344 comprises a inner tube tapered portion 412 in which the inner tube height and width 410 decrease at the inner tube distal end 344, as shown in FIGS. 36 and 40 for example. Additionally, optionally, the distal outer tube interior 326 and the inner tube 334 comprise mating threads, wherein moving the inner tube threads 396 along the distal outer tube interior threads 394 in a first direction causes the conical tapered interior surface/wall 414 of the distal outer tube 322 to contact and apply pressure to the inner tube tapered portion 412 which closes the clamp 392 around the pull wire 356 and further wherein moving the inner tube threads 396 along the distal outer tube interior threads 394 in a second direction causes the conical tapered interior surface/wall 414 to move away from and release pressure on the inner tube tapered portion 412 which opens the clamp 392 with respect to the pull wire 356. For example, rotating the distal outer tube 322 clockwise while holding the proximal outer tube 302 stationary may tighten the clamping segments 415A and 415B around the pull wire 356 (a clamp closed position), whereas rotating the distal outer tube 322 counterclockwise while holding the proximal outer tube 302 stationary may loosen the clamping segments 415A and 415B around the pull wire 356 allowing the proximal outer tube 302 and distal outer tube 322 to be moved off the pull wire 356 (a clamp open position). In other words, in the open position, the proximal outer tube 302, the distal outer tube 322 and the inner tube 334 may freely slide proximally and distally over the pull wire 356. It will be appreciated that the slits 413 allow the clamping segments 415A and 415B to radially expand to create the clamp open position and to contract to create the clamp closed position. To use the system 300, the surgeon may move the distal outer tube 322 and the proximal outer tube 302 (and attached inner tube 334) distally over the pull wire 356 (from the pull wire proximal end 358) so that the pull wire 356 is positioned in the distal outer tube and proximal outer tube interiors 326, 308 and then rotate the distal outer tube 322 clockwise while holding the proximal outer tube 302 stationary thereby forcing the clamping segments 415A and 415B to tighten and grip onto the pull wire 356 and thus fixing the proximal outer tube 302 and distal outer tube 322 on the pull wire 356. The inner tube 334 preferably does not rotate relative to the proximal outer tube 302 due to the fact that the fin 340 is located in the slot 306 and the splines 416 described below engage the spline grooves 417 of collar 404.

Another feature of the system 300 is that pull wires 356 are traditionally thin and thus difficult for the surgeon to grip and twist. Thus, the proximal outer tube 302, which is wider and taller than the pull wire 356, allows the user, when the clamp 392 is in the closed position, to more readily rotate the proximal outer tube 302 (and thereby the distal outer tube 322, which is attached to the pull wire 356 through clamp 392, which in turn is attached to the distal body 364) about the proximal outer tube length/longitudinal axis 314 in a clockwise and counterclockwise manner, thereby allowing the distal body 364 to rotate in the blood vessel if needed to capture the clot.

Optionally, the spring proximal end 350 rests against the collar distal end 398 located in the proximal outer tube interior 308 and connected to the fin 340 and the spring distal end 352 rests against a distal ledge 400 located distal to the fin 340 in the proximal outer tube interior 308.

Optionally, as shown in FIGS. 32B, 33B, 34B, 35B and 44, for example, the inner tube 334 is comprised of a rod 402 and a collar 404 enveloping the rod 402 and the collar 404 comprises the fin 340. Additionally, optionally, the spine grooves 417 of the collar 404 engage the spines 416 of the rod 402 thus preventing the collar 404 from rotating relative to the rod 402. Optionally, the fin 340 is engaged in the slot 306, thus preventing the collar 404 from rotating relative to the proximal outer tube 302. Furthermore, as rod 402 and clamp 392 are parts of inner tube 334, they are connected and as such rotate together. Additionally, if the clamp 392 is collapsed onto/engages pull wire 356 (the clamp 392 is in the closed position), then pull wire 356 cannot rotate relative to clamp 392. Therefore, through the engagement of the slot 306 with the fin 340 and the engagement of the splines 416 with the spline grooves 417 and the engagement of the clamp 392 with the pull wire 356, rotation of the proximal outer tube 302 causes rotation of the pull wire 356.

Optionally, the proximal outer tube 302, inner tube 334 and distal outer tube 322 are rigid, e.g., comprised of an injection molded plastic.

The system 300 may be used in a method of removing a blood clot from a blood vessel of a human the method comprising the steps of: a) providing the system 300; b) positioning a catheter (not shown but previously described) comprising the distal body 364 in the blood vessel; c) deploying the distal body 364 from the catheter and allowing the height and width 376 of the distal body 364 to increase; d) capturing the blood clot with the distal body 364; and e) moving the distal body 364 proximally out of the blood vessel by pulling proximally on the proximal outer tube 302.

| Part List for FIGS. 32-45 | |
|---|---|
| system | 300 |
| proximal outer tube | 302 |
| proximal outer tube exterior | 304 |
| slot | 306 |
| proximal outer tube interior | 308 |
| proximal outer tube proximal end | 310 |
| proximal outer tube distal end | 312 |
| proximal outer tube length | 314 |
| slot proximal end | 316 |
| slot distal end | 318 |
| slot length | 320 |
| distal outer tube | 322 |
| distal outer tube exterior | 324 |
| distal outer tube interior | 326 |
| distal outer tube proximal end | 328 |
| distal outer tube distal end | 330 |
| distal outer tube length | 332 |
| inner tube | 334 |
| inner tube interior | 336 |
| inner tube exterior | 338 |
| fin | 340 |
| inner tube proximal end | 342 |
| inner tube distal end | 344 |
| inner tube length | 346 |
| spring | 348 |
| spring proximal end | 350 |
| spring distal end | 352 |
| spring length | 354 |
| pull wire | 356 |
| pull wire proximal end | 358 |
| pull wire distal end | 360 |
| pull wire length | 362 |
| distal body | 364 |
| distal body interior | 366 |
| distal body perimeter | 368 |
| distal body proximal end | 370 |
| distal body distal end | 372 |
| distal body length | 374 |
| distal body width | 376 |
| distal body framework | 378 |
| distal body memory metal strips | 380 |
| indicia | 382A, 382B, 382C |
| handle flange | 384 |
| flange groove | 386 |
| flange proximal end | 388 |
| flange distal end | 390 |
| clamp | 392 |
| distal outer tube threads | 394 |
| inner tube threads | 396 |
| collar distal end | 398 |
| distal ledge | 400 |
| rod | 402 |
| collar | 404 |
| inner tube width | 410 |
| inner tube tapered portion | 412 |
| slits | 413 |
| conical tapered interior surface/wall | 414 |
| clamping segments | 415A and 415B |

-continued

Part List for FIGS. 32-45

| splines | 416 |
| spline grooves | 417 |
| distal body cells | 418 |

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention, as defined and limited solely by the following claims. In particular, although the system has been exemplified for use in retrieving blood clots, the system may be used to retrieve other objects from animal lumens. In addition, the steps of any method described herein may be performed in any suitable order and steps may be performed simultaneously if needed.

Terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A system for removing a blood clot from a human blood vessel, the system comprising:
a proximal outer tube comprising a proximal outer tube exterior comprising a slot, a proximal outer tube interior, a proximal outer tube proximal end, a proximal outer tube distal end, and a proximal outer tube length extending from the proximal outer tube proximal end to the proximal outer tube distal end, wherein the slot comprises a slot proximal end, a slot distal end, and a slot length extending from the slot proximal end to the slot distal end and parallel to the proximal outer tube length;
a distal outer tube comprising a distal outer tube exterior, a distal outer tube interior, a distal outer tube proximal end located distal to the proximal outer tube distal end, a distal outer tube distal end, a distal outer tube length extending from the distal outer tube proximal end to the distal outer tube distal end, the distal outer tube proximal end not attached to the proximal outer tube distal end;
an inner tube extending from the proximal outer tube interior to the distal outer tube interior, the inner tube comprising an inner tube interior, an inner tube exterior comprising a fin positioned in the proximal outer tube slot, an inner tube proximal end, an inner tube distal end and an inner tube length extending from the inner tube proximal end to the inner tube distal end;
a compressible spring having a spring proximal end, a spring distal end, and a spring length extending from the spring proximal end to the spring distal end;
a pull wire having a pull wire proximal end and a pull wire distal end located distal to the distal outer tube distal end,
a distal body located distal to the distal outer tube and comprising a distal body interior, a distal body perimeter, a distal body proximal end connected to the pull wire, a distal body distal end, a distal body length extending from the distal body proximal end to the distal body distal end, and a distal body height and width perpendicular to the distal body length, the distal body comprising a framework formed by a plurality of memory metal strips, wherein the distal body has a relaxed state wherein the distal body has a first height and a first width, and a collapsed state wherein the distal body has a second height and a second width, the second height of the distal body less than the first height of the distal body, the second width of the distal body less than the first width of the distal body,
wherein at least one of the distal outer tube and the inner tube comprises a clamp having a closed position in which the clamp closes around the pull wire and an open position in which the clamp is open with respect to the pull wire,
wherein, when the clamp is in the open and closed position, the inner tube is attached to the distal outer tube and moves along with the distal outer tube in the lengthwise direction,
wherein, at least when the clamp is in the closed position, the proximal outer tube is configured to move proximally for a pre-determined distance relative to the inner tube, distal outer tube, the pull wire and the distal body in the lengthwise direction,
wherein, at least when the clamp is in the closed position, moving the proximal outer tube proximally relative to the distal outer tube, the inner tube, the pull wire and the distal body causes the proximal outer tube slot to move proximally relative to the fin and causes the spring to move from a relaxed length to a compressed length.

2. The system of claim 1 wherein, when the clamp is in the closed position, rotating the proximal outer tube about the proximal outer tube length in a clockwise and counterclockwise direction is configured to rotate the distal outer tube, the pull wire and the distal body.

3. The system of claim 2 wherein, when the clamp is in the open position, rotating the proximal outer tube about the proximal outer tube length in a clockwise and counterclockwise direction is configured to rotate the distal outer tube but neither the pull wire nor the distal body.

4. The system of claim 1 wherein, when the clamp is in the open position, the proximal outer tube is configured to move proximally for a pre-determined distance relative to at least the inner tube and the distal outer tube in the lengthwise direction.

5. The system of claim 1 wherein, when the clamp is in the open position, the proximal outer tube, the inner tube, and the distal outer tube are freely slideable over the pull wire in the proximal and distal directions.

6. The system of claim 1 wherein the system comprises a relaxed position in which the proximal outer tube distal end abuts against the distal outer tube proximal end and in which the spring is the relaxed length and a second position in which the distal end of the proximal outer tube does not abut the proximal end of the distal outer tube and in which the spring is the compressed length.

7. The system of claim 1 wherein the proximal outer tube exterior comprises indicia adjacent to the slot.

8. The system of claim 1 wherein the proximal outer tube exterior comprises two handle flanges comprising grooves located on opposite sides of the proximal outer tube exterior.

9. The system of claim 8 wherein the handle flanges have a proximal end and a distal end and further wherein the handle flanges extend laterally from the proximal outer tube to a greater extent at the proximal end of the handle flanges as compared to the distal end of the handle flanges.

10. The system of claim 1 wherein the inner tube comprises an inner tube height and an inner tube width, and further wherein the inner tube distal end comprises a tapered portion in which the inner tube height and width decrease at the inner tube distal end.

11. The system of claim 10 wherein the distal outer tube interior and the inner tube comprise mating threads, wherein moving the inner tube threads along the distal outer tube interior threads in a first direction moves the clamp to the closed position and further wherein moving the inner tube threads along the distal outer tube interior threads in a second direction moves the clamp to the open position.

12. The system of claim 1 wherein the slot proximal end is at the proximal end of the proximal outer tube.

13. The system of claim 1 wherein the inner tube is comprised of a rod and a collar enveloping the rod and further wherein the collar comprises the fin.

14. The system of claim 1 wherein the slot length is less than the proximal outer tube length.

15. The system of claim 1 wherein the proximal outer tube distal end, the distal outer tube proximal end, and the inner tube distal end are open and the pull wire extends through at least the inner tube open distal end.

16. The system of claim 15 wherein the proximal outer tube interior is hollow, the proximal outer tube proximal end is open, the distal outer tube interior is hollow, the inner tube interior is hollow, the distal outer tube distal end is open and the inner tube proximal end is open.

17. The system of claim 16 wherein the pull wire proximal end is proximal to the proximal outer tube open proximal end, and further wherein the pull wire extends through the inner tube hollow interior, the inner tube open proximal end, the distal outer tube open proximal end, the distal outer tube open distal end, the distal outer tube hollow interior, the proximal outer tube open distal end, the proximal outer tube hollow interior, and the proximal outer tube open proximal end.

18. A method of removing a blood clot from a blood vessel of a human the method comprising the steps of:
 a) providing the system of claim 1;
 b) positioning a catheter comprising the distal body in the blood vessel;
 c) deploying the distal body from the catheter and allowing the height and width of the distal body to increase;
 d) capturing the blood clot with the distal body; and
 e) moving the distal body proximally out of the blood vessel by grasping and pulling proximally on the proximal outer tube.

19. The method claim 18 further comprising the step of rotating the distal body in the blood vessel by rotating the proximal outer tube.

* * * * *